United States Patent
Darbre et al.

(10) Patent No.: US 10,336,792 B2
(45) Date of Patent: Jul. 2, 2019

(54) ANTIMICROBIAL PEPTIDE DENDRIMERS

(71) Applicant: UNIVERSITAT BERN, Bern (CH)

(72) Inventors: Tamis Darbre, Munsingen (CH); Jean-Louis Reymond, Bulle (CH); Michaela Stach, Mosbach (DE)

(73) Assignee: UNIVERSITAT BERN, Bern (CH)

( * ) Notice: Subject to any disclaimer, the term of this patent is extended or adjusted under 35 U.S.C. 154(b) by 0 days.

(21) Appl. No.: 15/129,846

(22) PCT Filed: Mar. 27, 2015

(86) PCT No.: PCT/EP2015/056819
§ 371 (c)(1),
(2) Date: Sep. 28, 2016

(87) PCT Pub. No.: WO2015/144928
PCT Pub. Date: Oct. 1, 2015

(65) Prior Publication Data
US 2017/0137471 A1    May 18, 2017

(30) Foreign Application Priority Data

Mar. 28, 2014  (EP) .................................. 14162252

(51) Int. Cl.
| | | |
|---|---|---|
| *C07K 14/01* | (2006.01) | |
| *C07K 14/00* | (2006.01) | |
| *C07K 7/06* | (2006.01) | |
| *C07K 7/08* | (2006.01) | |
| *A61K 38/00* | (2006.01) | |

(52) U.S. Cl.
CPC .............. *C07K 14/001* (2013.01); *C07K 7/06* (2013.01); *C07K 7/08* (2013.01); *A61K 38/00* (2013.01); *Y02A 50/473* (2018.01)

(58) Field of Classification Search
CPC ...... A61K 31/785; A61K 31/74; A61K 47/60; C07K 14/001
See application file for complete search history.

(56) References Cited

FOREIGN PATENT DOCUMENTS

WO    WO2009/025691    2/2009

OTHER PUBLICATIONS

Uretsky, Antiviral drug, Gale Encyclopedia of Children's Health: Infancy through Adolescence, 2006, Encyclopedia.com, Available online at Http://www.encyclopedia.com/topic/antiviral_drug.aspx, accessed May 26, 2016. (Year: 2016).*
Kadam et al., Angew. Chem. Int. Ed. 2011, 50, 10631-10635. (Year: 2011).*
M Stach et al.: "Membrane disrupting antimicrobial peptide dendrimers with multiple amino termini", Medchemcomm, vol. 3, No. 1, 2012, pp. 85-89.
M Stach et al.: "Combining topology and sequence design for the discovery of potent antimicrobial peptide dendrimers against multidrug-resitant Pseudomonas aeruginosa", Angewandte Chemie International Edition, vol. 53, No. 47, Nov. 17, 2014, pp. 12827-12831.
Siriwardena, T., Capecchi, A., Gan, B.H., Jin, X., He, R., Wei, D., Ma, L., Köhler, T., van Delden, C., Javor, S. and Reymond, J.L., "Optimizing Antimicrobial Peptide Dendrimers in Chemical Space." Angewandte Chemie Int. 2018, 57, 8483-8487.
Kadam, R.U., Bergmann, M., Hurley, M., Garg, D., Cacciarini, M., Swiderska, M.A., Nativi, C., Sattler, M., Smyth, A.R., Nilliams, P. and Cámara, M., 2011. A glycopeptide dendrimer inhibitor of the galactose-specific lectin LecA and of Pseudomonas aeruginosa biofilms. Angewandte Chemie International Edition, 50(45), pp. 10631-10635.

* cited by examiner

*Primary Examiner* — Rachael E Bredefeld
*Assistant Examiner* — Kaipeen E Yang
(74) *Attorney, Agent, or Firm* — JMB Davis Ben-David

(57) ABSTRACT

The invention relates to a peptide dendrimer described by a general formula $X-(B^2-[Y^2]_S-D^1)_2-B^1-Z$, wherein X is $(D^2)4$ or $(D^3)_8-(B^3-[Y^3]_r-D^2)_4$ or a higher analog, Y is a linkage moiety, Z is a central moiety; each B denotes a diaminoalkylcarboxylic acid moiety; each D is a hydrophobic or cationic amino acid, or a di- or tripeptide composed of hydrophobic and cationic amino acids, for use as a pharmaceutical.

9 Claims, 10 Drawing Sheets

Figure 1:
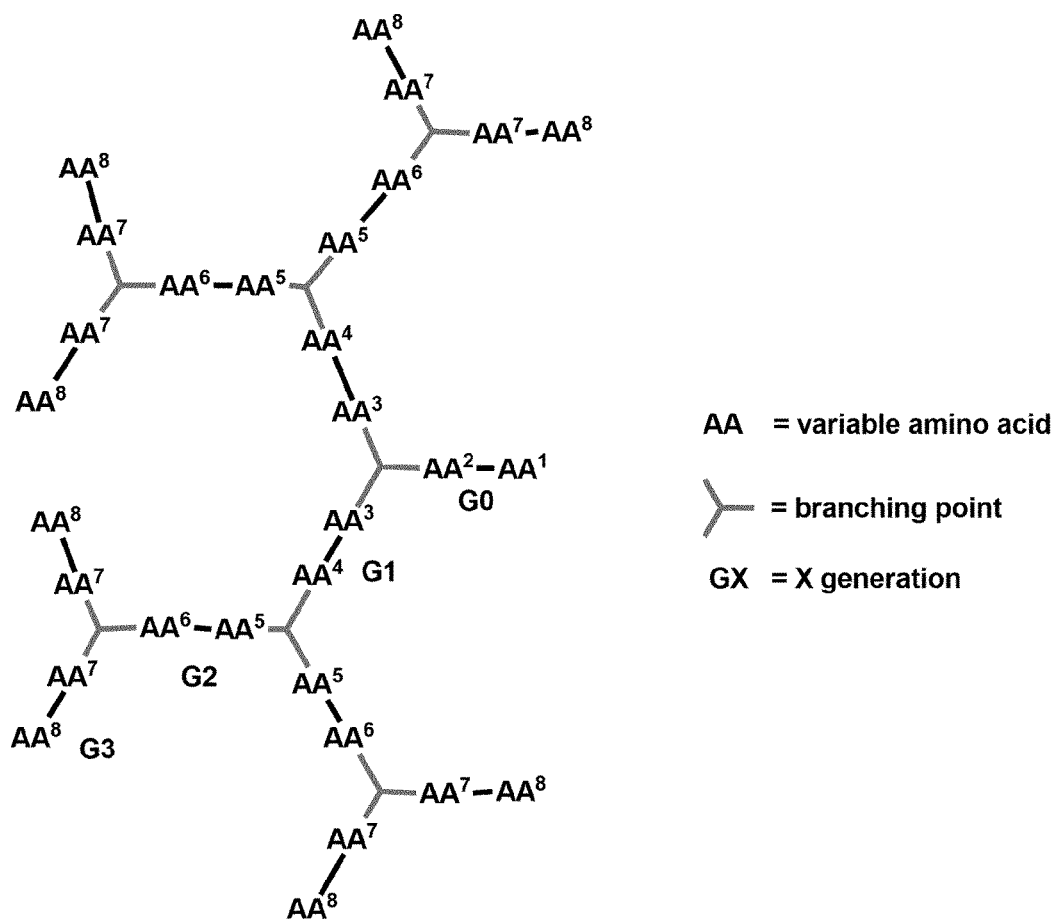

Specification includes a Sequence Listing.

(KL)₈(KKL)₄(KKL)₂(KKL)

A (KL)₄(KKL)₂(KKLKC₁₂)

B

A

B

A

B

A

B

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Linear synthetic peptide

<400> SEQUENCE: 1

Lys Tyr Lys Lys Ala Leu Lys Lys Leu Ala Lys Leu Leu
1               5                   10
```

```
<210> SEQ ID NO 2
<211> LENGTH: 14
<212> TYPE: PRT
<213> ORGANISM: Artificial Sequence
<220> FEATURE:
<223> OTHER INFORMATION: Linear synthetic peptide

<400> SEQUENCE: 2

Lys Leu Lys Leu Lys Leu Lys Leu Lys Leu Lys Leu Lys Leu
1               5                   10
```

ANTIMICROBIAL PEPTIDE DENDRIMERS

CROSS-REFERENCE TO RELATED APPLICATIONS

This is the U.S. National Stage of International Application No. PCT/EP2015/056819, filed Mar. 27, 2015, which was published in English under PCT Article 21(2), and which in turn claims the benefit of EP Patent Application No. 14162252.2, filed Mar. 28, 2014.

The Gram-negative *Pseudomonas aeruginosa* (*P. aeruginosa*) is a common opportunistic pathogen widely distributed in the environment. *P. aeruginosa* is often associated with infections of urinary tract, respiratory system, blood stream and in patients with serious burns and cystic fibrosis. In patients with extensive burns it can even cause systemic infections. *P. aeruginosa* is one of the main causes of mortality in hospital-acquired infections. This is due to high levels of acquired resistance to antibiotics and the formation of biofilms, which decrease the susceptibility to antibiotics. Therefore a need to develop new therapeutic agents targeting Gram negative bacteria and in particular *P. aeruginosa* exists.

Antimicrobial peptides (AMP) are produced in all forms of life as defence mechanism against competing pathogenic microbes. Linear AMPs are the largest group but also mono- and polycyclic AMPs can be found in nature. Common features for all AMPs are 6-50 residues with the basic amino acids Lys or Arg and a significant proportion (at least 30%) of hydrophobic residues. Therefore AMPs preferentially interact with the negatively charged bacterial over zwitterionic mammalian membranes and the hydrophobic residues facilitate the diffusion into the hydrophobic part of the membrane. Even with AMPs there is the potential to induce resistance, although the process is much slower than with classical antibiotics. Most linear AMPs have a broad spectrum of activity against pathogenic bacteria, fungi, viruses, parasites and even cancerous cells, which makes them excellent sources for new antibiotics. Potential toxicity, rapid degradation by proteases, susceptibility to pH change and high production cost are major drawbacks of linear AMPs.

Another class consists of multimeric/dendrimeric antimicrobial peptides. These peptide dendrimers were defined as branched polymers with several copies of peptide monomers attached to a template or core matrix. Numerous types of those multivalent peptide dendrimers were developed in the last 30 years. Modifications were mainly carried out at the core, whereas the attached peptides remained efficient natural occurring peptides or their analogues. In the 1980s multiple antigen peptides (MAPs) were introduced as immunogens with a core consisting of Lys as branching unit and giving dendrimers up to the third generation (Tam, J. P. et al.; 2002, Eur. J Biochem., 269, 923-32).

Peptide dendrimers with a new topology were developed in the academic group of the present inventors. These peptide dendrimers are branched peptides with diamino acids such as Lys used as branching point and one, two or three amino acids (AA) between the branching units. They are easily prepared by solid phase peptide synthesis and well soluble in aqueous media without propensity for aggregation as commonly found with linear sequences. Those peptide dendrimers demonstrate catalytic and biological activities and are very stable to proteolysis and hydrolysis compared to linear analogues.

Investigations into peptide dendrimers as antimicrobials was first attempted with the synthesis of a combinatorial library on beads of 1111 peptide dendrimers (with one amino acid between branching lysines) and screening for activity with a bead diffusion assay (Stach, M. et al., 2012. Med. Chem. Commun., 3(1), 86). *B subtilis* was used as screening bacterium and revealed several hit sequences. Resynthesis of hits and analogues gave compounds that were very active against the Gram positive *B subtilis*. All prepared compounds however showed either no activity against *P. aeruginosa* or were only slightly active, with a MIC (minimal inhibitory concentration) of about 20 µg/mL. Screening the same library with *P. aeruginosa* revealed no hit structures.

The objective of the present invention is to provide novel peptide antibiotics for use in vitro and in vivo. This objective is attained by the subject matter of the independent claims.

The present invention relates to a new class of antimicrobial peptide dendrimers (AMPDs) (FIG. 1), with 2 or 3 amino acids between the branching units. The peptide dendrimers can be second, third, fourth or fifth generational, branching units can be Lys, Dap, Orn or Dab and the amino acids between branching units are any natural or unnatural amino acid. Groups that increase activity, such as hydrophobic tails, can be attached to the core or N-termini of the dendrimers. Such peptide dendrimers are highly effective against the Gram-negative *P. aeruginosa*, including clinical isolates, other Gram-negative bacteria including *E. coli* and *A. Baumannii* and some Gram-positive bacteria (*S. aureus*).

Terms and Definitions

Amino acid sequences are given from N-termini to C-terminus. The terminal carboxy group of a peptide dendrimer mentioned herein may be a carboxylic acid, a carboxylate (COO—) or an amide ($CONH_2$) group.

An alkylcarboxylic acid in the context of the present specification is described by the general formula $CH_3(CH_2)_n COOH$, wherein n is a value from 6 to 22. In certain embodiments, n is selected from 6, 7, 8, 9, 10, 11, 12, 14 or 16.

Sequence positions given in the three-letter code (Stryer, Biochemistry, $3^{rd}$ ed. p. 21) refer to the naturally occurring (proteinogenic) L-amino acid enantiomers or diastereomers if not indicated otherwise.

A hydrophobic amino acid in the context of the present specification is any alpha-amino-carboxylic acid having a side chain without hydrogen bond donors or acceptors. Hydrophobic amino acids include, without being limited to, alanine, valine, isoleucine, leucine, methionine, phenylalanine, tyrosine and tryptophan.

An amino acid comprising a cationic side chain in the context of the present specification is an alpha-amino carboxylic acid having a side chain comprising a chemical functional group present as a cation under physiological pH. Cationic amino acids include, without being limited to, arginine, histidine, lysine, ornithine, diaminoproprionic acid and diaminobutyric acid.

Dab is (L)-2,3-diaminobutyric acid (CAS No. 2643-66-5).

(B) is (L)-2,3-diaminopropionic acid (CAS No. 4033-39-0).

SUMMARY OF THE INVENTION

According to a first aspect of the invention, a peptide dendrimer for use as a pharmaceutical is provided. This dendrimer is described by a general formula

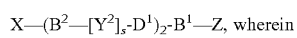, wherein

X is $(D^2)_4$, $(D^3)_8$-$(B^3$—$[Y^3]_r$-$D^2)_4$,

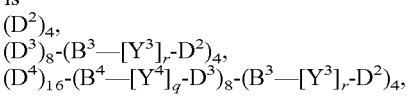

$(D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, or $(D^6)_{64}$-$(B^6$—$[Y^6]_o$-$D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, each Y ($Y^2$, $Y^3$, $Y^4$, $Y^5$ and $Y^6$) independently from any other Y is a linkage moiety di- or tripetide CH-Cys or H-Cys linked to the N-terminus of the C-terminally neighboring amino acid through a thioether moiety exemplified by the formula

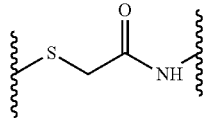

o, p, q, r and s can be 0 or 1;

Z is a central moiety;

each B ($B^1$, $B^2$, $B^3$, $B^4$, $B^5$ and $B^6$) independently from any other B is a branching moiety;

each D ($D^1$, $D^2$, $D^3$, $D^4$, $D^5$ and $D^6$) independently from any other D is
  i. a dipeptide CH, HC, CC or HH, or
  ii. a tripeptide HCH, HHC, CHH, CCH, CHC, HCC, HHH or CCC, wherein
  H is any amino acid comprising a hydrophobic side chain, and
  C is any amino acid comprising a cationic side chain.

In other words, the dendrimers that are subject of this invention are described by a condensed general formula:

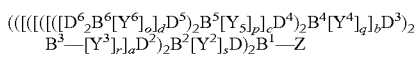

wherein a, b, c and d can be 0 or 1 (but b can only be 1 if a is 1, c can only be 1 if b is 1, and d can only be 1 if c is 1). The linkage moiety Y, where present, is connected to the neighboring D by thioether linkage of its cysteine side chain with an acetic acid moiety bound to D via an amide bond as depicted in the formula above. In this exemplary linkage, the sulphur in the thioether group originates from the cysteine side chain of Y and the amino group in the amide bond originates from the N-terminal amino acid of the C-terminally (from the point of view of the cysteine residue) neighboring D.

The branching moiety B, for all aspects of the invention, can be any bifunctional amino acid, particularly any diamino acid, particularly a diamino-substituted alkylcarboxylic acid moiety described by the general formula: $C_nH_{2n-1}(NH_2)_2$ CO—, wherein n is a number between 2 and 10, more particularly n is 2, 3, 4 or 5.

In some embodiments, the peptide dendrimer for use as a pharmaceutical is described by a general formula X—$(B^2$—$[Y^2]_s$-$D^1)_2$-$B^1$—Z, wherein X is
  $(D^2)_4$,
  $(D^3)_8$-$(B^3$—$[Y^3]_r$-$D^2)_4$,
  $(D^4)_{16}$-$(B^4$—$[Y^4]_q$-$D^3)_8$-$(B^3$—$[Y^3]_r$-$D^2)_4$,
  $(D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, or
  $(D^6)_{64}$-$(B^6$—$[Y^6]_o$-$D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, and wherein
each Y ($Y^2$, $Y^3$, $Y^4$, $Y^5$ and $Y^6$) independently from any other Y is a linkage moiety di- or tripetide H-Cys or CH-Cys linked to the N-terminus of the C-terminally neighboring amino acid in D through a thioether moiety exemplified by the formula

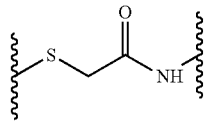 [SMILES: *NC(=O)CS*]

o, p, q, r and s is 0 or 1;

Z is a central moiety;

each B ($B^1$, $B^2$, $B^3$, $B^4$, $B^5$ and $B^6$) independently from any other B denotes a diaminoalkylcarboxylic acid moiety described by the general formula: $C_nH_{2n-1}(NH)_2$ CO— wherein n is a number between 2 and 10, more particularly n is 2, 3, 4 or 5 each D ($D^1$, $D^2$, $D^3$, $D^4$, $D^5$ and $D^6$) independently from any other D is
  i. a dipeptide CH, HC, CC or HH, or
  ii. a tripeptide HCH, HHC, CHH, CCH, CHC, HCC, HHH or CCC wherein
  H is any amino acid comprising a hydrophobic side chain, and
  C is any amino acid comprising a cationic side chain.

In some embodiments, the peptide dendrimer for use as a pharmaceutical is described by a general formula X—$(B^2$—$[Y^2]_s$-$D^1)_2$-$B^1$—Z, wherein X is
  $(D^2)_4$,
  $(D^3)_8$-$(B^3$—$[Y^3]_r$-$D^2)_4$,
  $(D^4)_{16}$-$(B^4$—$[Y^4]_q$-$D^3)_8$-$(B^3$—$[Y^3]_r$-$D^2)_4$,
  $(D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, or
  $(D^6)_{64}$-$(B^6$—$[Y^6]_o$-$D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, and wherein
each Y ($Y^2$, $Y^3$, $Y^4$, $Y^5$ and $Y^6$) independently from any other Y is a linkage moiety di- or tripetide H-Cys or CH-Cys linked to the N-terminus of the C-terminally neighboring amino acid in D through a thioether moiety exemplified by the formula

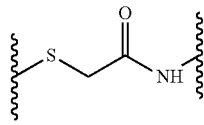 [SMILES: *NC(=O)CS*]

o, p, q, r and s is 0 or 1, wherein at least one of o, p, q, r and s is 1;

Z is a central moiety;

each B ($B^1$, $B^2$, $B^3$, $B^4$, $B^5$ and $B^6$) independently from any other B denotes a diaminoalkylcarboxylic acid moiety described by the general formula: $C_nH_{2n-1}(NH)_2$ CO— wherein n is a number between 2 and 10, more particularly n is 2, 3, 4 or 5 each D ($D^1$, $D^2$, $D^3$, $D^4$, $D^5$ and $D^6$) independently from any other D is
  i. a dipeptide CH, HC, CC or HH, or
  ii. a tripeptide HCH, HHC, CHH, CCH, CHC, HCC, HHH or CCC wherein
H is any amino acid comprising a hydrophobic side chain, and
C is any amino acid comprising a cationic side chain.

In some embodiments, the peptide dendrimer for use as a pharmaceutical is described by a general formula

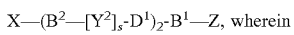

X is
(D$^2$)$_4$,
(D$^3$)$_8$-(B$^3$—[Y$^3$]$_r$-D$^2$)$_4$,
(D$^4$)$_{16}$-(B$^4$—[Y$^4$]$_q$-D$^3$)$_8$-(B$^3$—[Y$^3$]$_r$-D$^2$)$_4$,
(D$^5$)$_{32}$-(B$^5$—[Y$^5$]$_p$-D$^4$)$_{16}$-(B$^4$—[Y$^4$]$_q$-D$^3$)$_8$-(B$^3$—[Y$^3$]$_r$-D$^2$)$_4$, or
(D$^6$)$_{64}$-(B$^6$—[Y$^6$]$_o$-D$^5$)$_{32}$-(B$^5$—[Y$^5$]$_p$-D$^4$)$_{16}$-(B$^4$—[Y$^4$]$_q$-D$^3$)$_8$-(B$^3$—[Y$^3$]$_r$-D$^2$)$_4$, and wherein
each Y (Y$^2$, Y$^3$, Y$^4$, Y$^5$ and Y$^6$) independently from any other Y is a linkage moiety di- or tripeptide H-Cys or CH-Cys linked to the N-terminus of the C-terminally neighboring amino acid in D through a thioether moiety exemplified by the formula

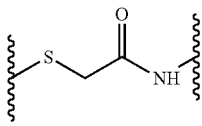

o, p, q, r and s is 0 or 1;
Z is a central moiety;
each B (B$^1$, B$^2$, B$^3$, B$^4$, B$^5$ and B$^6$) independently from any other B denotes a diaminoalkylcarboxylic acid moiety described by the general formula: C$_n$H$_{2n-1}$(NH)$_2$CO— wherein n is a number between 2 and 10, more particularly n is 2, 3, 4 or 5
each D (D$^1$, D$^2$, D$^3$, D$^4$, D$^5$ and D$^6$) independently from any other D is
i. a dipeptide CH, HC, CC or HH, or
ii. a tripeptide HCH, HHC, CHH, CCH, CHC, HCC, HHH or CCC,
wherein at least one D$^1$, D$^2$, D$^3$, D$^4$, D$^5$ and D$^6$ is a tripeptide selected from the above mentioned tripeptides,
wherein
H is any amino acid comprising a hydrophobic side chain, and
C is any amino acid comprising a cationic side chain.

The following embodiments for B apply to all aspects of the invention. In some embodiments, B is an amino-functionalized alpha-amino acid such as lysine, ornithine, 2,3-diaminobutyric acid and 2,3-diaminoproprionic acid. In some embodiments, B is an amino acid selected from naturally occurring amino acids. Naturally occurring amino acids are easily metabolized to non-toxic metabolites, thus facilitating regulatory approval of the dendrimer for use in human beings.

In certain embodiments of any aspect of this invention, the peptide dendrimer is synthesized by solid phase peptide synthesis according to Merrifield, extending the dendrimer through peptide coupling of an activated carboxylic acid group to the amino group of the growing dendrimer on the solid phase support. In some such embodiments of any aspect of this invention, the first position Z is linked to B via an amide bond between an amino function on Z to a carboxylic acid carbon on B$^1$, and each of D$^1$, D$^2$, D$^3$, D$^4$, D$^5$, D$^6$ is linked to its respective binding partner B$^1$, B$^2$, B$^3$, B$^4$, B$^5$, B$^6$ via an amide bond between an amino nitrogen on B$^1$, B$^2$, B$^3$B$^4$B$^5$, B$^6$ to a carboxylic acid carbon on the carboxyl terminal amino acid of D$^1$, D$^2$, D$^3$ D$^4$, D$^5$, D$^6$, respectively.

For embodiments wherein no thioether link is present ( ), the formula can be expressed in simplified form:

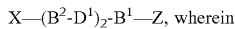

X is
(D$^2$)$_4$,
(D$^3$)$_8$-(B$^3$-D$^2$)$_4$,
(D$^4$)$_{16}$-(B$^4$-D$^3$)$_8$-(B$^3$-D$^2$)$_4$,
(D$^5$)$_{32}$-(B$^5$-D$^4$)$_{16}$-(B$^4$-D$^3$)$_8$-(B$^3$-D$^2$)$_4$, or
(D$^6$)$_{64}$-D$^5$)$_{32}$-(B$^5$-D$^4$)$_{16}$-(B$^4$-D$^3$)$_8$-(B$^3$-D$^2$)$_4$,

In certain embodiments, each D$^1$, D$^2$, D$^3$, D$^4$, D$^5$, and D$^6$ independently from any other D is a dipeptide (CH, HC, CC or HH) or a tripeptide (HCH, HHC, CHH, CCH, CHC, HCC, HHH or CCC).

Z is the central moiety and, in solid phase chemistry methods for making the dendrimer of the invention, Z is the starting point of synthesis. A number of different short peptides have been employed experimentally, with overall good success.

In some embodiments, Z is Lys-Leu, Arg-Leu, Dab-Trp, Dab-Leu, Leu-Lys, Lys-Trp, Lys-Phe, Lys-Lys, Leu-Leu, DabA-Ala, Lys-Lys-Leu, Lys-Leu-Leu, Leu-Lys-Leu, Lys-Leu-Lys, Orn-Leu, Orn-Phe, Arg-Phe or Gly-Ser-Cys.

In some embodiments, Z is Lys-Leu-Lys (CONH$_2$). In some embodiments, Z is Lys-Leu, Arg-Leu, Dab-Leu or Dab-Trp. In some embodiments, Z is Lys or Leu. In some embodiments, Z is coupled to an alkylcarboxylic acid via an amide bond between an amino function on Z to the carboxyl group on the alkylcarboxylic acid. In certain embodiments, the alkylcarboxylic acid is linked to the omega amino side chain of a lysine moiety comprised in Z. In other embodiments the alkylcarboxylic acid is linked to an N-terminal D.

In some embodiments H is selected from leucine, phenylalanine, alanine, tyrosine or tryptophan. In some embodiments C is selected from lysine, arginine or (L)-2-3-diaminobutyric acid.

In some embodiments, Z is a tripeptide HCH, HHC, CHH, CCH, CHC, HCC, HHH or CCC with H and C having the meaning defined above.

In some embodiments, Z is Lys-Leu-Lys.

In some embodiments, Z is a tripeptide HCH, HHC, CHH, CCH, CHC, HCC, HHH or CCC with H and C having the meaning defined above and, Z is coupled to an alkylcarboxylic acid described by a general formula CH$_3$(CH$_2$)$_n$CO— via an amide bond between an amino function on Z to the carboxyl group on the alkylcarboxylic acid.

In some embodiments, n is a number between 4 and 22, particularly between 4 to 10, more particularly between 4 to 8.

In some embodiments, Z is Lys-Leu-Lys, Z is coupled to an alkylcarboxylic acid via an amide bond between an amino function on Z to the carboxyl group on the alkylcarboxylic acid.

In some embodiments the peptide dendrimer is characterized by the formulae of table 1a:

TABLE 1a

| | |
|---|---|
| a. | (KL)$_4$-(K-KL)$_2$-K-KL |
| b. | (KL)$_4$-(B-KL)$_2$-B-KL |
| c. | (RL)$_4$-(B-RL)$_2$-B-RL |
| d. | (KKL)$_4$-(K-KL)$_2$K-KL |

TABLE 1a-continued

| | |
|---|---|
| e. | (DabW)$_4$-(K-DabW)$_2$-K-DabW |
| f. | (DabL)$_4$-(K-DabL)$_2$-K-DabL |
| g. | (KL)$_8$-(K-KL)$_4$-(K-KL)$_2$-K-KL |
| h. | (RL)$_8$-(K-RL)$_4$(K-RL)$_2$-K-RL |
| i. | (LK)$_8$-(K-LK)$_4$-(K-LK)$_2$-K-LK |
| j. | (KY)$_8$-(K-KL)$_4$-(K-KL)$_2$-K-KL |
| k. | (LA)$_8$-(K-LK)$_4$-(K-LA)$_2$-K-KL |
| l. | (KW)$_8$-(K-KW)$_4$-(K-KW)$_2$-K-KW |
| m. | (KF)$_8$-(K-KF)$_4$-(K-KF)$_2$-K-KF |
| n. | (KL)$_8$-(B-KL)$_4$-(B-KL)$_2$-B-KL |
| o. | (RL)$_8$-(B-RL)$_4$-(B-RL)$_2$-B-RL |
| p. | (LL)$_8$-(K-KL)$_4$-(K-LL)$_2$-K-KK |
| q. | (DabL)$_8$-(K-DabL)$_4$-(K-DabL)$_2$-K-DabL |
| r. | (DabL)$_8$-(K-DabW)$_4$-(K-DabL)$_2$-K-DabW |
| s. | (DabL)$_8$-(K-DabL)$_4$-(K-DabW)$_2$-K-DabW |
| t. | (DabL)$_8$-(K-DabW)$_4$-(K-DabW)$_2$-K-DabL |
| u. | (DabL)$_8$-(K-DabW)$_4$-(K-DabW)$_2$-K-DabA |
| v. | (DabL)$_8$-(K-DabW)$_4$-(K-DabA)$_2$-K-DabW |
| w. | (DabL)$_8$-(K-DabA)$_4$-(K-DabW)$_2$-K-DabW |
| x. | (KL)$_8$-(K-KLCKL)$_4$-(K-KL)$_2$-K-KL |
| y. | (KL)$_{16}$-(K-KLCKL)$_4$-(K-KL)$_2$-K-KL |
| z. | (KL)$_{16}$-(K-KLCKL)$_8$-(K-KL)$_4$-(K-KL)$_2$-K-KL |
| aa. | (RL)$_8$-(K-RLCRL)$_4$-(K-RL)$_2$-K-RL |
| bb. | (KKL)$_4$-(K-KKL)$_2$-K-KKL |
| cc. | (KLL)$_4$-(K-KLL)$_2$-K-KLL |
| dd. | (LKL)$_4$-(K-LKL)$_2$-K-LKL |
| ee. | (KLL)$_8$-(K-KLL)$_4$-(K-KLL)$_2$-K-KLL |
| ff. | (LKL)$_8$-(K-LKL)$_4$-(K-LKL)$_2$-K-LKL |
| gg. | (KL)$_8$-(K-KL)$_4$-(K-LKL)$_2$-K-KKL |
| hh. | (KL)$_8$-(K-KL)$_4$-(K-LKL)$_2$-K-KLL |
| ii. | (KL)$_8$-(K-KL)$_4$-(K-LKL)$_2$-K-KLK |
| jj. | (KL)$_8$-(K-KL)$_4$-(K-LKL)$_2$-K-LKL |
| kk. | (KL)$_4$-(K-KL)$_2$-K-KLK-(CO(CH$_2$)$_4$CH$_3$ |
| ll. | (KL)$_4$-(K-KL)$_2$-K-KLK-(CO(CH$_2$)$_6$CH$_3$ |
| mm. | (KL)$_4$-(K-KL)$_2$-K-KLK-(CO(CH$_2$)$_8$CH$_3$ |
| nn. | (KL)$_4$-(K-KL)$_2$-K-KLK-(CO(CH$_2$)$_{10}$CH$_3$ |
| oo. | (KL)$_8$-(K-KL)$_4$-(K-KL)$_2$-K-KLK-(CO(CH$_2$)$_4$CH$_3$ |
| pp. | (KL)$_8$-(K-KL)$_4$-(K-KL)$_2$-K-KLK-(CO(CH$_2$)$_6$CH$_3$ |
| qq. | (KL)$_8$-(K-KL)$_4$-(K-KL)$_2$-K-KLK-(CO(CH$_2$)$_8$CH$_3$ |
| rr. | (KL)$_8$-(K-KL)$_4$-(K-KL)$_2$-K-KLK-(CO(CH$_2$)$_{10}$CH$_3$ |
| ss. | (KL)$_8$-(K-KL)$_4$-(K-KL)$_2$-K-KLK-(CO(CH$_2$)$_{14}$CH$_3$ |
| tt. | (KL)$_8$-(K-KL)$_4$-(K-KL)$_2$-K-KLK-(CO(CH$_2$)$_{16}$CH$_3$ |
| uu. | (KL)$_8$-(K-KL)$_4$-(K-KL)$_2$-K-KLK-(CO(CH$_2$)$_{22}$CH$_3$ |
| vv. | (KL)$_4$-(K-KL)$_2$-K-KLK-(CO(CH$_2$)$_{16}$CH$_3$ |
| ww. | (CH$_3$(CH$_2$)$_4$CO-KL)$_8$-(K-KL)$_4$-(K-KL)$_2$-K-KL |
| xx. | (CH$_3$(CH$_2$)$_4$CO-KL)$_4$-(K-KL)$_2$-K-KL |
| yy. | (KK)$_8$-(K-KK)$_4$-(K-LL)$_2$-K-LL |
| zz. | (KK)$_8$-(K-LL)$_4$-(K-KK)$_2$-K-LL |
| aaa. | (KL)$_4$-(K-KL)$_2$-K-KLK-(CO(CH$_2$)$_{14}$CH$_3$ |
| bbb. | (KL)$_4$-(K-KL)$_2$-K-KLK-(CO(CH$_2$)$_{22}$CH$_3$ |

In some embodiments, compounds g and
h are excluded from the list.
In some embodiments, the list of table
1a further comprises the compounds

| | |
|---|---|
| ccc. | (KK)$_8$-(K-LL)$_4$-(K-LL)$_2$-K-GSC |
| ddd. | (KK)$_8$-(K-KK)$_4$-(K-LL)$_2$-K-GSC |
| eee. | (KK)$_8$-(K-KK)$_4$-(K-KK)$_2$-K-GSC |
| fff. | (KL)$_8$-(K-LL)$_4$-(K-LL)$_2$-K-GSC |
| ggg. | (KL)$_8$-(K-KL)$_4$-(K-LL)$_2$-K-GSC |
| hhh. | (KL)$_8$-(K-KL)$_4$-(K-LL)$_2$-K-GSC |
| iii. | (KA)$_8$-(K-KA)$_4$-(K-KA)$_2$-K-GSC |
| jjj. | (KH)$_8$-(K-KH)$_4$-(K-KH)$_2$-K-GSC |
| kkk. | (RL)$_8$-(K-LL)$_4$-(K-LL)$_2$-K-GSC |
| lll. | (RL)$_8$-(K-RL)$_4$-(K-LL)$_2$-K-GSC |
| mmm. | (RL)$_8$-(K-RL)$_4$-(K-RL)$_2$-K-GSC |

In some embodiments, the list of table
1a further comprises the compounds

| | |
|---|---|
| nnn. | (OrnL)$_4$-(K-DabF)$_2$-K-KL |
| ooo. | (OrnF)$_4$-(K-DabL)$_2$-K-KL |
| ppp. | (RF)$_4$-(K-DabL)$_2$-K-KL |
| qqq. | (OrnF)$_4$-(K-DabL)$_2$-K-KLK-(CO(CH$_2$)$_8$CH$_3$ |
| rrr. | (OrnL)$_4$-(K-DabF)$_2$-K-KLK-(CO(CH$_2$)$_8$CH$_3$ |
| sss. | (RF)$_4$-(K-DabL)$_2$-K-KLK-(CO(CH$_2$)$_8$CH$_3$ |

Within each bracket, the leftmost (N-terminal) amino acid is the branching moiety, with the exception of the last one. In the examples given, the single amino acid between the bracketed parts and the moiety Z is the branching moiety.

In certain embodiments, the peptide dendrimer for use as a pharmaceutical according to this first aspect of the invention is characterized by an alkylcarboxylic acid moiety being covalently linked to Z and/or an N-terminal D of the dendrimer, particularly an alkylcarboxylic acid moiety described by a general formula $CH_3(CH_2)_nCO-$, more particularly wherein n is a number between 4 and 22, even more particularly n is 4, 5, 6, 7, 8, 9, 10, 11, 12, 14 or 16.

In certain embodiments, the dendrimer is present as a (homo-) dimer. The dimerization is achieved, for example, by linking two dendrimers through a cysteine residue in the Z central moiety.

In certain embodiments the peptide dendrimer is used for the prevention or therapy of bacterial infection. In certain embodiments, said bacterial infection is caused by gram negative or positive bacteria including but not limited to *Pseudomonas aeruginosa, Acinetobacter baumannii* or *Escherichia coli*, or *Staphylococcus aureus*, particularly methicillin-resistant *S. aureus* (MRSA strain).

According to a second aspect of the invention, a peptide dendrimer described by a general formula

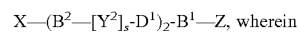

X is
(D$^2$)$_4$,
(D$^3$)$_8$-(B$^3$—[Y$^3$]$_r$-D$^2$)$_4$,
(D$^4$)$_{16}$-(B$^4$—[Y$^4$]$_q$-D$^3$)$_8$-(B$^3$—[Y$^3$]$_r$-D$^2$)$_4$,
(D$^5$)$_{32}$-(B$^5$—[Y$^5$]$_p$-D$^4$)$_{16}$-(B$^4$—[Y$^4$]$_q$-D$^3$)$_8$-(B$^3$—[Y$^3$]$_r$-D$^2$)$_4$, or
(D$^6$)$_{64}$-(B$^6$—[Y$^6$]$_o$-D$^5$)$_{32}$-(B$^5$—[Y$^5$]$_p$-D$^4$)$_{16}$-(B$^4$—[Y$^4$]$_q$-D$^3$)$_8$-(B$^3$—[Y$^3$]$_r$-D$^2$)$_4$, each Y (Y$^2$, Y$^3$, Y$^4$, Y$^5$ and Y$^6$) independently from any other Y is a linkage moiety di- or tripetide CH-Cys or H-Cys linked to the N-terminus of the C-terminally neighboring amino acid through a thioether moiety exemplified by the formula

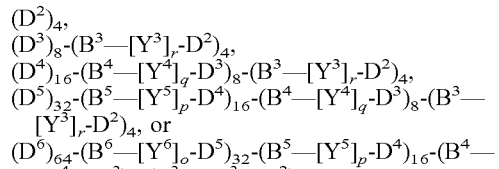

o, p, q, r and s can be 0 or 1;
Z is a central moiety;
each B (B$^1$, B$^2$, B$^3$, B$^4$, B$^5$ and B$^6$) independently from any other B is a branching moiety;
each D (D$^1$, D$^2$, D$^3$, D$^4$, D$^5$ and D$^6$) independently from any other D is
  i. a dipeptide CH, HC, CC or HH, or
  ii. a tripeptide HCH, HHC, CHH, CCH, CHC, HCC, HHH or CCC,
wherein
  H is any amino acid comprising a hydrophobic side chain, and
  C is (L)-2,3-diaminobutyric acid.

In some embodiments the peptide dendrimer described by a general formula

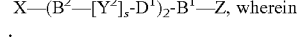

X is
(D$^2$)$_4$,
(D$^3$)$_8$-(B$^3$—[Y$^3$]$_r$-D$^2$)$_4$,
(D$^4$)$_{16}$-(B$^4$—[Y$^4$]$_q$-D$^3$)$_8$-(B$^3$—[Y$^3$]$_r$-D$^2$)$_4$, $(D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, or $(D^6)_{64}$-$(B^6$—$[Y^6]_o$-$D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, and wherein each Y ($Y^2$, $Y^3$, $Y^4$, $Y^5$ and $Y^6$) independently from any other Y is a linkage moiety di- or tripeptide H-Cys or CH-Cys linked to the N-terminus of the C-terminally neighboring amino acid in D through a thioether moiety exemplified by the formula

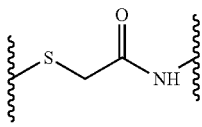

o, p, q, r and s can be 0 or 1;

Z is a central moiety;

each $B^1$, $B^2$, $B^3$, $B^4$, $B^5$ and $B^6$ independently from any other B denotes a diaminoalkylcarboxylic acid moiety described by the general formula: $C_nH_{2n-1}(NH)_2CO$— wherein n is a number between 2 and 10, more particularly n is 2, 3, 4 or 5 each $D^1$, $D^2$, $D^3$, $D^4$, $D^5$ and $D^6$ independently from any other D is
  i. a dipeptide CH, HC, CC or HH, or
  ii. a tripeptide HCH, HHC, CHH, CCH, CHC, HCC, HHH or CCC
wherein
  H is any amino acid comprising a hydrophobic side chain, and characterized in that
  C is (L)-2,3-diaminobutyric acid.

In some embodiments the peptide dendrimer described by a general formula

X—$(B^2$—$[Y^2]_s$-$D^1)_2$-$B^1$—Z, wherein

X is
  $(D^2)_4$,
  $(D^3)_8$-$(B^3$—$[Y^3]_r$-$D^2)_4$,
  $(D^4)_{16}$-$(B^4$—$[Y^4]_q$-$D^3)_8$-$(B^3$—$[Y^3]_r$-$D^2)_4$,
  $(D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, or
  $(D^6)_{64}$-$(B^6$—$[Y^6]_o$-$D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, and wherein each Y ($Y^2$, $Y^3$, $Y^4$, $Y^5$ and $Y^6$) independently from any other Y is a linkage moiety di- or tripeptide H-Cys or CH-Cys linked to the N-terminus of the C-terminally neighboring amino acid in D through a thioether moiety exemplified by the formula

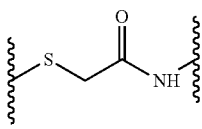

o, p, q, r and s can be 0 or 1;

Z is a central moiety;

each $B^1$, $B^2$, $B^3$, $B^4$, $B^5$ and $B^6$ independently from any other B denotes a diaminoalkylcarboxylic acid moiety described by the general formula: $C_nH_{2n-1}(NH)_2CO$— wherein n is a number between 2 and 10, more particularly n is 2, 3, 4 or 5 each $D^1$, $D^2$, $D^3$, $D^4$, $D^5$ and $D^6$ independently from any other D is
  iii. a dipeptide CH, HC, CC or HH, or
  iv. a tripeptide HCH, HHC, CHH, CCH, CHC, HCC, HHH or CCC
wherein
  H is any amino acid comprising a hydrophobic side chain, and characterized in that
  C is (L)-2,3-diaminobutyric acid and at least one of $D^1$, $D^2$, $D^3$, $D^4$, $D^5$ and $D^6$ is selected from CH, HC, CC, HCH, HHC, CHH, CCH, CHC, HCC or CCC.

In some embodiments, Z is Lys-Leu, Arg-Leu, Dab-Trp, Dab-Leu, Leu-Lys, Lys-Trp, Lys-Phe, Lys-Lys, Leu-Leu, DabA-Ala, Lys-Lys-Leu, Lys-Leu-Leu, Leu-Lys-Leu Lys-Leu-Lys, Orn-Leu, Orn-Phe, Arg-Phe or Gly-Ser-Cys.

Z is the central moiety and, in solid phase chemistry methods for making the dendrimer of the invention, Z is the starting point of synthesis. A number of different short peptides have been employed experimentally, with overall good success. In some embodiments, Z is Lys-Leu-Lys ($CONH_2$). In some embodiments, Z is Lys-Leu, Arg-Leu Dab-Leu or Dab-Trp. In some embodiments, Z is Lys or Leu.

In some embodiments H is selected from tryptophan, leucine or alanine. In some embodiments C is (L)-2-3-diaminobutyric acid.

In some embodiments, Z is a tripeptide HCH, HHC, CHH, CCH, CHC, HCC, HHH or CCC with H and C having the meaning defined above.

In some embodiments, Z is Lys-Leu-Lys.

In some embodiments, Z is a tripeptide HCH, HHC, CHH, CCH, CHC, HCC, HHH or CCC with H and C having the meaning defined above and, Z is coupled to an alkyl-carboxylic acid described by a general formula $CH_3(CH_2)_n$CO— via an amide bond between an amino function on Z to the carboxyl group on the alkylcarboxylic acid.

In some embodiments, n is a number between 4 and 22, particularly between 4 to 10, more particularly between 4 to 8.

In some embodiments, Z is Lys-Leu-Lys, Z is coupled to an alkylcarboxylic acid via an amide bond between an amino function on Z to the carboxyl group on the alkylcarboxylic acid.

According to a third aspect of the invention, a peptide dendrimer described by a general formula X—$(B^2$—$[Y^2]_s$-$D^1)_2$-$B^1$—Z, wherein X is
  $(D^2)_4$,
  $(D^3)_8$-$(B^3$—$[Y^3]_r$-$D^2)_4$,
  $(D^4)_{16}$-$(B^4$—$[Y^4]_q$-$D^3)_8$-$(B^3$—$[Y^3]_r$-$D^2)_4$,
  $(D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, or
  $(D^6)_{64}$-$(B^6$—$[Y^6]_o$-$D^5)_{32}$-$(B^5$—$[Y^5]_p$-$D^4)_{16}$-$(B^4$—$[Y^4]_q$-$D^3)_8$-$(B^3$—$[Y^3]_r$-$D^2)_4$, each Y (Y2, Y3, Y4, Y5 and Y6) independently from any other Y is a linkage moiety di- or tripeptide CH-Cys or H-Cys linked to the N-terminus of the C-terminally neighbouring amino acid through a thioether moiety exemplified by the formula

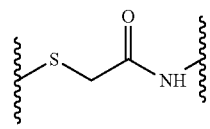 [SMILES: *NC(=O)CS*]

o, p, q, r and s can be 0 or 1;

Z is a central moiety;

each B ($B^1$, $B^2$, $B^3$, $B^4$, $B^5$ and $B^6$) independently from any other B is a branching moiety;

each D ($D^1$, $D^2$, $D^3$, $D^4$, $D^5$ and $D^6$) independently from any other D is
  i. an amino acid C or H,
  ii. a dipeptide CH, HC, CC or HH, or
  iii. a tripeptide HCH, HHC, CHH, CCH, CHC, HCC, HHH or CCC,
wherein
  H is any amino acid comprising a hydrophobic side chain, and
  C is any amino acid comprising a cationic side chain,
  and wherein characterized in that
Z and/or an N-terminal D is coupled to an alkylcarboxylic acid moiety described by a general formula $CH_3(CH_2)_nCO-$, particularly wherein n is a number between 6 and 22, more particularly n is 6, 7, 8, 9, 10, 11, 12, 14 or 16.

In some embodiments, the peptide dendrimer described by a general formula

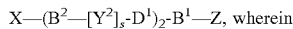

X is
  $(D^2)_4$,
  $(D^3)_8-(B^3-[Y^3]_r-D^2)_4$,
  $(D^4)_{16}-(B^4-[Y^4]_q-D^3)_8-(B^3-[Y^3]_r-D^2)_4$,
  $(D^5)_{32}-(B^5-[Y^5]_p-D^4)_{16}-(B^4-[Y^4]_q-D^3)_8-(B^3-[Y^3]_r-D^2)_4$, or
  $(D^6)_{64}-(B^6-[Y^6]_o-D^5)_{32}-(B^5-[Y^5]_p-D^4)_{16}-(B^4-[Y^4]_q-D^3)_8-(B^3-[Y^3]_r-D^2)_4$, each Y ($Y^2$, $Y^3$, $Y^4$, $Y^5$ and $Y^6$) independently from any other Y is a linkage moiety di- or tripeptide H-Cys or CH-Cys linked to the N-terminus of the C-terminally neighboring amino acid in D through a thioether moiety exemplified by the formula

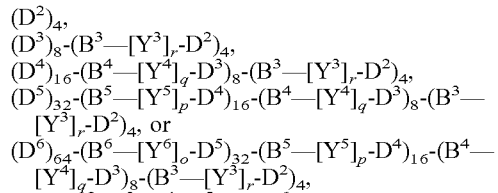

o, p, q, r and s is or 1;
Z is a central moiety;
each $B^1$, $B^2$, $B^3$, $B^4$, $B^5$ and $B^6$ independently from any other B denotes a diaminoalkylcarboxylic acid moiety described by the general formula: $C_nH_{2n-1}(NH_2)_2CO-$ wherein n is a number between 2 and 10, more particularly n is 2, 3, 4 or 5
each $D^1$, $D^2$, $D^3$, $D^4$, $D^5$ and $D^6$ independently from any other D is
  i. an amino acid C or H
  ii. a dipeptide CH, HC, CC or HH
  iii. a tripeptide HCH, HHC, CHH, CCH, CHC, HCC, HHH or CCC
wherein
  H is any amino acid comprising a hydrophobic side chain, and
  C is any amino acid comprising a cationic side chain, characterized in that
Z and/or an N-terminal D is coupled to an alkylcarboxylic acid.

In some embodiments, Z and/or an N-terminal D is coupled to an alkylcarboxylic acid moiety described by a general formula $CH_3(CH_2)_nCO-$, particularly wherein n is a number between 6 and 22, more particularly n is 6, 7, 8, 9, 10, 11, 12, 14 or 16

In some embodiments, n is a number between 4 and 22, particularly between 4 to 10, more particularly between 4 to 8.

In some embodiments, Z is Lys-Leu, Arg-Leu, Dab-Trp, Dab-Leu, Leu-Lys, Lys-Trp, Lys-Phe, Lys-Lys, Leu-Leu, DabA-Ala, Lys-Lys-Leu, Lys-Leu-Leu, Leu-Lys-Leu Lys-Leu-Lys, Orn-Leu, Orn-Phe, Arg-Phe or Gly-Ser-Cys.

In some embodiments, Z is a tripeptide HCH, HHC, CHH, CCH, CHC, HCC, HHH or CCC with H and C having the meaning defined above.

In some embodiments, Z is Lys-Leu-Lys.

In some embodiments, Z is a tripeptide HCH, HHC, CHH, CCH, CHC, HCC, HHH or CCC with H and C having the meaning defined above and, Z is coupled to an alkylcarboxylic acid described by a general formula $CH_3(CH_2)_nCO-$ via an amide bond between an amino function on Z to the carboxyl group on the alkylcarboxylic acid.

In some embodiments, n is a number between 4 and 22, particularly between 4 to 10, more particularly between 4 to 8.

In some embodiments, Z is Lys-Leu-Lys, Z is coupled to an alkylcarboxylic acid via an amide bond between an amino function on Z to the carboxyl group on the alkylcarboxylic acid.

Z is the central moiety and, in solid phase chemistry methods for making the dendrimer of the invention, Z is the starting point of synthesis. In some embodiments, Z is Lys-Leu-Lys ($CONH_2$).

In some embodiments H is selected from leucine, phenylalanine, alanine, tyrosine or tryptophan. In some embodiments C is selected from lysine, arginine or (L)-2,3-diaminobutyric acid.

In some embodiments the peptide dendrimer is characterized by the formulae shown in Table 1 excluding formulae g and h.

In certain embodiments of any aspect of the invention disclosed herein, the dendrimer is composed entirely or partially of D enantiomers of the amino acids specified above.

Wherever alternatives for single separable features such as, for example, any of $D^1$, $D^2$, $D^3$, $D^4$, $D^5$ or $D^6$, $B^1$, $B^2$, $B^3$, $B^4$, $B^5$ or $B^6$, or Z or H, or C, are laid out herein as "embodiments", it is to be understood that such alternatives may be combined freely to form discrete embodiments of the invention disclosed herein.

In some embodiments the peptide dendrimer is characterized by the formulae of table 1b:

TABLE 1b

| | |
|---|---|
| a. | $(KL)_4-(K-KL)_2-K-KL$ |
| b. | $(KL)_4-(B-KL)_2-B-KL$ |
| c. | $(RL)_4-(B-RL)_2-B-RL$ |
| d. | $(KKL)_4-(K-KL)_2-K-KL$ |
| e. | $(DabW)_4-(K-DabW)_2-K-DabW$ |
| f. | $(DabL)_4-(K-DabL)_2-K-DabL$ |
| g. | $(LK)_8-(K-LK)_4-(K-LK)_2-K-LK$ |
| h. | $(KY)_8-(K-KL)_4-(K-KL)_2-K-KL$ |
| i. | $(LA)_8-(K-KL)_4-(K-LA)_2-K-KL$ |
| j. | $(KW)_8-(K-KW)_4-(K-KW)_2-K-KW$ |
| k. | $(KF)_8-(K-KF)_4-(K-KF)_2-K-KF$ |
| l. | $(KL)_8-(B-KL)_4-(B-KL)_2-B-KL$ |
| m. | $(RL)_8-(B-RL)_4-(B-RL)_2-B-RL$ |
| n. | $(LL)_8-(K-KK)_4-(K-LL)_2-K-KK$ |
| o. | $(DabL)_8-(K-DabL)_4-(K-DabL)_2-K-DabL$ |
| p. | $(DabL)_8-(K-DabW)_4-(K-DabL)_2-K-DabW$ |
| q. | $(DabL)_8-(K-DabL)_4-(K-DabW)_2-K-DabW$ |
| r. | $(DabL)_8-(K-DabW)_4-(K-DabW)_2-K-DabL$ |
| s. | $(DabL)_8-(K-DabW)_4-(K-DabW)_2-K-DabA$ |
| t. | $(DabL)_8-(K-DabW)_4-(K-DabA)_2-K-DabW$ |

TABLE 1b-continued

| | |
|---|---|
| u. | (DabL)$_8$-(K-DabA)$_4$-(K-DabW)$_2$-K-DabW |
| v. | (KL)$_8$-(K-KLCKL)$_4$-(K-KL)$_2$-K-KL |
| w. | (KL)$_{16}$-(K-KL)$_8$-(K-KLCKL)$_4$-(K-KL)$_2$-K-KL |
| x. | (KL)$_{16}$-(K-KLCKL)$_8$-(K-KL)$_4$-(K-KL)$_2$-K-KL |
| y. | (RL)$_8$-(K-RLCRL)$_4$-(K-RL)$_2$-K-RL |
| z. | (KKL)$_4$-(K-KKL)$_2$-K-KKL |
| aa. | (KLL)$_4$-(K-KLL)$_2$-K-KLL |
| bb. | (LKL)$_4$-(K-LKL)$_2$-K-LKL |
| cc. | (KLL)$_8$-(K-KLL)$_4$-(K-KLL)$_2$-K-KLL |
| dd. | (LKL)$_8$-(K-LKL)$_4$-(K-LKL)$_2$-K-LKL |
| ee. | (KL)$_8$-(K-KL)$_4$-(K-LKL)$_2$-K-KKL |
| ff. | (KL)$_8$-(K-KL)$_4$-(K-LKL)$_2$-K-KLL |
| gg. | (KL)$_8$-(K-KL)$_4$-(K-LKL)$_2$-K-KLK |
| hh. | (KL)$_8$-(K-KL)$_4$-(K-LKL)$_2$-K-LKL |
| ii. | (KL)$_4$-(K-KL)$_2$-K-KLK-(CO(CH$_2$)$_4$CH$_3$ |
| jj. | (KL)$_4$-(K-KL)$_2$-K-KLK-(CO(CH$_2$)$_6$CH$_3$ |
| kk. | (KL)$_4$-(K-KL)$_2$-K-KLK-(CO(CH$_2$)$_8$CH$_3$ |
| ll. | (KL)$_4$-(K-KL)$_2$-K-KLK-(CO(CH$_2$)$_{10}$CH$_3$ |
| mm. | (KL)$_8$-(K-KL)$_4$-(K-KL)$_2$-K-KLK-(CO(CH$_2$)$_4$CH$_3$ |
| nn. | (KL)$_8$-(K-KL)$_4$-(K-KL)$_2$-K-KLK-(CO(CH$_2$)$_6$CH$_3$ |
| oo. | (KL)$_8$-(K-KL)$_4$-(K-KL)$_2$-K-KLK-(CO(CH$_2$)$_8$CH$_3$ |
| pp. | (KL)$_8$-(K-KL)$_4$-(K-KL)$_2$-K-KLK-(CO(CH$_2$)$_{10}$CH$_3$ |
| qq. | (KL)$_8$-(K-KL)$_4$-(K-KL)$_2$-K-KLK-(CO(CH$_2$)$_{14}$CH$_3$ |
| rr. | (KL)$_8$-(K-KL)$_4$-(K-KL)$_2$-K-KLK-(CO(CH$_2$)$_{16}$CH$_3$ |
| ss. | (KL)$_8$-(K-KL)$_4$-(K-KL)$_2$-K-KLK-(CO(CH$_2$)$_{22}$CH$_3$ |
| tt. | (KL)$_4$-(K-KL)$_2$-K-KLK-(CO(CH$_2$)$_{16}$CH$_3$ |
| uu. | (CH$_3$(CH$_2$)$_4$CO-KL)$_8$-(K-KL)$_4$-(K-KL)$_2$-K-KL |
| vv. | (CH$_3$(CH$_2$)$_4$CO-KL)$_4$-(K-KL)$_2$-K-KL |
| ww. | (KK)$_8$-(K-KK)$_4$-(K-LL)$_2$-K-LL |
| xx. | (KK)$_8$-(K-LL)$_4$-(K-KK)$_2$-K-LL |
| yy. | (KL)$_4$-(K-KL)$_2$-K-KLK-(CO(CH$_2$)$_{14}$CH$_3$ |
| zz. | (KL)$_4$-(K-KL)$_2$-K-KLK-(CO(CH$_2$)$_{22}$CH$_3$ |

In some embodiments the peptide dendrimer is characterized by the formula

| | |
|---|---|
| a. | (KL)$_4$-(K-KL)$_2$-K-KL |
| b. | (KL)$_4$-(B-KL)$_2$-B-KL |
| c. | (RL)$_4$-(B-RL)$_2$-B-RL |
| d. | (KKL)$_4$-(K-KL)$_2$K-KL |
| e. | (DabW)$_4$-(K-DabW)$_2$-K-DabW |
| f. | (DabL)$_4$-(K-DabL)$_2$-K-DabL |
| g. | (LK)$_8$-(K-LK)$_4$-(K-LK)$_2$-K-LK |
| h. | (KY)$_8$-(K-KL)$_4$-(K-KL)$_2$-K-KL |
| i. | (LA)$_8$-(K-LK)$_4$-(K-LA)$_2$-K-KL |
| j. | (KW)$_8$-(K-KW)$_4$-(K-KW)$_2$-K-KW |
| k. | (KF)$_8$-(K-KF)$_4$-(K-KF)$_2$-K-KF |
| l. | (KL)$_8$-(B-KL)$_4$-(B-KL)$_2$-B-KL |
| m. | (RL)$_8$-(B-RL)$_4$-(B-RL)$_2$-B-RL |
| n. | (LL)$_8$-(K-KK)$_4$-(K-LL)$_2$-K-KK |
| o. | (DabL)$_8$-(K-DabL)$_4$-(K-DabL)$_2$-K-DabL |
| p. | (DabL)$_8$-(K-DabL)$_4$-(K-DabL)$_2$-K-DabW |
| q. | (DabL)$_8$-(K-DabL)$_4$-(K-DabW)$_2$-K-DabW |
| r. | (DabL)$_8$-(K-DabW)$_4$-(K-DabW)$_2$-K-DabL |
| s. | (DabL)$_8$-(K-DabW)$_4$-(K-DabW)$_2$-K-DabA |
| t. | (DabL)$_8$-(K-DabW)$_4$-(K-DabA)$_2$-K-DabW |
| u. | (DabL)$_8$-(K-DabA)$_4$-(K-DabW)$_2$-K-DabW |
| v. | (KL)$_8$-(K-KLCKL)$_4$-(K-KL)$_2$-K-KL |
| w. | (KL)$_{16}$-(K-KL)$_8$-(K-KLCKL)$_4$-(K-KL)$_2$-K-KL |
| x. | (KL)$_{16}$-(K-KLCKL)$_8$-(K-KL)$_4$-(K-KL)$_2$-K-KL |
| y. | (RL)$_8$-(K-RLCRL)$_4$-(K-RL)$_2$-K-RL |
| z. | (KKL)$_4$-(K-KKL)$_2$-K-KKL |
| aa. | (KLL)$_4$-(K-KLL)$_2$-K-KLL |
| bb. | (LKL)$_4$-(K-LKL)$_2$-K-LKL |
| cc. | (KLL)$_8$-(K-KLL)$_4$-(K-KLL)$_2$-K-KLL |
| dd. | (LKL)$_8$-(K-LKL)$_4$-(K-LKL)$_2$-K-LKL |
| ee. | (KL)$_8$-(K-KL)$_4$-(K-LKL)$_2$-K-KKL |
| ff. | (KL)$_8$-(K-KL)$_4$-(K-LKL)$_2$-K-KLL |
| gg. | (KL)$_8$-(K-KL)$_4$-(K-LKL)$_2$-K-KLK |
| hh. | (KL)$_8$-(K-KL)$_4$-(K-LKL)$_2$-K-LKL |
| ii. | (KL)$_4$-(K-KL)$_2$-K-KLK-(CO(CH$_2$)$_4$CH$_3$ |
| jj. | (KL)$_4$-(K-KL)$_2$-K-KLK-(CO(CH$_2$)$_6$CH$_3$ |
| kk. | (KL)$_4$-(K-KL)$_2$-K-KLK-(CO(CH$_2$)$_8$CH$_3$ |
| ll. | (KL)$_4$-(K-KL)$_2$-K-KLK-(CO(CH$_2$)$_{10}$CH$_3$ |
| mm. | (KL)$_8$-(K-KL)$_4$-(K-KL)$_2$-K-KLK-(CO(CH$_2$)$_4$CH$_3$ |
| nn. | (KL)$_8$-(K-KL)$_4$-(K-KL)$_2$-K-KLK-(CO(CH$_2$)$_6$CH$_3$ |
| oo. | (KL)$_8$-(K-KL)$_4$-(K-KL)$_2$-K-KLK-(CO(CH$_2$)$_8$CH$_3$ |
| pp. | (KL)$_8$-(K-KL)$_4$-(K-KL)$_2$-K-KLK-(CO(CH$_2$)$_{10}$CH$_3$ |
| qq. | (KL)$_8$-(K-KL)$_4$-(K-KL)$_2$-K-KLK-(CO(CH$_2$)$_{14}$CH$_3$ |
| rr. | (KL)$_8$-(K-KL)$_4$-(K-KL)$_2$-K-KLK-(CO(CH$_2$)$_{16}$CH$_3$ |
| ss. | (KL)$_8$-(K-KL)$_4$-(K-KL)$_2$-K-KLK-(CO(CH$_2$)$_{22}$CH$_3$ |
| tt. | (KL)$_4$-(K-KL)$_2$-K-KLK-(CO(CH$_2$)$_{16}$CH$_3$ |
| uu. | (CH$_3$(CH$_2$)$_4$CO-KL)$_8$-(K-KL)$_4$-(K-KL)$_2$-K-KL |
| vv. | (CH$_3$(CH$_2$)$_4$CO-KL)$_4$-(K-KL)$_2$-K-KL |
| ww. | (KK)$_8$-(K-KK)$_4$-(K-LL)$_2$-K-LL |
| xx. | (KK)$_8$-(K-LL)$_4$-(K-KK)$_2$-K-LL |
| yy. | (KL)$_4$-(K-KL)$_2$-K-KLK-(CO(CH$_2$)$_{14}$CH$_3$ |
| zz. | (KL)$_4$-(K-KL)$_2$-K-KLK-(CO(CH$_2$)$_{22}$CH$_3$ |
| aaa. | (OrnL)$_4$-(K-DabF)$_2$-K-KL |
| bbb. | (OrnF)$_4$-(K-DabL)$_2$-K-KL |
| ccc. | (RF)$_4$-(K-DabL)$_2$-K-KL |
| ddd. | (OrnF)$_4$-(K-DabL)$_2$-K-KLK-(CO(CH$_2$)$_8$CH$_3$ |
| eee. | (OrnL)$_4$-(K-DabF)$_2$-K-KLK-(CO(CH$_2$)$_8$CH$_3$ |
| fff. | (RF)$_4$-(K-DabL)$_2$-K-KLK-(CO(CH$_2$)$_8$CH$_3$ |

The invention is further illustrated by the following examples and figures, from which further embodiments and advantages can be drawn. These examples are meant to illustrate the invention but not to limit its scope.

SHORT DESCRIPTION OF THE FIGURES

Figure 2:
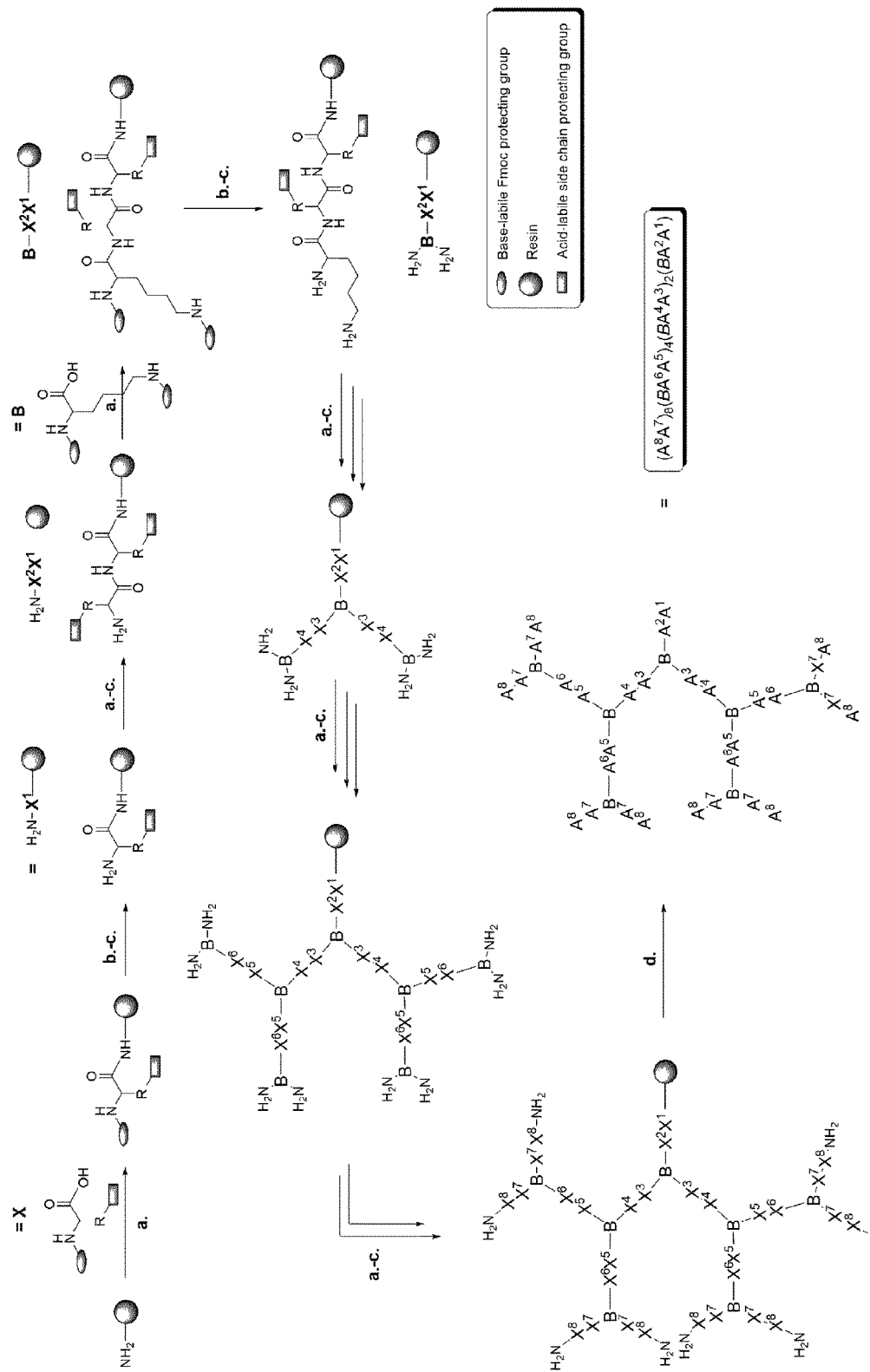

FIG. 1 Topology of $3^{rd}$ generation (G3) peptide dendrimer with 2 AA in between the branching points FIG. 2 Solid-phase peptide synthesis (SPPS) of dendritic peptides. a. Coupling: 3 eq/G Fmoc-amino acid, 3 eq/G PyBOP or HOBt, and 5 eq/G DIPEA or DIC in NMP or DMF. b. Acetylation: Ac$_2$O/DCM (1:1, v/v), 1×15 min. c. Fmoc-Deprotection: piperidine/DMF (1:4, v/v), 20 min. d. Cleavage: TFA (94%), TIS (5%), H$_2$O (1%) (Cys and Met free peptide) or TFA (94%), TIS (1%), H$_2$O (2.5%), EDT (2.5%) (Cys and/or Met containing peptides).

Figure 3:
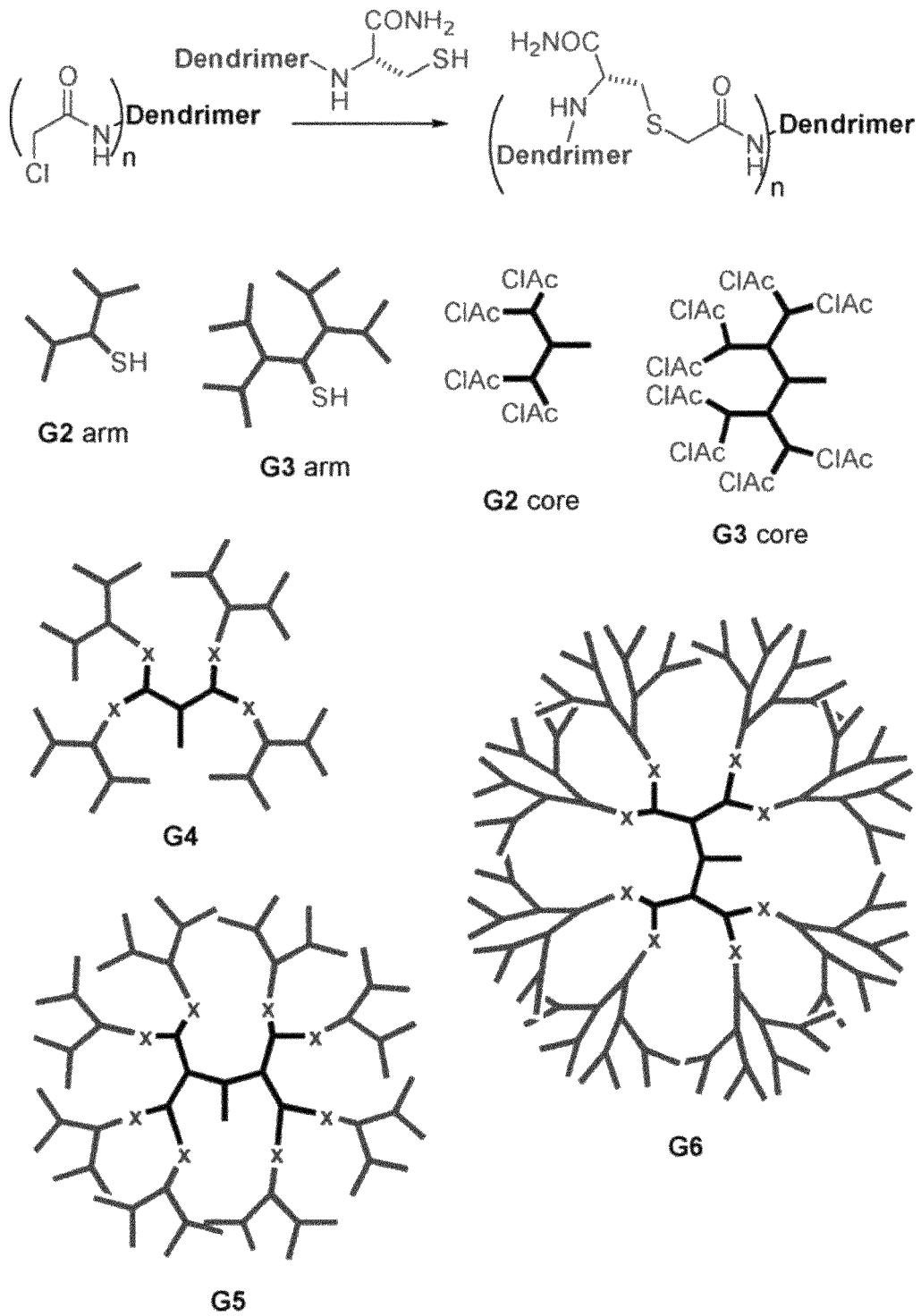
Figure 4:
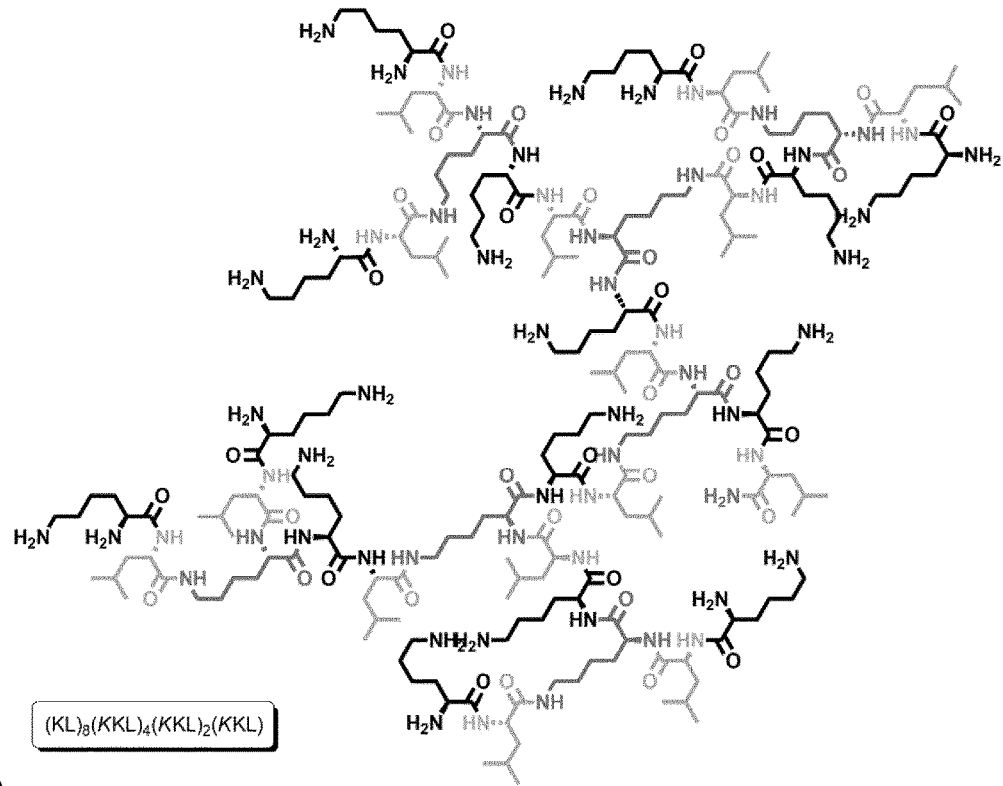
Figure 4:
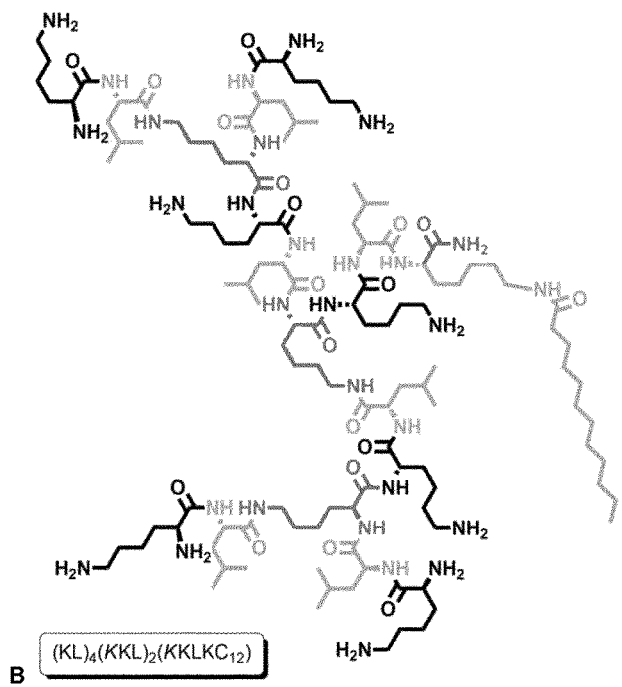

FIG. 3 Assembly of peptide dendrimers by thioligation reaction of lower generation peptide dendrimers FIG. 4 A $3^{rd}$ generation AMPD MSt-112 and B $2^{nd}$ generation AMPD MSt 263 with C$_{12}$ hydrophobic tail attached to core Lys. Charged AAs are in black, hydrophobic AAs in light grey and branching points in dark grey.

Figure 5:
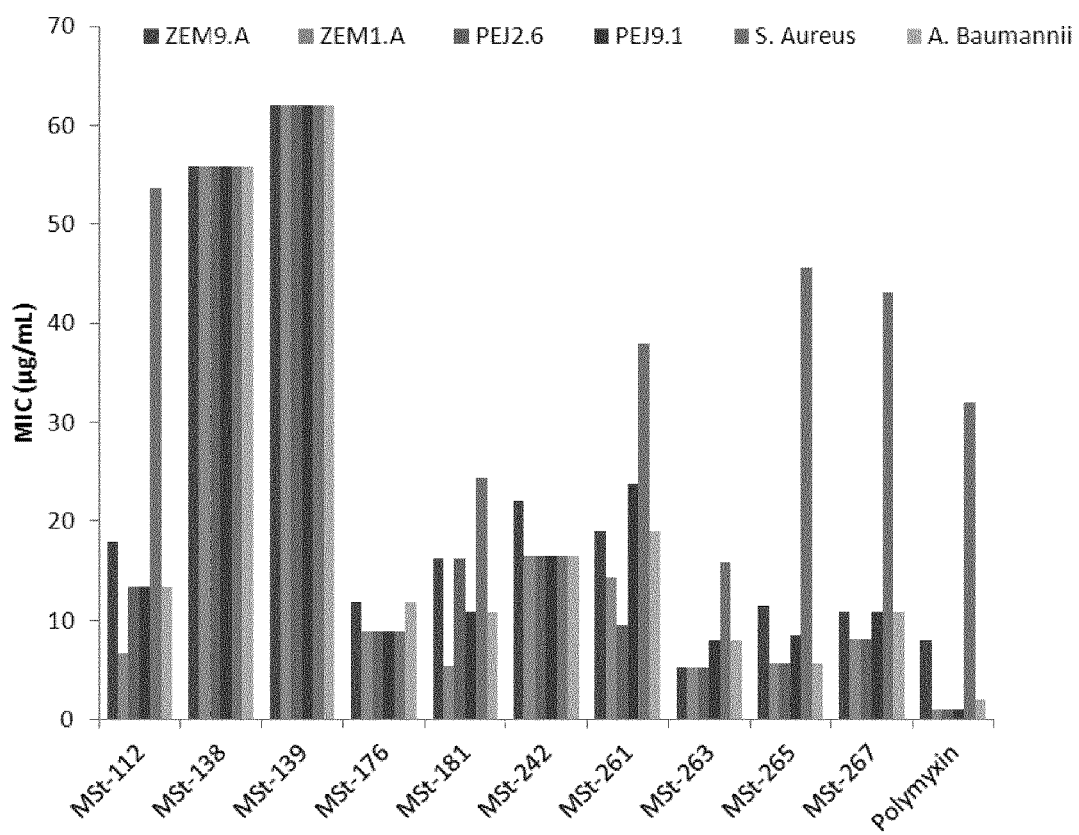

FIG. 5 MIC values in µg/mL of AMPDs against clinical isolates of *P. aeruginosa*, *A. baumannii* and *S. aureus* (measured in 2 independent duplicates, MSt-261 and MSt-265 were only tested once). Maximal measured concentration is 64 µg/mL.

Figure 6:
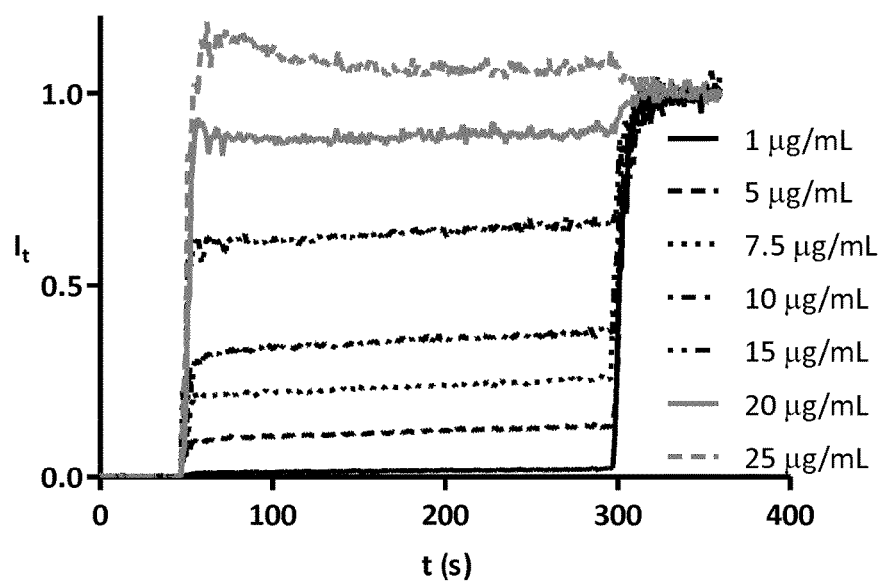
Figure 6:
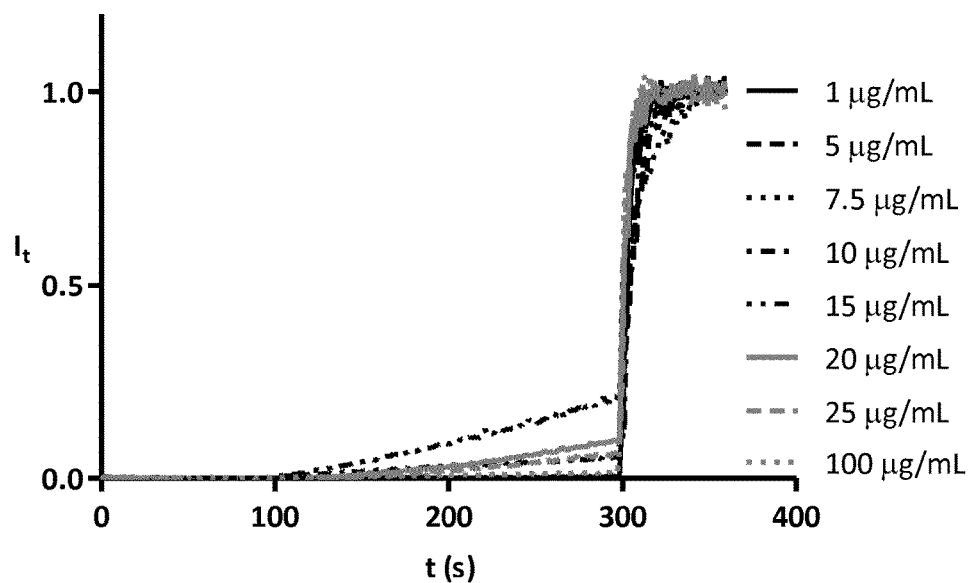

FIG. 6 5(6)-Carboxyfluorescein leakage from phosphatidyiglycerol lipid vesicles. Addition of peptide dendrimers to lipid vesicle solution in buffer (10 mM TRIS, 107 mM NaCl, pH 7.4) at 50 s and addition of 1.2% Triton X 100 at 300 s. Fluorescence intensities were normalized to fractional emission intensity I(t) using $I(t)=(I_t-I_0)/(I_\infty-I_0)$ where $I_0=I_t$ at peptide dendrimer addition, $I_\infty=I_t$ at saturation of lysis. A active AMPD MSt-112 B inactive peptide dendrimer MSt-113 at different peptide concentrations.

Figure 7:
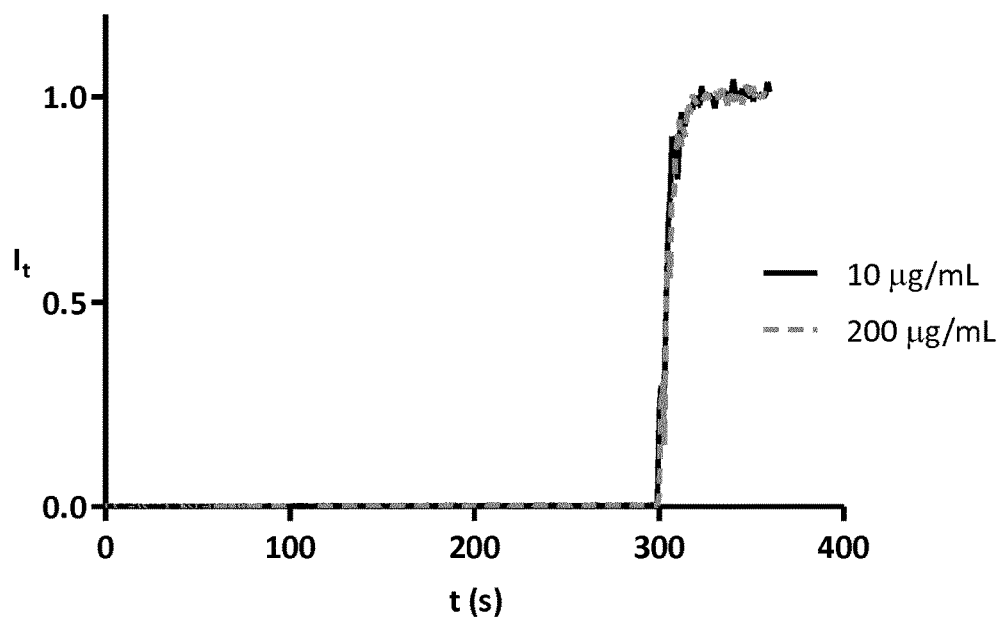
Figure 7:
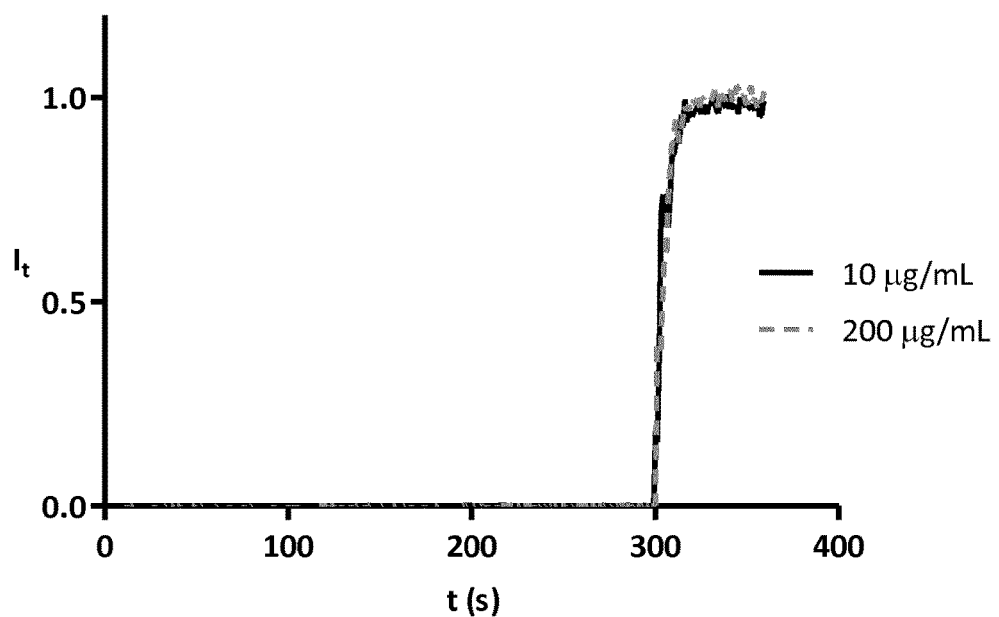

FIG. 7 5(6)-Carboxyfluorescein leakage from phosphatidylcholine lipid vesicles. Addition of peptide dendrimers to lipid vesicle solution in buffer (10 mM TRIS, 107 mM NaCl, pH 7.4) at 50 s and addition of 1.2% Triton X 100 at 300 s. Fluorescence intensities were normalized to fractional emission intensity I(t) using $I(t)=(I_t-I_0)/(I_\infty-I_0)$ where $I_0=I_t$ at peptide dendrimer addition, $I_\infty=I_t$ at saturation of lysis. A active AMPD MSt-112 B inactive peptide dendrimer MSt-113 at different peptide concentrations.

Figure 8:
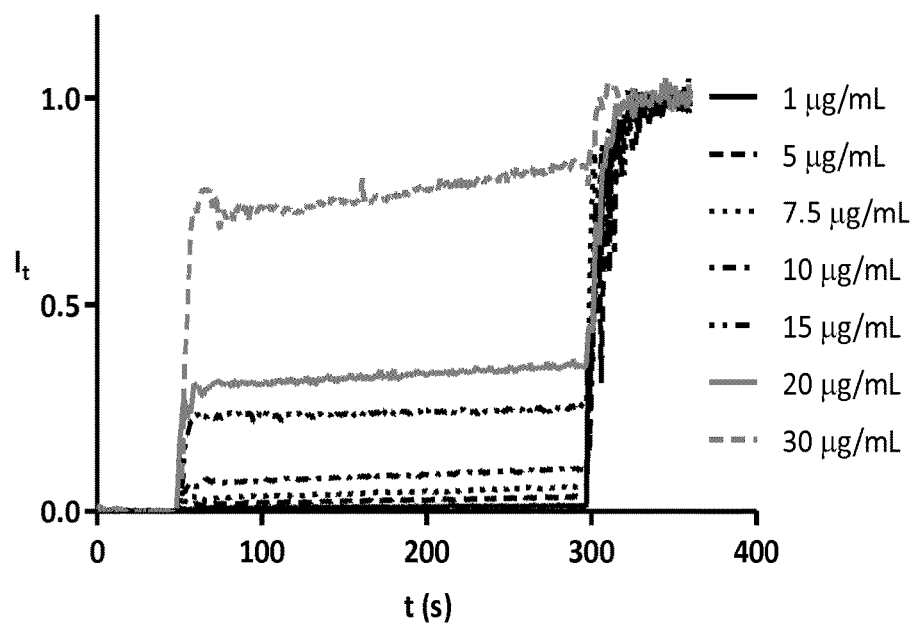
Figure 8:
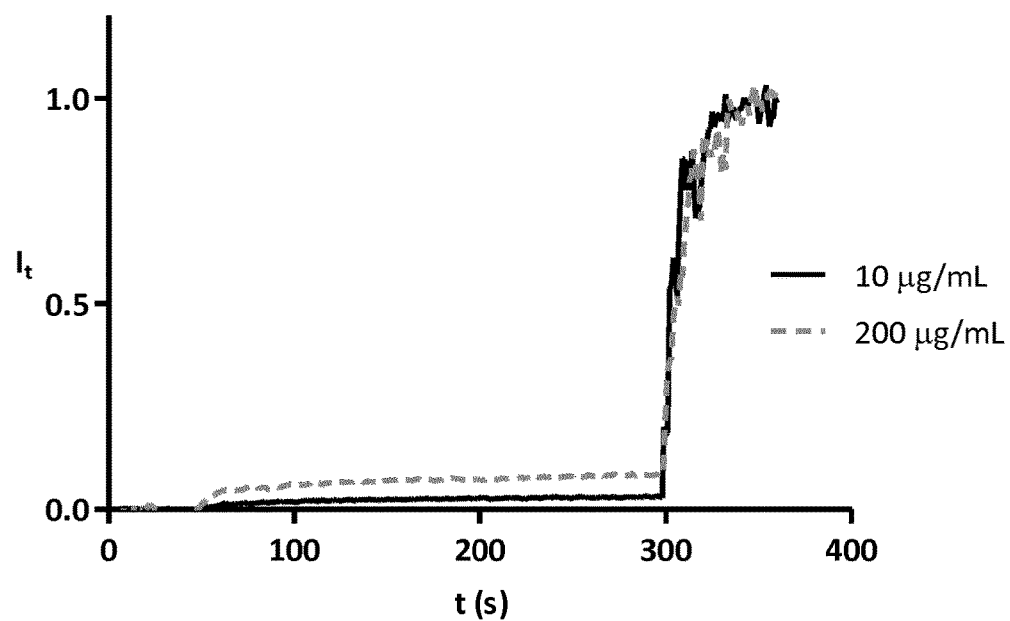

FIG. 8 5(6)-Carboxyfluorescein leakage induced by MSt-260 at different concentrations. Addition of peptide dendrimer to lipid vesicle solution in buffer (10 mM TRIS, 107 mM NaCl, pH 7.4) at 50 s and addition of 1.2% Triton X 100 at 300 s. Fluorescence intensities were normalized to fractional emission intensity I(t) using $I(t)=(I_t-I_0)/(I_\infty-I_0)$ where $I_0=I_t$ at peptide dendrimer addition, $I_\infty=I_t$ at saturation of lysis. A phosphatidylglycerol LUVs B phosphatidylcholine LUVs.

Figure 9:
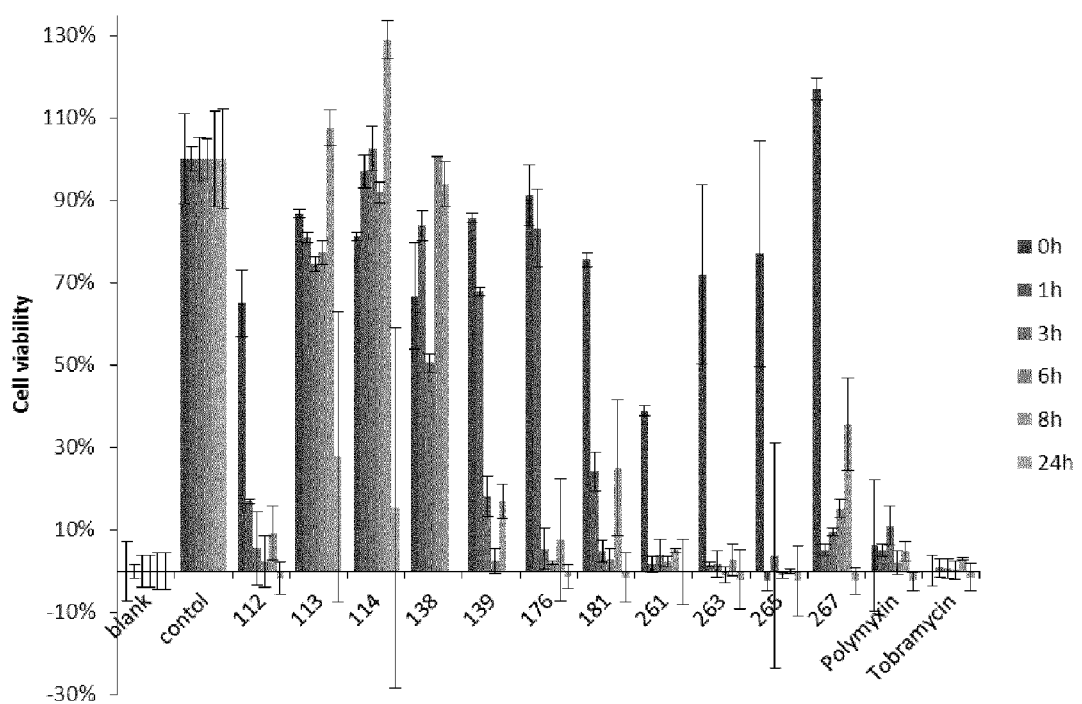

FIG. 9 Cell viability of active and inactive peptide dendrimers measured in two independent duplicates. *P. aeruginosa* were incubated with peptide dendrimers (25 µg/mL) and incubated at 37° C. for 0, 1, 3, 6, 8, 24 hours. After addition of WST-8 and incubation the absorbance was measured at 450 nm.

Figure 10:
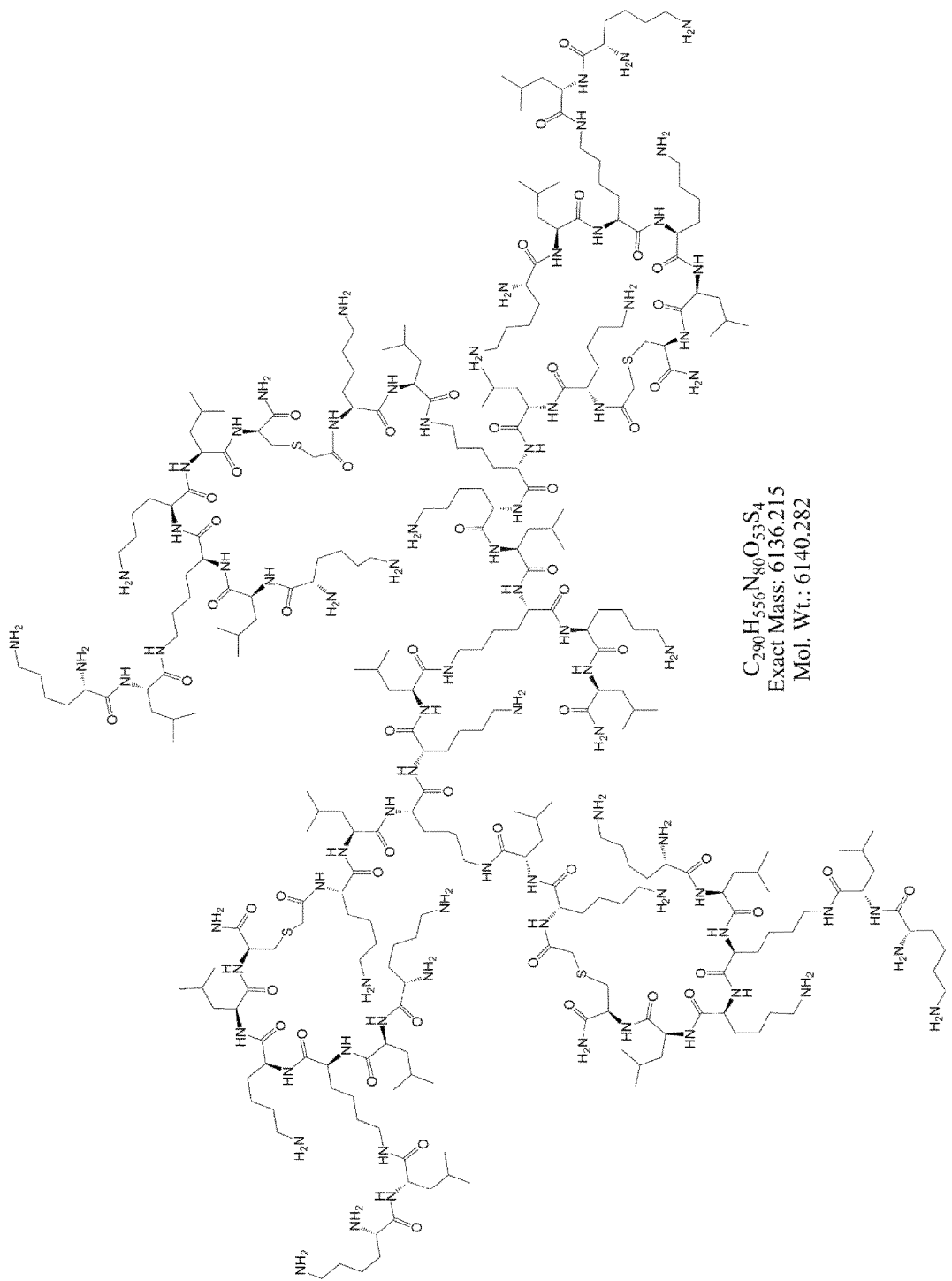

FIG. 10 shows the structure of a thioether-linked exemplary dendrimer.

EXAMPLES

First a library of various compounds with different generations, branching units and charge to hydrophobic ratio was synthesized to get an insight into structure activity relationship (SAR). It was found that for high activity it is beneficial to have a charged and a hydrophobic amino acid in each generation with a charged amino acid in the second position from the C-terminus of the peptide.

A library of AMPDs with hydrophobic chains was synthesized and tested. Carboxylic acids with a chain length of $C_6$ to $C_{24}$ were attached to an additional Lys introduced in the core of $2^{nd}$ and $3^{rd}$ generation AMPDs with KL motive between the branching unit (FIG. 4). The $2^{nd}$ and $3^{rd}$ generation AMPDs with hydrophobic side chains (MSt-260-MSt-267) appeared to be the most potent structures tested against *P. aeruginosa*, including clinical isolates with resistance against common antibiotics. Although addition of hydrophobic side chains to $3^{rd}$ generation AMPDs results in increased haemolytic activity they are much more active in low concentrations before haemolysis occurs.

Experiments to relate the activity of the peptide dendrimers with the primary or secondary structures showed that secondary structures of active and inactive compounds are similar and rather random coil. Active compounds however tend to open up when in contact with a hydrophobic environment. Leakage of 5(6)-Carboxyfluorescein (CF) from negatively charged lipid vesicles but not of neutral lipid vesicles indicate the role of charges in activity. Kinetics with AMPDs with and without hydrophobic side chain demonstrated a faster killing when a lipid is attached to the peptide dendrimer.

Material and Reagents

All reagents, salts, buffers were either purchased from Aldrich, Fluka, Acros Organics, TCI Europe or Dr. Grogg Chemie AG. PyBOP, amino acids and their derivatives were purchased from Advanced ChemTech (USA), Novabiochem (Switzerland), IRIS Biotech (Germany), PolyPeptide (France), GL BioChem (Shanghai). Amino acids were used as the following derivatives: Fmoc-Ala-OH, Fmoc-ß-Ala-OH, Fmoc-Arg(Pbf)-OH, Fmoc-D-Arg(Pbf)-OH, Fmoc-Asp(OtBu)-OH, Fmoc-Gln(Trt)-OH, Fmoc-Gly-OH, Fmoc-His(Boc)-OH, Fmoc-Ile-OH, Fmoc-Leu-OH, Fmoc-D-Leu-OH, Fmoc-Lys(Boc)-OH, Fmoc-D-Lys(Boc)-OH, Fmoc-Lys(Fmoc)-OH, Fmoc-D-Lys(Fmoc)-OH, Fmoc-Lys(Alloc)-OH Fmoc-Phe-OH, Fmoc-Pro-OH, Fmoc-Ser(tBu)-OH, Fmoc-Thr(tBu)-OH, Fmoc-Tyr(tBu)-OH, Fmoc-Val-OH, Fmoc-Dap(Fmoc)-OH, Fmoc-D-Dap(Fmoc)-OH, Fmoc-Dab(Boc)-OH, 4-(Fmoc)-aminomethylbenzoic acid (AMBA), Fmoc-γ-Abu-OH (GABA). Tental Gel S $NH_2$ (loading: 0.32 mmol/g) and Tenta Gel S RAM (loading: 0.22-0.26 mmol·$g^{-1}$) resins were purchased from Rapp Polymere (Germany). 5(6)-carboxyfluorescein (CF) was from Sigma. Egg phosphatidylcholine (EPC), egg phosphatidylglycerol (EPG) and a Mini-Extruder used for vesicle preparation were from Avanti Polar Lipids. Peptide dendrimer syntheses were performed manually in polypropylene syringes fitted with a polyethylene frit, a teflon stopcock and stopper. Analytical RP-UHPLC was performed in Dionex ULTIMATE 3000 Rapid Separation LC System (ULTIMATE-3000RS diode array detector) using a Dionex Acclaim® RSLC 120 C18 column (2.2 µm, 120 Å, 3.0×50 mm, flow 1.2 ml·$min^{-1}$). Compounds were detected by UV absorption at 214 nm. Data recording and processing was done with Dionex Chromeleon Management System Version 6.80 (analytical RP-HPLC). Preparative RP-HPLC was performed with Waters Prep LC2489 chromatography system using a Dr. Maisch Gmbh Reprospher column (C18-DE, 100×30 mm, 5 µm, pore size 100 Å, flow rate 40 mL·$min^{-1}$). Compounds were detected by UV absorption at 214 nm. RP-HPLC was performed using HPLC-grade acetonitrile and mQ-deionized water. The elution solutions were: A $H_2O$ with 0.1% TFA; B $H_2O$/MeCN (50:50); C $H_2O$/MeCN (10:90) with 0.1% TFA; D $H_2O$/MeCN (40:60) with 0.1% TFA. MS spectra, amino acid analyses and DOSY-NMR measurements were provided by Mass Spectrometry, Protein Analysis and NMR services respectively of the Department of Chemistry and Biochemistry at the University of Berne. Yields were determined with quantitative amino acid analysis (AAA) if not noted otherwise. Fluorescence measurements were performed with a Fluorescence spectrophotometer (Cary Eclipse, Varian) equipped with a stirrer and a temperature controller (measurements at 25° C. unless otherwise noted).

Dendrimer Synthesis

Peptide Dendrimers without Modifications

The resin (Tenta Gel S RAM) was swelled in 8 mL $CH_2Cl_2$ and the Fmoc-protecting groups of the resin were removed with a solution of 20% piperidine in DMF (2×10 min.). For further couplings, the resin was acylated with one of the protected amino acids (3 eq/G, G=generation) in the presence of PyBOP (benzotriazol-1-yl-oxytripyrrolidino-phosphonium hexafluorophosphate) (3 eq/G) and DIPEA (N,N-Diisopropylethylamine) (5 eq/G) in about 8 mL NMP. Amino acids, derivatives or diamino acids were coupled for 1 h (G0), 2 h (G1), 3 h (G2), 4 h (G3). The completion of the reaction was checked using 2,4,6-trinitrobenzenesulfonic acid solution (TNBS) or chloranil test (for proline). If the beads were red (brown for proline), there were some free amino groups and the resin test was positive. If they were colorless, there were no more free amino groups and the resin test was negative. The coupling was repeated after a positive test. Capping of unreacted peptide chains was carried out with a solution of acetic anhydride and $CH_2Cl_2$ (1:1 v/v) for 15 min. After each coupling, the resin in each syringe was deprotected (20% piperidine in DMF, 2×10 min) followed by TNBS or chloranil test (test must be positive) and the next protected amino acid was added. At the end of the synthesis, the terminal amino groups were either acetylated with $Ac_2O$/$CH_2Cl_2$ (1:1) for 20 min. or not acetylated. The resin was washed twice with MeOH and dried under vacuum before the cleavage was carried out using TFA/TIS/$H_2O$ (94:5:1 v/v/v) during 4.5 h. For peptides with cysteine or methionine the cleavage conditions are TFA/TIS/$H_2O$/EDT (94/1/2.5/2.5 v/v/v/v). After filtration the peptide was precipitated with 50 mL ice cold tert-butylmethylether (TBME), centrifuged at 4400 rpm for 15 min, and washed twice with TBME. For purification of the crude peptide, it was dissolved in A (100% mQ-$H_2O$, 0.1% TFA), subjected to preparative RP-HPLC and obtained as TFA salt after lyophilisation. Unless not mentioned, gradient used for analytical HPLC is A/D=100/0 to 0/100 in 2.2 min, 1.2 mL·min$^{-1}$.

Peptide Dendrimers with Carboxylic Acid Attached to Lys Side Chain

Synthesis was carried out according to "Peptide Dendrimers without modifications" Fmoc-Lys(Alloc)-OH was attached first to the resin. Before deprotection of the last Fmoc-group the Alloc protecting group was removed under dry conditions with 0.25 eq of Pd(PPh$_3$)$_4$ as catalyst dissolved in 5 mL dry DCM and 25 eq. of PhSiH$_3$. This step was repeated twice with washing of the resin with 2× dry DCM in between. After the second cycle the resin was washed for 1 h with DCM and deprotection was check by testing for free amine groups with TNBS test. If the test was red the carboxylic acid (5 eq.) was first dissolved with HOBt (5 eq.), DIC (5 eq.) and DIPEA (3 eq.) in NMP/DCM (1/1 v/v) added to the resin and stirred for 3-4 hours. After washing with 3×NMP, MeOH, DCM the coupling was repeated with the carboxylic acid (5 eq.) dissolved with HATU (5 eq.) and DIPEA (3 eq.) in DMF/DCM (1/1 v/v) over night. Deprotection of the last Fmoc-group was done after washing 3×NMP, MeOH, DCM and checking for free amine groups with TNBS test (colorless) followed by cleavage and purification as described in "Peptide Dendrimers without modifications".

Peptide Dendrimer Synthesis Using the Thioether Ligation Strategy

Thioether Ligation

Core and arm peptides were synthesized according to the procedure given above. Before cleavage of the core peptides from the solid phase and purification, the N-termini were chloroacetylated with a solution of chloroacetic acid anhydride (10.0 equivalents per free N-terminus) in 5 mL DCM for 2 times 15 min. The resin was washed (3 times each) with NMP, MeOH and DCM.

In a typical experiment a solution of core peptide (sequence containing chloroacetyl groups, 1.0 eq.) and KI (20.0 eq.) in DMF/H$_2$O (1/1, v/v) (300 µL) were prepared in a 5 mL pointed glass flask. The mixture was degassed with argon during 10 min. In a second 5 mL pointed glass flask the arm peptide (Cys containing sequence, 1.5 eq. per chloroacetyl group in core sequence) was prepared (without solvent) and the flask was degassed with argon/vacuum 3 times. The core peptide solution was transferred to the glass flask containing the arm peptide with a gas tight syringe. DIPEA (55.0 eq.) was added and the solution was stirred at room temperature. The reaction was followed by analytical RP-HPLC (1.0 µL reaction mixture taken with a gas tight 10 µL glass syringe+100 µL of solvent A). After completion (usually overnight), the reaction was quenched by adding 5 mL of solvent A, filtered and purified by preparative RP-HPLC. Yields were corrected with amino acid analysis.

CCS-20 (KL)$_8$(KKLCxKL)$_4$(KKL)$_2$KKLNH$_2$ was obtained from starting materials CCS-2 (ClAcKL)$_4$(KKL)$_2$KKLNH$_2$ and CCS-5 (KL)$_2$KKLCNH$_2$ using the general procedure described above as white foamy solid after preparative RP-HPLC purification (11.2 mg, 1.82 µmol, 73%). Anal. RP-HPLC: t$_R$=1.51 min (A/D=100/0 to 0/100 in 2.2 min., λ=214 nm). MS (ESI+): C$_{290}$H$_{556}$N$_{80}$O$_{53}$S$_4$ calc./found. 6140.28/6140.3 [M]$^+$, 6240.46/6239 [M+2K+Na]$^+$. "x" denotes a thioether linkage of the cysteine side chain with an acetic acid moiety bound to the N-terminus of the C-terminally neighboring amino acid via an amide bond.

Amino Acid Analysis

Samples were hydrolyzed with 6 M HCl containing 0.1% phenol (v/v) for 22 h at 115° C. under N$_2$ vacuum (Chang, J.-Y. and Knecht, R., 1992, Anal. Biochem., 197, 52-58). The liberated amino acids were coupled with phenylisothiocyanate (PITC), and the resulting phenylthiocarbamoyl (PTC) amino acids were analyzed by RP-HPLC on a Nova Pack C18 column (4 µm, 3.9 mm×150 mm, Waters) with a Dionex Summit® HPLC system with an automatic injection system (Bidlingmeyer, B. A. et al., 1984, Journal of Chromatography B, 336, 93-104). The corresponding ammonium acetate buffer replaced the 0.14 M sodium acetate buffer, pH 6.3. If Cys was involved in a thioether bridge, then it was detected as carboxymethyl Cys (CMCys). Otherwise Cys was destroyed during the hydrolysis. Due to hydrolyzation Trp can't be detected with this method and Asn/Gln have the same retention time as Asp/Glu respectively. Phe and Dap elute also at the same retention time. In this analysis the amount of serine detected is usually significantly lower than the theoretically expected amount. All yields, MICs (minimal inhibitory concentrations), MBC (Minimal bactericidal concentration) and MHCs (minimal haemolytic concentrations) were corrected according to the content of peptide resulted from this method.

Biological Assays

Broth Microdilution Method for Antimicrobial Peptides I

Antimicrobial activity was assayed against *Bacillus subtilis* (strain BR151), *Escherichia coli* (strain DH5α) and *Pseudomonas aeruginosa* (strain PA01). Microdilution broth method was used to determine the minimal inhibitory concentration (MIC). A colony of bacteria was grown in LB-medium overnight at 37° C. The concentration was quantified by measuring absorbance at 600 nm and diluted to OD$_{600}$=0.1 (1×10$^8$ CFU/mL). The samples were prepared as stock solutions of 1 mg mL$^{-1}$ in H$_2$O and diluted serially by ⅔ in nutrient LB in a 96-well microtiterplate (Cornstar, polypropylene, untreated). The sample solutions (50 µL) were mixed with the diluted bacterial suspension with an OD$_{600\ nm}$ of 0.001 (50 µL). This results in the final desired inoculation of 5×10$^5$ CFU/mL. The plates were incubated at 37° C. until satisfactory growth (18-24 h). For each test, two columns of the plate were kept for sterility control (SC, broth only) and growth control (GC, broth with bacterial inoculums, no antibiotics). 10 µL of a solution of MTT (0.1% in H$_2$O) was added to each well. The minimal inhibitory concentration (MIC) was defined as the lowest concentration of the antimicrobial substance (peptide dendrimer) that inhibited visible growth of the tested bacteria (yellow) with the unaided eye. For microbiological study the linear peptide LysTyrLysLysAlaLeuLysLysLeuAlaLysLeuLeu (SEQ ID No. 1) was used as reference.

Broth Microdilution Method for Antimicrobial Peptides II

Antimicrobial activity was assayed against *P. aeruginosa* PA01 (WT), *P. aeruginosa* PT1482 (A-), PT1485 (A-B-), PT1149 (A-B-C-algC), PT331 (Z61) (LPS mutants), *P. aeruginosa* PEJ2.6, PEJ9.1, ZEM1.A, ZEM9.A (clinical isolates from Université de Genève/Centre Médical Universitaire), *Burkholderia cenocepacia* (*B. ceno*), *Staphylococcus aureus* (*S. aureus*, MRSA strain) and *Acinetobacter baumannii* (*A. baum*) (clinical isolates from Université de Genève/Centre Médical Universitaire). To determine the minimal inhibitory concentration (MIC), microdilution broth method was used. A colony of bacteria was grown in MH-medium overnight at 37° C. The samples were prepared as stock solutions of 8 mg mL$^{-1}$ in H$_2$O, diluted to the beginning concentration of 32, 64, 128 or 256 µg/mL in 300 µL MH-medium, added to the first well of 96-well microtiterplate (TPP, untreated) and diluted serially by ½. The concentration of the bacteria was quantified by measuring absorbance at 600 nm and diluted to OD$_{600}$=0.022 in MH-medium. The sample solutions (150 μL) were mixed with 4 μL diluted bacterial suspension with a final inoculation of about of 5×10⁵ CFU. The plates were incubated at 37° C. until satisfactory growth (~18 h). For each test, two columns of the plate were kept for sterility control (SC, broth only) and growth control (GC, broth with bacterial inoculums, no antibiotics). The minimal inhibitory concentration (MIC) was defined as the lowest concentration of the antimicrobial substance (peptide dendrimer) that inhibited visible growth of the tested bacteria with the unaided eye. For microbiological study Polymyxin was used as references.

Haemolysis Assay

To determine the minimal haemolytic concentration (MHC) stock solutions of 8 mg/mL of the peptide dendrimers in $H_2O$ were prepared and 50 μL were diluted serially by ½ in 50 μL PBS (pH 7.4) in 96-well plate (Cornstar or Nunc, polystyrene, untreated). Human red blood cells (hRBC) were obtained by centrifuging 1.5 mL of whole blood from friendly donors at 3000 rpm for 15 minutes. Plasma was discarded and the pellet was re-suspended in a 15 mL falcon tube up to 5 mL of PBS. The washing was repeated three times and the remaining pellet was re-suspended in 10 mL of PBS at a final hRBC concentration of 5%. The hRBC suspension (50 μL) was added to each well and the plate was incubated at room temperature for 4 hours. Minimal haemolytic concentration (MHC) end points were determined by visual inspection of the wells after the incubation period. Controls on each plate included a blank medium control (50 μl PBS+50 μl of hRBC suspension) and a haemolytic activity control (mQ-deionized water 50 μL+50 μL hRBC suspension).

Preliminary Resistant Development Assay

MICs of compounds for *B. subtilis* BR151 were determined daily for 15 days using cells from the well in which the compound concentration was one-half the MIC value (½ MIC well). For each compound, the bacteria from ½ MIC well from the previous MIC assay plate were re-suspended in LB-Broth, incubated for 2-4 h at 37° C. and the $OD_{600}$ was determined. The re-suspension was then diluted to 5×10⁵ cells/ml in LB Broth ($OD_{600}$=0.1 then diluted 1:100 fold to get $OD_{600}$=0.001) and used to again determine the MIC of the same compound to which those cells had previously been exposed. All MIC determinations were done in duplicate.

In-Vivo Study

Animals:

4-6 weeks old male wistar rats (weight range 200-500 g) were used in toxicity experiments. Rats were obtained from Zentrale Tierställe Bern (Department of Clinical Research from University of Bern) and housed 4 per cage. Each experimental group includes two rats. All procedures, care and handling of the animals were reviewed and approved by the Veterinärdienst of Kanton Bern, Schweiz and execute in collaboration with the group of Prof. Hugues Abriel from Department of Clinical Research from University of Bern.

Treatment:

Rats were anesthetized with 4% isoflurane and 1 L/min oxygen in an induction chamber. When the rats were sleeping they were transferred on a clinical drape and anesthetized with 1-2% isoflurane and 0.8 l/min oxygen via a mask. The tail was warmed up with warm water and disinfected with 70% ethanol. The intravenous (i.v.) injections into the tail vein included a single dose of the AMPD of 2 mg/kg rat in 500 μL PBS. Before injection each rat was weighted individually and the exact dosage was determined. All rats, including control groups with no injection and i.v. injection of 500 μL PBS, were monitored for their survival and behavior for two days.

WST-8 Cell Viability Assay

Cell viability was assayed against *Pseudomonas aeruginosa* (strain PA01). A colony of bacteria was grown in LB-medium overnight at 37° C. The concentration was quantified by measuring absorbance at 600 nm and diluted to $OD_{600}$=0.1 (1×10⁸ CFU/mL). The samples were prepared as stock solutions of 1 mg mL⁻¹ in $H_2O$ and diluted in LB to a concentration of 50 μg/mL in a 96-well microtiterplate (TPP, untreated). The sample solutions (50 μL) were mixed with the diluted bacterial suspension with an $OD_{600\ nm}$ of 0.001 (50 μL). This results in the final desired inoculation of 5×10⁵ CFU/mL. The plates were incubated at 37° C. for 1, 3, 6, 8 and 24 h. Each time point was assayed on a separate plate. For each test, two columns of the plate were kept for sterility control (SC, broth only) and growth control (GC, broth with bacterial inoculums, no antibiotics). After incubation 15 μL of WST-8 working solution (3.31 mg/mL WST-8 (Ochem Incorporation), 0.074 mg/mL PES (phenazine ethosulfate)) was added to each well and cells were incubated at 37° C. until GC had desired value. After the reaction took place, the final absorbance was read at 450 nm. For calculations, the value of the GC was set to 100% cell viability and the value of the negative control (no bacteria, SC) was set to 0% cell viability. With these two values a calibration curve was produced.

Proteolytic Stability of Peptides and Peptide Dendrimers with Human Serum

Peptides and peptide dendrimers were prepared as 200 μM stock solution in PBS. 25% Human Serum (diluted with DMEM) was centrifuged at for 15 min at 14000 rpm to remove the lipids and supernatant was collected and incubated for 15 min at 37° C. Proteolysis was initiated upon addition of 50 μL of the test peptide or peptide dendrimer to 50 μL of serum and shaking at 37° C. Final peptide concentration is 100 μM. Reaction mixtures were analyzed after 0, 1, 6, 24 h by addition of ice-cold 10% Trichloroacetic acid (TCA) to precipitate serum proteins. The supernatant was collected for each sample after centrifugation at 14000 rpm for 15 min. and evaporated with a speedvac. After dissolving the solid in 100 μL mQ-$H_2O$ they were analyzed by RP-UPLC (flow rate: 1.2 mL/min. gradient: A/D=100/0 to 0/100 in 7.5 min). Conversions of the remaining peptide and peptide dendrimers were calculated by integration of the absorbance at 214 nm by using Chromeleon software.

Detection of Peptide in the Presence of Bacteria

Peptides and peptide dendrimers were prepared as 200 μM stock solution in $H_2O$. A colony of bacteria was grown in LB-medium overnight at 37° C. The concentration was quantified by measuring absorbance at 600 nm and diluted to $OD_{600}$=0.2. Degradation was initiated upon addition of 50 μL of the test peptide or peptide dendrimer to 50 μL of the bacterial suspension and shaking at 37° C. Final peptide concentration is 100 μM and final concentration of bacteria is $OD_{600}$=0.1 (1×10⁸ CFU/mL). Reaction mixtures were analyzed after 0, 1, 6, 9, 24 h by heating up to 95° C. for 5 min. followed by centrifugation for 15 min. at 14000 rpm. 50 μL of the supernatant were collected for each sample and 50 μL A were added giving a concentration of 50 μM. 5 μL of 4-Hydroxybenzoic acid (standard) were added before samples were analyzed by RP-UPLC (flow rate: 1.2 mL/min. gradient: A/D=100/0 to 0/100 in 7.5 min). Conversions of the remaining peptide and peptide dendrimers were calculated by integration of the absorbance at 214 nm by using Chromeleon software.

Lipid Vesicles Experiments

Preparation A thin lipid film was prepared by evaporating a solution of 25 mg Egg PC or Egg PG in 1 mL MeOH/CHCl$_3$ 1/1 on a rotary evaporator (rt) and then in vacuo overnight. The resulting film was hydrated with 1 mL buffer (50 mM CF, 10 mM TIRS, 10 mM NaCl, pH 7.4) for 30 min, subjected to freeze-thaw cycles (7×) and extrusion (15×) through a polycarbonate membrane (pore size 100 nm). Extravesicular components were removed by gel filtration (Sephadex G-50) with 10 mM TRIS, 107 mM NaCl, pH 7.4. Final conditions: ~2.5 mM Egg PC or Egg PG; inside: 50 mM CF, 10 mM TIRS, 10 mM NaCl, pH 7.4; outside: 10 mM TRIS, 107 mM NaCl, pH 7.4.

Experiment Egg PC or Egg PG stock solutions (37.5 µL) were diluted with a buffer (10 mM TRIS, 107 mM NaCl, pH 7.4) and placed in a thermostated fluorescence cuvette (25° C.) and gently stirred (total volume in the cuvette ~3000 µL; final lipid concentration ~31.25 µM). CF efflux was monitored at $\lambda_{em}$ 517 nm ($\lambda_{ex}$ 492 nm) as a function of time after addition of 20 µL of peptide dendrimer in buffer (10 mM TRIS, 107 mM NaCl, pH 7.4) with final concentrations of 1, 5, 7.5, 10, 15, 20, 25, 30 µg/mL at t=50 s and 1.2% trition X-100 (30 µL, 0.012% final concentration) at t=300 s. Fluorescence intensities were normalized to fractional emission intensity I(t) using $I(t)=(I_t-I_0)/(I_\infty-I_0)$ where $I_0$ $I_t$ at peptide dendrimer addition, $I_\infty=I_t$ at saturation of lysis.

Results and Discussion

Design and Synthesis of Antimicrobial Peptide Dendrimers (AMPD) with One, Two or Three Amino Acids Between Branching Units To identify dendrimers with antimicrobial effects, common characteristics of linear antimicrobial peptides were incorporated into the dendritic scaffold (FIG. 1). Cationic amino acids like Lys and Arg were chosen for creating charges on the peptide dendrimer and Leu, Ile, Tyr, Phe, Trp and Ala were picked as hydrophobic counterparts to establish amphiphilicity.

A library of 78 peptide dendrimers (53 normal, 18 with alky chain, 7 G4 and G5, additionally 2 linear peptides, 6 dimers) was synthesized using standard Fmoc-SPPS (Merrifield, R. et al., 1963, Am. Chem. Soc., 85, 2149-2154; Kent, S. B. et al., 2009, Chem. Soc. Rev., 38, 338-51) on Rink-amide resin (FIG. 2). For AMPDs with a hydrophobic tail in the core an additional Lys with Alloc as orthogonal protecting group in the side chain was placed as first amino acid in the synthesis. After Alloc-deprotection (Grieco, P. et al., 2001, J. Peptide Res., 57, 250-256) with 0.25 eq. of Pd(PPh$_3$)$_4$ and 25 eq. PhSiH$_3$ the different carbon side chains, ranging from 6 to 24 carbon atoms, were attached as carboxylic acid under classic coupling conditions with HATU/DIPEA in DMF or HOBt/DIC/DIPEA in NMP. Concomitant acidic cleavage and side chain deprotection of the peptide dendrimers was carried out after the last Fmoc-deprotection followed by RP-HPLC purification. Table 2 to Table 7 show all synthesized AMPDs with very good (44-10%) to good (10-1%) yields for all different generations and numbers of amino acids between the branching units. The yields correspond to pure fractions from the HPLC and synthesis and purification was not optimized. The structure formula of a third generation peptide dendrimer and a second generation with attached alkyl chain are shown in FIG. 4.

For all tables given in the following, peptide dendrimers sequences are given from N-termini to C terminus. One letter code is used for amino acids, with upper case signifying L- and lower case D-enantiomers. Dab is L-2,3-diaminobutyric acid and B is L-2,3-diaminopropionic acid. Branching diamino acids are given in italics. Where not stated otherwise, all peptides are carboxamides (CONH$_2$) at the C-terminus. Where yields are given, these relate to RP-HPLC purified products as TFA salts.

MIC (minimal inhibitory concentration) and MHC (minimal haemolytic concentration, determined on human red blood cells (hRBC)) values are given in µg/mL. When no detectable haemolytic activity was observed, the last measured concentration was used for calculation of the therapeutic index. TI (therapeutic index)=MHC (µg/ml)/geometric mean of MIC (µg/ml). Larger values indicate greater antimicrobial specificity.

TABLE 2

Amino acid sequences, yields and MS analysis of 3$^{rd}$ generation AMPDs.

| Compound | Sequence | Yield/mg (%) | MS calc./obsd. |
|---|---|---|---|
| MSt-112 | (KL)$_8$(KKL)$_4$(KKL)$_2$(KKL) | 52.2 (8) | 4534.19/4535.10 |
| MSt-242 | (RL)$_8$(KRL)$_4$(KRL)$_2$(KRL) | 12.6 (2) | 4954.39/4653.49 |
| MSt-199 | (LK)$_8$(KLK)$_4$(KLK)$_2$(KLK) | 7.8 (1) | 4534.19/4534.84 |
| MSt-114 | (KY)$_8$(KKL)$_4$(KKL)$_2$(KKL) | 53.0 (6) | 4934.31/4935.24 |
| MSt-120 | (LA)$_8$(KLK)$_4$(KLA)$_2$(KKL) | 27.6 (4) | 4083.36/4084.02 |
| MSt-172 | (KW)$_8$(KKW)$_4$(KKW)$_2$(KKW) | 3.29 (<1) | 5629.97/5651.89 |
| MSt-174 | (KF)$_8$(KKF)$_4$(KKF)$_2$(KKF) | 17.4 (2) | 5044.43/5048.77 |
| MSt-136 | (KL)$_8$(BKL)$_4$(BKL)$_2$(BKL) | 68.0 (3) | 4239.63/4239.85 |

TABLE 2-continued

Amino acid sequences, yields and MS analysis of 3$^{rd}$ generation AMPDs.

| Compound | Sequence | Yield/mg (%) | MS calc./obsd. |
|---|---|---|---|
| MSt-137 | (RL)$_8$(BRL)$_4$(BRL)$_2$(BRL) | 6.6 (<1) | 4659.83/4660.12 |
| MSt-140 | (KK)$_8$(KKK)$_4$(KLL)$_2$(KLL) | 15.2 (2) | 4669.32/4669.73 |
| MSt-179 | (KK)$_8$(KLL)$_4$(KKK)$_2$(KLL) | 5.1 (1) | 4609.00/4612.00 |
| MSt-180 | (LL)$_8$(KKK)$_4$(KLL)$_2$(KKK) | 6.9 (1) | 4456.32/4460.74 |
| MSt-181 | (kl)$_8$(kkl)$_4$(kkl)$_2$(kkl) | 16.9 (2) | 4534.19/4536.20 |
| MSt-154 | (kl)$_8$(bkl)$_4$(bkl)$_2$(bkl) | 60.7 (9) | 4239.63/4239.69 |
| MSt-155 | (rl)$_8$(krl)$_4$(krl)$_2$(krl) | 10.6 (2) | 4954.39/4954.75 |
| MSt-156 | (rl)$_8$(brl)$_4$(brl)$_2$(brl) | 13.5 (2) | 4659.83/4660.52 |
| MSt-200 | (DabL)$_8$(KDabL)$_4$(KDabL)$_2$(KDabL) | 10.9 (1) | 4113.39/4114.02 |
| MSt-202 | (DabL)$_8$(KDabW)$_4$(KDabL)$_2$(KDabW) | 6.7 (5) | 4478.65/4479.02 |
| MSt-203 | (DabL)$_8$(KDabL)$_4$(KDabW)$_2$(KDabW) | 6.0 (1) | 4332.54/4333.09 |
| MSt-204 | (DabL)$_8$(KDabW)$_4$(KDabW)$_2$(KDabL) | 7.2 (1) | 4624.75/4625.40 |
| MSt-205 | (DabL)$_8$(KDabW)$_4$(KDabW)$_2$(KDabA) | 12.7 (1) | 4509.62/4510.13 |
| MSt-206 | (DabL)$_8$(KDabW)$_4$(KDabA)$_2$(KDabW) | 9.1 (1) | 4394.49/4395.22 |
| MSt-207 | (DabL)$_8$(KDabA)$_4$(KDabW)$_2$(KDabW) | 6.0 (1) | 4164.23/4164.65 |

First series of AMPDs consisted of 3$^{rd}$ generation peptide dendrimers. Initially amino acids commonly present in natural antimicrobial peptides were incorporated in the dendritic structure. In a first round Lys or Arg were alternated with the hydrophobic amino acids Leu, Ala, Trp, Phe, Tyr between a Lys-branching. To create more rigidity a smaller branching unit B (L-2,3-diaminopropionic acid) unit was used. In a second design charge and hydrophobicity were concentrated either in the core or at the outer sphere. Peptide dendrimers are very flexible molecules without well-defined secondary structures. For mechanistic investigation and more stability concerning physiological conditions, four promising sequences were synthesized as all D-enantiomers. To vary not only the positive charge by a different amino acid but also to see if the length of the side chain is influencing the activity Lys with four methylene groups in the side chain was substituted by Dab (L-2,3-diaminobutyric acid) with only two methylenes.

To cover a wider scope of structures, 2$^{nd}$ generation peptide dendrimers were prepared. Their synthesis is easier and faster, and this leads to higher yields. 2$^{nd}$ generation AMPDs MSt-146, MSt-138, MSt-139, MSt-119, MSt-176 and MSt-201 hold the same features as their 3$^{rd}$ generation analogues but have only half the molecular weight. 4$^{th}$ and 5$^{th}$ generation peptide dendrimers and second generation peptide dimers were produced as well to explore other structural possibilities (Tables 4 and 5).

Since the SPPS of peptide dendrimers is limited on bead up to the 3$^{rd}$ generation, 4$^{th}$ and 5$^{th}$ generation AMPDs were synthesized via a convergent approach using a published procedure (Uhlich, N. A. et al. *Org. Biomol. Chem.* 2011, 9, 7084). Thus 2$^{nd}$ and 3$^{rd}$ generation peptide dendrimers were prepared with chloroacetyl-groups at the N-termini. In a thioether ligation those peptide dendrimers and 1$^{st}$ or 2$^{nd}$ generation peptide dendrimers with an additional cysteine at the C-terminus were coupled to form 4$^{th}$ and 5$^{th}$ generation AMPDs in good yields (Table 4).

TABLE 3 shows amino acid sequences, yields and MS analyses of 2$^{nd}$ generation AMPDs.

| Compound | Sequence | Yield/mg (%) | MS calc./obsd. |
|---|---|---|---|
| MSt-146 | (KL)$_4$(KKL)$_2$(KKL) | 44.9 (15) | 2090.86/2091.29 |
| MSt-138 | (KL)$_4$(BKL)$_2$(BKL) | 140.0 (13) | 1964.62/1964.76 |
| MSt-139 | (RL)$_4$(BRL)$_2$(BRL) | 70.0 (13) | 2160.71/2160.95 |
| MSt-119 | (KKL)$_4$(KKL)$_2$(KKL) | 33.9 (7) | 2603.54/2604.02 |
| MSt-176 | (DabW)$_4$(KDabW)$_2$(KDabW) | 15.1 (2) | 2405.87/2406.25 |
| MSt-201 | (DabL)$_4$(KDabL)$_2$(KDabL) | 17.1 (4) | 1894.48/1894.83 |

TABLE 4

4th and 5th generation AMPDs prepared by thioether ligation strategy.

| Compound | Sequence | Yield/mg (%) | MS calc./obsd. |
|---|---|---|---|
| CCS-20 | $(KL)_8(KKLCxKL)_4(KKL)_2KKL$ | 73.0 (11.2) | 6140.28/6140.3 |
| CCS-8 | $(KL)_{16}(KKL)_8(KKLCxKL)_4(KKL)_2KKL$ | 42.0 (5.6) | 11026.94/11026.9 |
| CCS-21 | $(KL)_{16}(KKLCxKL)_8(KKL)_4(KKL)_2KKL$ | 37.0 (5.5) | 12633.04/12634.0 |
| CCS-15 | $(KL)_{32}(KKL)_{16}(KKLCxKL)_8(KKL)_4(KKL)_2KKL$ | 17.0 (2.3) | 22406.35/nd |
| CCS-27 | $(RL)_8(KRLCxRL)_4(KRL)_2KRL$ | 31 (2.4) | 6672.54/6672.0 | nd = not detected;
x denotes a thioether linkage of the cysteine side chain with an acetic acid moiety bound to the N-terminus of the C-terminally neighboring amino acid via an amide bond.

TABLE 5

Peptide dendrimer dimers with 2 amino acid between the branching units prepared by homodimerization via cysteine (C).

| Compound | Sequence | Yield/mg (%) | MS calc./obsd. |
|---|---|---|---|
| CCS-5 dimer | $((KL)_2KKLC)_2$ | 65.3 (8.8) | 1942.66/1943.0 |
| CCS-3 dimer | $((KL)_4(KKL)_2KKLC)_2$ | 22.0 (3.3) | 4385.98/4386.0 |
| CCS-19 dimer | $((RL)_2KRLC)_2$ | 65.0 (9.4) | 2110.74/2111.0 |
| CCS-18 dimer | $((RL)_4(KRL)_2KRLC)_2$ | 64.0 (8.2) | 4778.17/nd |

TABLE 6

3rd generation AMPDs with 1 amino acid between the branching.

| Compound | Sequence | Yield/mg (%) | MS calc./obsd. |
|---|---|---|---|
| MSt-147 | $(L)_8(KK)_4(KL)_2(KK)$ | 31.6 (10) | 2686.67/2687.03 |

TABLE 7

2nd and 3rd generation AMPDs with 2 and 3 amino acid between the branching.

| Compound | Sequence | Yield/mg (%) | MS calc./obsd. |
|---|---|---|---|
| MIS-02 | $(KLL)_4(KKLL)_2(KKLL)$ | 20.5 (2) | 2986.23/2986.23 |
| MIS-03 | $(KKL)_4(KKKL)_2(KKKL)$ | 15.9 (3) | 2881.15/2881.15 |
| MIS-04 | $(LKL)_4(KLKL)_2(KLKL)$ | 44.3 (6) | 2881.15/2881.15 |
| MIS-06 | $(KLL)_8(KKLL)_4(KKLL)_2(KKLL)$ | 6.7 (<1) | 6227.64/6227.64 |
| MIS-08 | $(LKL)_8(KLKL)_4(KLKL)_2(KLKL)$ | 11.5 (<1) | 6227.64/6227.64 |
| YGO-008 | $(KL)_8(KKL)_4(KLKL)_2(KKKL)$ | 10.8 (1) | 4885.64/4887.67 |
| YGO-009 | $(KL)_8(KKL)_4(KLKL)_2(KKLL)$ | 14.7 (2) | 4870.63/4872.66 |
| YGO-010 | $(KL)_8(KKL)_4(KLKL)_2(KKLK)$ | 13.7 (2) | 4885.64/4887.67 |
| YGO-011 | $(KL)_8(KKL)_4(KLKL)_2(KLKL)$ | 15.5 (1) | 4870.63/4872.66 |

TABLE 8

Amino acid sequences, yields and MS analyses of linear AMPs.

| Compound | Sequence | Yield/mg (%) | MS calc./obsd. |
|---|---|---|---|
| MSt-117 (SEQ ID 2) | KLKLKLKLKLKLKL | 9.7 (1) | 1706.34/1706.79 |
| RHe-9 (SEQ ID 1) | (KYKKALKKLAKLL) | 56.4 (9) | 1544.02/1545.20 |

Furthermore, $1^{st}$ or $2^{nd}$ generation peptide dendrimers incorporating cysteine residues were dimerized by formation of a disulfide bond, to give homodimers in good yields (Table 5).

In a last approach 1111 (MSt-147, MSt-148, MSt-149), 3333 (MIS-02, MIS-03, MIS-04, MIS-06, MIS-08), 2233 (YGO-008, YGO-009, YGO-010, YGO-11) AMPDs were created to understand the influence of the number of amino acids between the branching better and to create either more rigid or more flexible AMPDs. The 1111 series has the same topology but different amino acid composition than the previously described 1111 AMPDs active against the Gram-positive bacterium *B. subtilis* but not against the Gram-negative *P. aeruginosa*. Two linear sequences were prepared as references, MSt-117 with alternating charge/hydrophobic motive, and the same amino acid distribution as in MSt-112 and the RHe-9 described in the literature as active against *P. aeruginosa*.

The structure of AMPDs was further modified by attaching hydrophobic alkyl chains, a recurrent element in natural antimicrobial peptides, to second and third generation peptide dendrimers. The solid phase peptide synthesis could be easily extended to attach one copy of the alkyl chain at the core or multiple copies to the N-termini. Carboxylic acids with alkyl chains of six, eight, ten, twelve, sixteen, eighteen and twenty four carbons were used. On total 18 AMPDs with hydrophobic alkyl chains were prepared (Table 9).

Activity of AMPDs Against Human Pathogen *P. aeruginosa* and their Toxicity Against Human Red Blood Cells (hRBC)

All peptides were tested for their activity against *P. aeruginosa* PAO1 in a broth dilution assay (Wiegand, I. et al., 2008, Nat. Protoc., 3, 163-75; Clinical and Laboratory Standards Institute document M7-A7 $7^{th}$ Edition) to determine the MIC (minimal inhibitory concentration) values. The stock solutions of the peptide dendrimers were diluted serially by ⅔ in nutrient LB in 96-well microtiter plates. Bacteria were grown in nutrient LB overnight at 37° C. After dilution the bacteria were added to the peptides and incubated overnight (18-24 h) at 37° C. The MIC values of all synthesized $3^{rd}$ generation AMPDs ranged from highly

TABLE 9

Amino acid sequences, yields and MS analyses of $3^{rd}$ generation AMPDs with hydrophobic side chain.

| Compound | Sequence | Yield/mg (%) | MS calc./obsd. |
|---|---|---|---|
| MSt-260 | $(KL)_4(KKL)_2(KKLKC_6)$ | 23.0 (5) | 2317.17/2316.74 |
| MSt-261 | $(KL)_4(KKL)_2(KKLKC_8)$ | 27.4 (10) | 2345.23/2344.77 |
| MSt-262 | $(KL)_4(KKL)_2(KKLKC_{10})$ | 32.1 (6) | 2373.28/2372.80 |
| MSt-263 | $(KL)_4(KKL)_2(KKLKC_{12})$ | 39.8 (1) | 2401.33/2400.83 |
| MSt-286 | $(KL)_4(KKL)_2(KKLKC_{18})$ | 52.6 (8) | 2485.90/2484.92 |
| MSt-287 | $(KL)_4(KKL)_2(KKLKC_{24})$ | 43.8 (9) | 2569.65/2569.02 |
| MSt-264 | $(KL)_8(KKL)_4(KKL)_2(KKLKC_6)$ | 4.1 (<1) | 4760.50/4759.55 |
| MSt-265 | $(KL)_8(KKL)_4(KKL)_2(KKLKC_8)$ | 12.8 (1) | 4788.55/4787.59 |
| MSt-266 | $(KL)_8(KKL)_4(KKL)_2(KKLKC_{10})$ | 12.1 (1) | 4816.61/4815.62 |
| MSt-267 | $(KL)_8(KKL)_4(KKL)_2(KKLKC_{12})$ | 10.2 (<1) | 4844.66/4843.66 |
| MSt-301 | $(KL)_8(KKL)_4(KKL)_2(KKLKC_{16})$ | 11.4 (1) | 4900.8/4899.7 |
| MSt-284 | $(KL)_8(KKL)_4(KKL)_2(KKLKC_{18})$ | 15.8 (1) | 4928.82/4927.74 |
| MSt-285 | $(KL)_8(KKL)_4(KKL)_2(KKLKC_{24})$ | 24.8 (1) | 5012.98/5012.84 |
| MSt-290 | $(C_6)_4(KKL)_2(KKL)$ | 97.7 (15) | 2483.43/2482.86 |
| MSt-288 | $(C_6KL)_8(KKL)_4(KKL)_2(KKL)$ | 35.9 (3) | 5319.33/5318.98 |

$C_n$ denotes a $C_n$-fatty acid amidated to the side-chain amino group of Lys in the core or coupled to the last main chain amine of Lys.

active (2 µg/mL), in a similar range as polymyxin (2 µg/mL) and tobramyxin (0.5 µg/mL) to active (14 µg/mL) (Table 10). The most potent sequences compromise charged (Lys, Arg, Dab) and hydrophobic (Leu, Trp, Phe) amino acids alternating in each generation. The position of the amino acids between the branching units seems to be optimal if the hydrophobic amino acid is the first counting from C-terminus and the charged one is on the second position. Introducing Ala as additional hydrophobic amino acid reduces activity (MSt-120). The nature of the charged amino acid does not have a large influence in activity but comparing the change of activity with a change of hydrophobic amino acids results in the tendency that Leu is the best, followed by Trp and Phe, whereas with Tyr activity is substantially reduced. Changing the branching unit from Lys to the more rigid Dap (2,3-diaminopropionic acid) does not decrease the activity significantly. Activity is substantially reduced when the charges on the dendrimer are separated from the hydrophobic amino acids so that either the outer sphere or the core part is charged. Also assembling charged or hydrophobic sections between the branching units leads to loss of activity whereas altering L-amino acids to D-amino acids maintains activity leading to the hypothesis that the mechanism of action should not be receptor mediated. Very effective AMPDs were prepared with natural, unnatural and D-amino acids and all of them demonstrated very good activities.

TABLE 10

MIC, MHC and TI values of 3$^{rd}$ generation AMPDs.

| Compound | Sequence | P. aeruginosa PA01 | MHC | TI |
|---|---|---|---|---|
| MSt-112 | (KL)$_8$(KKL)$_4$(KKL)$_2$(KKL) | 2 | 838 | 419 |
| MSt-242 | (RL)$_8$(KRL)$_4$(KRL)$_2$(KRL) | 8 | 86 | 11 |
| MSt-199 | (LK)$_8$(KLK)$_4$(KLK)$_2$(KLK) | 9 | 211 | 23 |
| MSt-114 | (KY)$_8$(KKL)$_4$(KKL)$_2$(KKL) | 2 | 628 | 314 |
| MSt-120 | (LA)$_8$(KLK)$_4$(KLA)$_2$(KKL) | 14 | 584 | 42 |
| MSt-172 | (KW)$_8$(KKW)$_4$(KKW)$_2$(KKW) | 12 | nd | nd |
| MSt-174 | (KF)$_8$(KKF)$_4$(KKF)$_2$(KKF) | 6 | 266 | 44 |
| MSt-136 | (KL)$_8$(BKL)$_4$(BKL)$_2$(BKL) | 2 | 406 | 203 |
| MSt-137 | (RL)$_8$(BRL)$_4$(BRL)$_2$(BRL) | 7 | 25 | 4 |
| MSt-180 | (LL)$_8$(KKK)$_4$(KLL)$_2$(KKK) | 12 | 234 | 20 |
| MSt-181 | (kl)$_8$(kkl)$_4$(kkl)$_2$(kkl) | 4 | 679 | 170 |
| MSt-154 | (kl)$_8$(bkl)$_4$(bkl)$_2$(bkl) | 6 | 370 | 62 |
| MSt-155 | (rl)$_8$(krl)$_4$(krl)$_2$(krl) | 11 | 30 | 3 |
| MSt-156 | (rl)$_8$(brl)$_4$(brl)$_2$(brl) | 10 | 94 | 3 |
| MSt-200 | (DabL)$_8$(KDabL)$_4$(KDabL)$_2$(KDabL) | 3 | 428 | 143 |
| MSt-202 | (DabL)$_8$(KDabW)$_4$(KDabL)$_2$(KDabW) | 2 | 265 | 133 |
| MSt-203 | (DabL)$_8$(KDabL)$_4$(KDabW)$_2$(KDabW) | 2 | 290 | 145 |
| MSt-204 | (DabL)$_8$(KDabW)$_4$(KDabW)$_2$(KDabL) | 3 | 146 | 49 |
| MSt-205 | (DabL)$_8$(KDabW)$_4$(KDabW)$_2$(KDabA) | 3 | 325 | 108 |
| MSt-206 | (DabL)$_8$(KDabW)$_4$(KDabA)$_2$(KDabW) | 3 | 348 | 116 |
| MSt-207 | (DabL)$_8$(KDabA)$_4$(KDabW)$_2$(KDabW) | 8 | 661 | 83 |

To test whether 3$^{rd}$ generation AMPDs could be useful as new antibiotics, they were tested for their haemolytic activity on human red blood cells (hRBC) (Table 10). Minimal haemolytic concentration (MHC) values range from 1 µg/mL to very high 900 µg/mL. The largest influence on the MHC values seems to be the nature of the charged amino acid. Clearly peptides with Lys or Dap are less haemolytic than peptides with Arg. The hydrophobic amino acids Leu, Trp, Tyr or Ala do not have a big influence on the MHCs compared to each other and MHC values are still much higher than their MIC values.

The TI (therapeutic index=MHC (µg/ml)/MIC (µg/ml)) is a useful tool to compare different AMPDs which each other. The higher the TI is the more active and less toxic is the AMPD. Therefore they are very interesting for further development, mechanistic studies and as potential antibacterials. The AMPDs with the highest TI and therefore the peptides with the most potential are MSt-112, MSt-114, MSt-136, MSt-200, MSt-203 and will be further evaluated and discussed. The focus here should be placed on peptide dendrimers with natural amino acids since they should have overall less toxic effects.

Second generation AMPDs were synthesized according to the best motives found with $3^{rd}$ generation AMPDs and evaluated for their MIC and MHC (Table 11). As described previously no significant difference for the activity could be found with changing charged amino acid from Lys to Dab or Arg but the MHC decreased from Lys to Arg to Dab in general. Again no relevant change could be seen by changing the branching unit from Lys to Dap. Substitution of Leu or Trp with Tyr or Ala resulted in a loss of activity. Interestingly the MHC values of the $2^{nd}$ generation AMPDs are much higher compared to their $3^{rd}$ generation analogues maybe due to the smaller number of positively charged residues in the molecule, providing higher TI values. Hence they are promising candidates for further development and investigations especially because of their easier accessibility from SPPS resulting in higher yields.

To fully understand the generational effect $1^{st}$ generation and 0 generation (dipeptide) AMPD analogues of the potent sequences with KL motive between the K branching MSt-112 and MSt-146 were tested for MIC and MHC, too. Those two peptides have low haemolytic activity but are not active against P. aeruginosa (Table 11).

The easily available $1^{st}$ and $2^{nd}$ generation dimers were screened against P. aeruginosa, too (Table 13). With two amino acids between the branching they are either as active (CCS-3) as $2^{nd}$ and $3^{rd}$ generation AMPDs or a little less active (CCS-5, CCS-19, CCS-18).

TABLE 13

Amino acid sequences, yields and MS analyses of peptide dendrimer dimers with 2 amino acid between the branching (prepared by homodimerization via cysteine C).

| Compound | Sequence | P. aeruginosa PA01 | MHC | TI |
| --- | --- | --- | --- | --- |
| CCS-5 dimer | ((KL)$_2$KKLCN)$_2$ | 15 | >250 | >50 |
| CCS-3 dimer | ((KL)$_4$(KKL)$_2$KKLC)$_2$ | 3 | nd | nd |
| CCS-19 dimer | ((RL)$_2$KRLC)$_2$ | 5 | nd | nd |
| CCS-18 dimer | ((RL)$_4$(KRL)$_2$KRLC)$_2$ | 9 | nd | nd |

Previously described 1111 $3^{rd}$ generation AMPDs were active against B. subtilis, Gram-positive bacteria, but not against P. aeruginosa. New 1111 $3^{rd}$ generation AMPDs

TABLE 11

MIC, MHC and TI values of $2^{nd}$ generation AMPDs

| Compound | Sequence | P. aeruginosa PA01 | MHC | TI |
| --- | --- | --- | --- | --- |
| MSt-146 | (KL)$_4$(KKL)$_2$(KKL) | 7 | >1697 | >242 |
| MSt-138 | (KL)$_4$(BKL)$_2$(BKL) | 2 | 1744 | 872 |
| MSt-139 | (RL)$_4$(BRL)$_2$(BRL) | 2 | 969 | 485 |
| MSt-119 | (KKL)$_4$(KKL)$_2$(KKL) | 3 | 677 | 226 |
| MSt-176 | (DabW)$_4$(KDabW)$_2$(KDabW) | 1 | 46 | 46 |
| MSt-201 | (DabL)$_4$(KDabL)$_2$(KDabL) | 5 | >1280 | >256 |

$4^{th}$ and $5^{th}$ generation AMPDs, synthesized via thioether ligation, have slightly lower activities against P. aeruginosa compared to their $2^{nd}$ and $3^{rd}$ generation analogues (Table 12). Due to their larger size the potency to lyse hRBC is quite high, hence the TI is relatively low. Interestingly the Arg variations are less active and more haemolytic revealing the same effect as in $3^{rd}$ generation AMPDs.

were designed after the successful motives from 2222 $3^{rd}$ generation AMPDs and tested in the broth dilution assay and for their haemolytic activity. Only MSt-147 (sequence: (L)$_8$(KK)$_4$(KL)$_2$(KK)) showed activity with MIC of 12 μg/mL and very low haemolysis (1937 μg/mL; TI>160).

Decreasing the number of amino acids between the branching units does not lead to more active AMPDs,

TABLE 12

MIC, MHC and TI values of $4^{th}$ and $5^{th}$ generation AMPDs with 2 amino acid between the branching prepared by thioether ligation.

| Compound | Sequence | P. aeruginosa PA01 | MHC | TI |
| --- | --- | --- | --- | --- |
| CCS-20 | (KL)$_8$(KKLCxKL)$_4$(KKL)$_2$KKL | 3 | >250 | >83 |
| CCS-8 | (KL)$_{16}$(KKL)$_8$(KKLCxKL)$_4$(KKL)$_2$KKL | 9 | 31 | 3 |
| CCS-21 | (KL)$_{16}$(KKLCxKL)$_8$(KKL)$_4$(KKL)$_2$KKL | 13 | 31 | 2 |
| CCS-27 | (RL)$_8$(KRLCxRL)$_4$(KRL)$_2$KRL | 12 | 16 | 1 | x denotes a thioether linkage of the cysteine side chain with an acetic acid moiety bound to the N-terminus of the C-terminally neighboring amino acid via an amide bond.

increasing the number from 2 to 3 amino acids was then tested in the search for more active AMPDs. Four 3333 $2^{nd}$ generation AMPDs, two 3333 $3^{rd}$ generation AMPDs and four 2233 $3^{rd}$ generation AMPDs with the KL motive in alternating positions were tested against *P. aeruginosa*. All sequences showed activities as good as the 2222 $2^{nd}$ and $3^{rd}$ generation AMPDs with the exceptions of MIS-03 with very high Lys-content between branching and MIS-05 with a high Lys content that is separated between the branching points. Those AMPDs possess quite high haemolytic values, which lead to comparable TIs. MIS-06 and MIS-08 3333 $3^{rd}$ generation AMPDs are highly haemolytic due to their high hydrophobicity.

sequences for $C_6$-$C_{12}$ side chains and less activity for $C_{16}$-$C_{24}$ side chains (Table 15). The $2^{nd}$ generation AMPDs MSt-260-MSt-263 gave high MHC values even though the haemolysis increases with longer carbon side chain. Attaching the different carboxylic acids in MSt-264-MSt-267 gave quite low MHC values with the same effect that haemolysis increases with longer carbon side chain. MSt-302, MSt-286, MSt-287, MSt-301, MSt-284, MSt-285 show all haemolysis at low concentrations, therefore having a low TI. Anchoring a $C_6$ or $C_{12}$ carboxylic acid to the N-termini of the $2^{nd}$ and $3^{rd}$ generation AMPDs (MSt-288, MSt-290), hence introducing either 4 or 8 copies of the carbon chain, maintained

TABLE 14

MIC, MHC and TI values of $3^{rd}$ generation AMPDs with 2 and 3 amino acid between the branching.

| Compound | Sequence | P. aeruginosa PA01 | MHC | TI |
|---|---|---|---|---|
| MIS-02 | (KLL)$_4$(KKLL)$_2$(KKLL) | 3 | 15 | 5 |
| MIS-04 | (LKL)$_4$(KLKL)$_2$(KLKL) | 2 | 101 | 51 |
| MIS-06 | (KLL)$_8$(KKLL)$_4$(KKLL)$_2$(KKLL) | 11 | 1 | <1 |
| MIS-08 | (LKL)$_8$(KLKL)$_4$(KLKL)$_2$(KLKL) | 4 | 3 | <1 |
| YGO-008 | (KL)$_8$(KKL)$_4$(KLKL)$_2$(KKKL) | 2 | 525 | 263 |
| YGO-009 | (KL)$_8$(KKL)$_4$(KLKL)$_2$(KKLL) | 2 | 138 | 69 |
| YGO-010 | (KL)$_8$(KKL)$_4$(KLKL)$_2$(KKLK) | 3 | 777 | 259 |
| YGO-011 | (KL)$_8$(KKL)$_4$(KLKL)$_2$(KLKL) | 3 | 490 | 163 |

Attaching a hydrophobic carbon side chain to the core of $2^{nd}$ (MSt-260: $C_6$, MSt-261: $C_8$, MSt-262: $C_{10}$, MSt-263: $C_{12}$, MSt-286: $C_{18}$, MSt-287: $C_{24}$) and $3^{rd}$ (MSt-263: $C_6$, MSt-265: $C_8$, MSt-266: $C_{10}$, MSt-267: $C_{12}$, MSt-301: $C_{16}$, MSt-284 $C_{18}$, MSt-285: $C_{24}$) generation AMPDs with KL motive between the K branching resulted in highly active the activity for AMPDs with C6 carbon chain but lost it for the C12 analogues.

The $3^{rd}$ generation AMPDs with $C_6$-$C_{12}$ carbon side chain in the core and especially the $2^{nd}$ generation analogues with similar TI values are very well suited for further testing with mutants, clinical isolates and mechanistic investigations.

TABLE 15

MIC, MHC and TI values of $3^{rd}$ generation AMPDs with hydrophobic side chain

| Compound | Sequence | P. aeruginosa PA01 | MHC | TI |
|---|---|---|---|---|
| MSt-260 | (KL)$_4$(KKL)$_2$(KKLKC$_6$) | 1 | 1539 | 1539 |
| MSt-261 | (KL)$_4$(KKL)$_2$(KKLKC$_8$) | 1 | 1188 | 1188 |
| MSt-262 | (KL)$_4$(KKL)$_2$(KKLKC$_{10}$) | 1 | 651 | 651 |
| MSt-263 | (KL)$_4$(KKL)$_2$(KKLKC$_{12}$) | 1 | 166 | 166 |
| MSt-264 | (KL)$_8$(KKL)$_4$(KKL)$_2$(KKLKC$_6$) | 1 | 251 | 251 |
| MSt-265 | (KL)$_8$(KKL)$_4$(KKL)$_2$(KKLKC$_8$) | 1 | 267 | 267 |
| MSt-266 | (KL)$_8$(KKL)$_4$(KKL)$_2$(KKLKC$_{10}$) | 1 | 45 | 45 |
| MSt-267 | (KL)$_8$(KKL)$_4$(KKL)$_2$(KKLKC$_{12}$) | 1 | 21 | 21 |
| MSt-301 | (KL)$_8$(KKL)$_4$(KKL)$_2$(KKLKC$_{16}$) | 11 | 6 | <1 |
| MSt-284 | (KL)$_8$(KKL)$_4$(KKL)$_2$(KKLKC$_{18}$) | 9 | 5 | 1 |
| MSt-285 | (KL)$_8$(KKL)$_4$(KKL)$_2$(KKLKC$_{24}$) | 12 | 2 | <1 |
| MSt-286 | (KL)$_4$(KKL)$_2$(KKLKC$_{18}$) | 4 | 2 | 1 |

TABLE 15-continued

MIC, MHC and TI values of 3$^{rd}$ generation
AMPDs with hydrophobic side chain

| Compound | Sequence | P. aeruginosa PAO1 | MHC | TI |
|---|---|---|---|---|
| MSt-288 | (C$_6$KL)$_8$(KKL)$_4$(KKL)$_2$(KKL) | 2 | 1 | 1 |
| MSt-290 | (C$_6$KL)$_4$(KKL)$_2$(KKL)NH$_2$ | 2 | >46 | >23 |

Activity of AMPDs Against *B. subtilis* and *E. coli*

The AMPD library was tested for their antimicrobial activity against *B. subtilis* BR151, a Gram-positive bacterium and *E. coli* DH5α, another Gram-negative bacterium, to cover a broader spectrum of different bacteria. MICs of 3$^{rd}$ generation AMPDs against *B. subtilis* are all rather good with activities ranging from 1-10 µg/mL with MSt-179 being less efficient (Table 16). Therefore no explicit SAR can be established, but clearly the hydrophobic amino acids Ala and Tyr seem to have a significant influence in reducing activity. If 3$^{rd}$ generation AMPDs are used against *E. coli* they show the same trend in efficacy as *P. aeruginosa* (Table 10) but some peptides MSt-199, MSt-114, MSt-120 are considerably less active.

2$^{nd}$ generation AMPDs are neither active on *B. subtilis* nor on *E. coli* whereas they are very potent for *P. aeruginosa* (Table 11). One sequence, MSt-176 with Dab and Trp as amino acids, appears to be the exception. The 2$^{nd}$ generation AMPDs with tryptophan is also active against *B. subtilis* indicating a possible function of the very hydrophobic amino acid for activity against Gram-positive bacteria. Additionally MSt-139 and MSt-119 seem to be slightly efficient with 16 µg/mL and 20 µg/mL.

TABLE 16

MIC, MHC and TI values of 3$^{rd}$ generation AMPDs

| Compound | Sequence | B. subtilis BR151 | TI | E. coli DH5α | TI |
|---|---|---|---|---|---|
| MSt-112 | (KL)$_8$(KKL)$_4$(KKL)$_2$(KKL) | 3 | 279 | 4 | 210 |
| MSt-242 | (RL)$_8$(KRL)$_4$(KRL)$_2$(KRL) | 11 | 8 | 3 | 29 |
| MSt-199 | (LK)$_8$(KLK)$_4$(KLK)$_2$(KLK) | 3 | 70 | 56 | 4 |
| MSt-114 | (KY)$_8$(KKL)$_4$(KKL)$_2$(KKL | 13 | 48 | 34 | 18 |
| MSt-172 | (KW)$_8$(KKW)$_4$(KKW)$_2$(KKW) | 6 | nd | 7 | nd |
| MSt-174 | (KF)$_8$(KKF)$_4$(KKF)$_2$(KKF) | 2 | 133 | 7 | 38 |
| MSt-136 | (KL)$_8$(BKL)$_4$(BKL)$_2$(BKL) | 2 | 203 | 1 | 406 |
| MSt-137 | (RL)$_8$(BRL)$_4$(BRL)$_2$(BRL) | 4 | 6 | 3 | 8 |
| MSt-140 | (KK)$_8$(KKK)$_4$(KLL)$_2$(KLL) | 6 | 10 | >95 | <1 |
| MSt-179 | (KK)$_8$(KLL)$_4$(KKK)$_2$(KLL) | 12 | 10 | >66 | <2 |
| MSt-180 | (LL)$_8$(KKK)$_4$(KLL)$_2$(KKK) | 3 | 78 | >62 | <4 |
| MSt-181 | (kl)$_8$(kkl)$_4$(kkl)$_2$(kkl) | 2 | 340 | 1 | 679 |
| MSt-154 | (kl)$_8$(bkl)$_4$(bkl)$_2$(bkl) | 2 | 185 | 2 | 185 |
| MSt-155 | (rl)$_8$(krl)$_4$(krl)$_2$(krl) | 6 | 5 | 4 | 8 |
| MSt-156 | (rl)$_8$(brl)$_4$(brl)$_2$(brl) | 7 | 13 | 4 | 24 |
| MSt-200 | (DabL)$_8$(KDabL)$_4$(KDabL)$_2$(KDabL) | 2 | 214 | 2 | 214 |
| MSt-202 | (DabL)$_8$(KDabW)$_4$(KDabL)$_2$(KDabW) | 1 | 265 | 1 | 265 |
| MSt-203 | (DabL)$_8$(KDabL)$_4$(KDabW)$_2$(KDabW) | 2 | 145 | 2 | 145 |
| MSt-204 | (DabL)$_8$(KDabW)$_4$(KDabW)$_2$(KDabL) | 2 | 73 | 2 | 73 |
| MSt-205 | (DabL)$_8$(KDabW)$_4$(KDabW)$_2$(KDabA) | 2 | 163 | 2 | 163 |
| MSt-206 | (DabL)$_8$(KDabW)$_4$(KDabA)$_2$(KDabW) | 2 | 174 | 2 | 174 |
| MSt-207 | (DabL)$_8$(KDabA)$_4$(KDabW)$_2$(KDabW) | 7 | 94 | 21 | 31 |

TABLE 17

MIC, MHC and TI values of $2^{nd}$ generation AMPDs

| Compound | Sequence | B. subtilis BR151 | TI | E. coli DH5α | TI |
|---|---|---|---|---|---|
| MSt-139 | (RL)$_4$(BRL)$_2$(BRL) | 16 | 61 | 17 | 57 |
| MSt-176 | (DabW)$_4$(KDabW)$_2$(KDabW) | 1 | 46 | 3 | 15 |

The larger $4^{th}$ and $5^{th}$ generation peptide dendrimers are a lot more active against *B. subtilis* and *E. coli* than $2^{nd}$ generation but in the same range as $3^{rd}$ generation analogues (Table 18). Due to low MHC values their TI is lower than for $3^{rd}$ generation AMPDs. MIC data for dimers are in table 19.

TABLE 18

MIC, MHC and TI values of of $4^{th}$ and $5^{th}$ generation AMPDs with 2 amino acid between the branching prepared by thioether ligation.

| Compound | Sequence | B. subtilis BR151 | TI | E. coli DH5α | TI |
|---|---|---|---|---|---|
| CCS-20 | (KL)$_8$(KKLCxKL)$_4$(KKL)$_2$KKL | 10 | >25 | 4 | >63 |
| CCS-8 | (KL)$_{16}$(KKL)$_8$(KKLCxKL)$_4$(KKL)$_2$KKL | 20 | 2 | 4 | 8 |
| CCS-21 | (KL)$_{16}$(KKLCxKL)$_8$(KKL)$_4$(KKL)$_2$KKL | 30 | 1 | 4 | 8 |
| CCS-15 | (KL)$_{32}$(KKL)$_{16}$(KKLCxKL)$_8$(KKL)$_4$(KKL)$_2$KKL | 26 | 0.3 | 8 | 1 | x denotes a thioether linkage of the cysteine side chain with an acetic acid moiety bound to the N-terminus of the C-terminally neighboring amino acid via an amide bond.

TABLE 19

Amino acid sequences, yields and MS analysis of peptide dendrimer dimers with 2 amino acid between the branching (prepared by homodimerization via cysteine C).

| Compound | Sequence | B. subtilis BR151 | TI | E. coli DH5α | TI |
|---|---|---|---|---|---|
| CCS-3 dimer | ((KL)$_4$(KKL)$_2$KKLC)$_2$ | 4 | nd | 4 | nd |
| CCS-18 dimer | ((RL)$_4$(KRL)$_2$KRLC)$_2$ | 9 | nd | 13 | nd |

Previously reported 1111 $3^{rd}$ generation AMPDs are active against *B. subtilis* at concentrations of 2-5 µg/mL. MSt-148 and MSt-149 with the same topology but only Lys and Leu at different positions are still active but less potent (Table 20). Even though they are easily and fast synthesized with good yields, which would make them ideal peptides for upscaling, so far they did not show the same potential as other peptide dendrimers for Gram-negative and Gram-positive bacteria.

TABLE 20

MIC and TI values of 1111 $3^{rd}$ generation AMPDs (with 1 amino acid between the branching)

| Compound | Sequence | B. subtilis BR151 | TI | E. coli DH5α | TI |
|---|---|---|---|---|---|
| MSt-148 | (K)$_8$(KK)$_4$(KL)$_2$(KL)NH$_2$ | 12 | 75 | >90 | <10 |
| MSt-149 | (L)$_8$(KL)$_4$(KK)$_2$(KK)NH$_2$ | 8 | >224 | >90 | <20 |

3333 $2^{nd}$ and $3^{rd}$ generation AMPDs MIS-02, MIS-03, MIS-04, MIS-06 and MIS-08 (Table 21) are all very effective against B. subtilis with activities of 0.5 to 6 µg/mL, even better than against P. aeruginosa with the exception of MIS-05. They are all very haemolytic, hence their TI is very low except for MIS-04. MIS-04 would be a good candidate for further development and investigations for Gram-positive bacteria in general. 2233 $3^{rd}$ generation AMPDs (YGO-008, YGO-009, YGO-010, YGO-011) were only tested for E. coli but showed excellent activities there with 2-3 µg/mL (Table 21), which are in the same range as with P. aeruginosa (Table 14).

TABLE 21

MIC, MHC and TI values of $3^{rd}$ generation AMPDs with 2 and 3 amino acid between the branching

| Compound | Sequence | B. subtilis BR151 | TI | E. coli DH5α | TI |
|---|---|---|---|---|---|
| MIS-02 | (KLL)$_4$(KKLL)$_2$(KKLL) | 1 | 15 | nd | nd |
| MIS-03 | (KKL)$_4$(KKKL)$_2$(KKKL) | 6 | 36 | nd | nd |
| MIS-04 | (LKL)$_4$(KLKL)$_2$(KLKL) | 0.5 | 202 | nd | nd |
| MIS-06 | (KLL)$_8$(KKLL)$_4$(KKLL)$_2$(KKLL) | 4 | <1 | nd | nd |
| MIS-08 | (LKL)$_8$(KLKL)$_4$(KLKL)$_2$(KLKL) | 0.5 | 6 | nd | nd |
| YGO-008 | (KL)$_8$(KKL)$_4$(KLKL)$_2$(KKKL) | nd | nd | 2 | 263 |
| YGO-009 | (KL)$_8$(KKL)$_4$(KLKL)$_2$(KKLL) | nd | nd | 2 | 69 |
| YGO-010 | (KL)$_8$(KKL)$_4$(KLKL)$_2$(KKLK) | nd | nd | 2 | 389 |
| YGO-011 | (KL)$_8$(KKL)$_4$(KLKL)$_2$(KLKL) | nd | nd | 3 | 163 |

The two linear peptides which were chosen for comparative reasons MSt-117 and RHe-9, display the same tendency for activity with B. subtilis and E. coli (Table 22) compared to P. aeruginosa (Table 12). MSt-117 is much less potent than $3^{rd}$ generation AMPDs and is very haemolytic. RHe-9 is highly potent on both gram positive and negative bacteria and not haemolytic, resulting in a comparable TI to $3^{rd}$ generation AMPDs.

TABLE 22

MIC, MHC and TI values of linear AMPs

| Compound | Sequence | B. subtilis BR151 | TI | E. coli DH5α | TI |
|---|---|---|---|---|---|
| MSt-117 (SEQ ID 2) | KLKLKLKLKLKLKL | 14 | <1 | 13 | <1 |
| RHe-9 (SEQ ID 1) | (KYKKALKKLAKLL) | 4 | 105 | <1 | >419 |

In Table 23 $2^{nd}$ and $3^{rd}$ generation AMPDs with a hydrophobic carbon side chain at the C-terminus of the peptide dendrimers are listed against B. subtilis and E. coli. All sequences are very potent for both bacteria with MICs of 1 to 6 µg/mL. There are only a few exceptions like MSt-260 with a $C_6$ carbon chain, MSt-302 and MSt-301 with a $C_{16}$ carbon chain, MSt-285 and MSt-287 with a $C_{24}$ carbon chain at the N-termini, all highly hydrophobic and not very active on P. aeruginosa either (Table 15). Nevertheless there are still very potent AMPDs like MSt-261, MSt-262, MSt-263, MSt-264, MSt-265, MSt-266, MSt-267, MSt-284, MSt-286, MSt-288, MSt-290 which are more haemolytic the more hydrophobic they get resulting in a lower TI (Table 23) but still higher than 100 in potent cases. Hence MSt-261, MSt-262, MSt-263, MSt-264, MSt-265, MSt-266, MSt-267 are very effective AMPDs against all three tested bacteria and do have great potential.

TABLE 23

MIC and TI values of $2^{nd}$ and $3^{rd}$ generation AMPDs with one, four or eight hydrophobic side chains

| Compound | Sequence | B. subtilis BR151 | TI | E. coli DH5α | TI |
|---|---|---|---|---|---|
| MSt-260 | $(KL)_4(KKL)_2(KKLKC_6)$ | 20 | 77 | 2 | 770 |
| MSt-261 | $(KL)_4(KKL)_2(KKLKC_8)$ | 4 | 297 | 1 | 1188 |
| MSt-262 | $(KL)_4(KKL)_2(KKLKC_{10})$ | 2 | 326 | 1 | 651 |
| MSt-263 | $(KL)_4(KKL)_2(KKLKC_{12})$ | 2 | 83 | 1 | 166 |
| MSt-302 | $(KL)_4(KKL)_2(KKLKC_{16})$ | nd | nd | 12 | 1 |
| MSt-264 | $(KL)_8(KKL)_4(KKL)_2(KKLKC_6)$ | 5 | 50 | 1 | 251 |
| MSt-265 | $(KL)_8(KKL)_4(KKL)_2(KKLKC_8)$ | 4 | 67 | 1 | 267 |
| MSt-266 | $(KL)_8(KKL)_4(KKL)_2(KKLKC_{10})$ | 4 | 11 | 1 | 45 |
| MSt-267 | $(KL)_8(KKL)_4(KKL)_2(KKLKC_{12})$ | 4 | 5 | 1 | 21 |
| MSt-301 | $(KL)_8(KKL)_4(KKL)_2(KKLKC_{16})$ | nd | nd | 8 | 1 |
| MSt-284 | $(KL)_8(KKL)_4(KKL)_2(KKLKC_{18})$ | 6 | 1 | 3 | 2 |
| MSt-285 | $(KL)_8(KKL)_4(KKL)_2(KKLKC_{24})$ | 16 | <1 | 5 | <1 |
| MSt-286 | $(KL)_4(KKL)_2(KKLKC_{18})$ | 4 | <1 | 3 | <1 |
| MSt-287 | $(KL)_4(KKL)_2(KKLKC_{24})$ | 26 | <1 | 13 | <1 |
| MSt-288 | $(C_6KL)_8(KKL)_4(KKL)_2(KKL)$ | 1 | 1 | 5 | <1 |
| MSt-290 | $(C_6KL)_4(KKL)_2(KKL)$ | 1 | >46 | 1 | >46 |

TABLE 24

Results for G2 AMPDs with/without a C10 alkylcarboxylic acid chain against PAO1 in MH medium and in the presence of human serum - G2 without alkylcarboxylic acid chain are not active in MH although show activity in LB;

| Compound | Sequence | MIC (MH) (µg/ml) | MIC (MH + 30% human serum (µg/ml) |
|---|---|---|---|
| G3KL | $(KL)_8(KKL)_4(KKL)_2(KKL)$ | 4 | 4 |
| G2KLC10 | $(KL)_4(KKL)_2(KKL-CO(CH_2)_8CH_3)$ | 4 | 8-16 |
| TNS-122 | $(OrnF)_4(KDabL)_2(KKLK-CO(CH_2)_8CH_3)$ | 2 | 8 |
| TNS-123 | $(OrnL)_4(KDabF)_2(KKLK-CO(CH_2)_8CH_3)$ | 2 | 8-16 |
| TNS-124 | $(RF)_4(KDabL)_2(KKLK-CO(CH_2)_8CH_3)$ | 4-8 | 16-32 |
| Polymyxin B | | 2 | 4 |

TABLE 25

MIC values against PAO1 of compounds comprising Dab in MH medium and compounds without DAB. Results are for two independent experiments done in triplicate (MH medium, 12-18 h)

| Substance | PAO1 | PT1482 (A-) | PT1485 (AB-) |
|---|---|---|---|
| G2KL | >64 | >64 | 16 |
| TNS33 | >64 | >64 | 8 |
| TNS34 | >64 | >64 | 4 |
| TNS37 | >64 | 64 | 4 |
| G3KL | 4 | 4 | 4 |
| G2KLC10 | 8 | 4 | 4 |
| TNS122 | 4 (8) | 4 | 2-4 |
| TNS123 | 4-8 | 4 | 4 |
| TNS124 | 8 | 8 | 4 |
| Polymyxin B | 1 | 1 | <1 |

TABLE 26

MIC values against *P. aeruginosa* MDR clinical isolates, *S. aureus* and *A. baumannii* of compounds comprising Dab in MH medium and compounds without DAB. Results are for two independent experiments done in triplicate (MH medium, 12-18 h)

| Substance | *P. aeruginosa* MDR clinical isolates | | | | *S. aureus* | *A. baumannii* |
|---|---|---|---|---|---|---|
| | PEJ2.6 | PEJ9.1 | ZEM1A | ZEM9A | COL | ATCC19606 |
| G2KL | >64 | >64 | >64 | >64 | >64 | >64 |
| TNS33 | >64 | >64 | >64 | >64 | >64 | >64 |
| TNS34 | >64 | >64 | >64 | >64 | >64 | >64 |
| TNS37 | 64 | >64 | >64 | >64 | 64-32 | >64 |
| G3KL | 16 | 64 | 4 | 32-64 | >64 | 8-16 |
| G2KLC10 | 8 | 64 | 4 | 16-8 | 64 | 16 |
| TNS122 | 4 | 32 | 4 | 8 | 8-16 | 8-16 |
| TNS123 | 16 | >64 | 4 | 8 | 32-64 | 32 |
| TNS124 | 8 | 32 | 4-8 | 16-32 | 8 | 8-16 |
| Polymyxin B | 1 | 2 | <1 | 8 | 64 | <1 |

TABLE 27

MIC values of G3KL against drug resistant strains of *P. aeruginosa* and *A. baumannii*

| Number | ssb-no | Species | Resistance Mechanism | Polypropilene plates | |
|---|---|---|---|---|---|
| | | | | MIC | MBC |
| 2172421 | 5202.28 | *Acinetobacter baumannii* | OXA-23 | 4 | 4 |
| 2203591 | 5209.70 | *Acinetobacter baumannii* complex | — | 4 | 8 |
| 2310924 | 5505.26 | *Acinetobacter baumannii* complex | — | 8 | 8 |
| 2266064 | 5402.35 | *Acinetobacter baumannii* complex | CarbaR unknown mechanism | 8 | 8 |
| 2303905 | 5502.38 | *Acinetobacter baumannii* complex | — | 4 | 4 |
| 2327362 | 5511.70 | *Acinetobacter baumannii* complex | — | 4 | 4 |
| 2321336 | 5509.39 | *Acinetobacter baumannii* complex | CarbaR unknown mechanism | 4 | 4 |
| 2318355 | 5508.22 | *Acinetobacter baumannii* complex | CarbaR unknown mechanism | 8 | 8 |
| 2319515 | 5508.04 | *Acinetobacter baumannii* complex | — | 8 | 8 |
| 2317747 | 5507.51 | *Acinetobacter baumannii* complex | — | 4 | 4 |
| 2343324 | 5605.47 | *Acinetobacter baumannii* complex | — | 8 | 8 |
| 2316948-2 | 5507.38 | *Acinetobacter baumannii* complex | — | 8 | 8 |
| 2316948-1 | 5507.37 | *Acinetobacter baumannii* complex | — | 8 | 8 |
| 2332122 | 5601.49 | *Acinetobacter baumannii* complex | — | 8 | 8 |
| Cleveland | | *Pseudomonas aeruginosa* | VIM-1 | 4 | 4 |
| 2267476 | 5402.48 | *Pseudomonas aeruginosa* | CarbaR unknown mechanism | 4 | 4 |
| 2280037 | 5406.42 | *Pseudomonas aeruginosa* | CarbaR unknown mechanism | | |
| 2280037-I | | *Pseudomonas aeruginosa* | | 8 | 8 |
| 2280037-II | | *Pseudomonas aeruginosa* | | 4 | 4 |
| 2296294 | 5411.48 | *Pseudomonas aeruginosa* | — | 8 | 8 |
| 2306440 | 5503.09 | *Pseudomonas aeruginosa* | — | 8 | 8 |
| 2256279 | 5311.75 | *Pseudomonas aeruginosa* | CarbaR unknown mechanism | 8 | 8 |
| 2291604 | 5410.12 | *Pseudomonas aeruginosa* | — | 16 | 16 |
| 2307544 | 5503.50 | *Pseudomonas aeruginosa* | — | 8 | 8 |
| 2226680 | 5304.11 | *Pseudomonas aeruginosa* | — | 4 | 4 |
| 2223278 | 5302.68 | *Pseudomonas aeruginosa* | — | 8 | 8 |
| 2221712 | 5302.56 | *Pseudomonas aeruginosa* | — | 2 | 32 |
| 2184627 | 5205.17 | *Pseudomonas aeruginosa* | — | 8 | 8 |
| 2186565 | 5205.63 | *Pseudomonas aeruginosa* | — | 8 | 8 |
| C-7-7 | | *A. baumannii* | OXA-58 | 16 | 16 |
| VA645/00 | | *A. baumannii* | OXA-24 | 8 | 8 |
| O3C03 | | *A. baumannii* | OXA-23 | 8 | 8 |
| O2C03 | | *A. baumannii* | OXA-23 | 8 | 8 |
| C-15-35 | | *A. baumannii* | OXA-58 | 8 | 8 |
| C-14-275 | | *A. baumannii* | OXA-58 | 8 | 8 |
| O3C10 | | *A. baumannii* | OXA-23 | 8 | 8 |
| C-14-336 | | *A. baumannii* | OXA-58 | 8 | 8 |
| C-13-373 | | *A. baumannii* | OXA-23 | 8 | 8 |
| C-07-31 | | *A. baumannii* | OXA-58 | 16 | 16 |

TABLE 28

MIC values of G3KL against several Drug resistant pathogens

| Number | Species | Resistance Mechanism | MIC | MBC |
|---|---|---|---|---|
| 2247421 | *Klebsiella pneumoniae* | NDM; OXA-48 | >32 | — |
| 2081507 | *Klebsiella pneumoniae* | NDM CTX-M-Gr1; SHV-type | 16 | >32 |
| 2218824 | *Klebsiella pneumoniae* | VIM | >32 | — |
| 2238765 | *Klebsiella pneumoniae* | OXA-48; CTX-M-type | >32 | — |
| QK416 | *Klebsiella pneumoniae* | KPC | >32 | — |
| QK418 | *Klebsiella pneumoniae* | — | 4 | 8 |
| 2298819 | *Klebsiella pneumoniae* | KPC | >64 | — |
| 2218821 | *Klebsiella pneumoniae* | KPC | >64 | — |
| 2218822 | *Klebsiella pneumoniae* | OXA-48 | >64 | — |
| 2218823 | *Klebsiella pneumoniae* | KPC | >64 | — |
| 2218825 | *Klebsiella pneumoniae* | NDM | 16 | 16 |
| 2218826 | *Klebsiella pneumoniae* | — | 32 | 32 |
| 2218827 | *Klebsiella pneumoniae* | NDM | 16 | 32 |
| JF5969 | *Klebsiella pneumoniae* | DHA | >64 | |
| 2262461 | *Klebsiella oxytoca* | CTX-M-15-like | 8 | 8 |
| 2058665 | *Escherichia coli* | NDM | >32 | — |
| QK8 | *Escherichia coli* | — | >32 | — |
| 2113003 | *Escherichia coli* | CTX-M-Gr1 | >32 | — |
| 2081272 | *Escherichia coli* | DHA, Temall | >32 | — |
| 2152061 | *Escherichia coli* | CMY-2, CTX-M-15 | >32 | — |
| 2266358 II | *Escherichia coli* | OXA-48, CTX-M-1 | 8 | 64 |
| 804135 n4 | *Citrobacter freundii* | NDM; OXA-48; CTX-M-15 | 4 | 4 |
| LA12095039 | *Citrobacter koseri* | CTX-M-15, CMY-4; TEM-1-like | 8 | 8 |
| LA12095041 | *Citrobacter koseri* | CTX-M-15, CMY-4; TEM-1-like | 4 | 4 |
| 2218820 | *Enterobacter cloacae* | NDM; TEM-type | 8 | 8 |
| 2262494 | *Enterobacter cloacae* | — | 8 | 16 |
| 2218828 | *Enterobacter aerogenes* | — | 32 | 32 |
| 804133 N6 | *Proteus mirabilis* | CMY-2 | >32 | — |
| VB1248 | *Proteus mirabilis* | VEB-6 | >32 | — |
| 2198242 | *Salmonela* Kentucky | OXA-48; VEB-8 | 8 | 8 |
| 2172421 | *Acinetobacter baumannii* | OXA-23 | 8 | 8 |
| 2203591 | *Acinetobacter baumannii* complex | — | 4 | 8 |
| 2310924 | *Acinetobacter baumannii* complex | — | 8 | 8 |
| 2266064 | *Acinetobacter baumannii* complex | CarbaR unknown mechanism | 8 | 8 |
| 2303905 | *Acinetobacter baumannii* complex | — | 4 | 4 |
| 2327362 | *Acinetobacter baumannii* complex | — | 4 | 4 |
| 2321336 | *Acinetobacter baumannii* complex | CarbaR unknown mechanism | 4 | 4 |
| 2318355 | *Acinetobacter baumannii* complex | CarbaR unknown mechanism | 16 | 16 |
| 2310515 | *Acinetobacter baumannii* complex | — | 8 | 8 |
| Cleaveland | *Pseudomonas aeruginosa* | VIM-1 | 4 | 4 |
| 2267476 | *Pseudomonas aeruginosa* | CarbaR unknown mechanism | 4 | 8 |
| 2280037 | *Pseudomonas aeruginosa* | CarbaR unknown mechanism | 4 | 8 |
| 2296294 | *Pseudomonas aeruginosa* | — | 4 | 8 |
| 2306440 | *Pseudomonas aeruginosa* | — | 8 | 8 |
| 2256279 | *Pseudomonas aeruginosa* | CarbaR unknown mechanism | 4 | 4 |
| 2291604 | *Pseudomonas aeruginosa* | — | 16 | 32 |
| 2307544 | *Pseudomonas aeruginosa* | — | 4 | 4 |

Minimal Inhibitory Concentration of AMPDs Against Clinical *P. aeruginosa*, *S. aureus*, *A. baumannii* Isolates and Resistance Analysis Ten of the most promising compounds (FIG. 5) were tested for their efficiency against four clinical isolates of *P. aeruginosa* (ZEM9.A, ZEM1.A, PEJ2.6, PEJ9.1), one *S. aureus* (COL, MRSA reference strain) and one *A. baumannii* strain. For the experiments in Genève the peptide dendrimers and reference compounds (polymyxin) were dissolved in PBS and the assay was carried out in Müller-Hinton (MH) broth with a two-fold dilution.

All AMPDs tested against the four *P. aeruginosa* clinical isolates showed activities below 20 µg/mL, only the $3^{rd}$ generation dendrimer with Arg instead of Lys (MSt-242) was slightly higher against *P. aeruginosa* ZEM9.A. Those clinical isolates are resistant to some widely used antibiotics like Imipenem, Meropenem, Gentamicin, Trimethoprim and Sulfonamides and therefore hold great potential as substitutes. Those AMPDs display activities between 6-19 µg/mL against *A. baumannii* another pathogenic Gram-negative bacterium. *S. aureus*, a Gram-positive bacterium that can be problematic once developed a resistance, was also included in the assay and the $2^{nd}$ generation AMPDs MSt-176, MSt-263 and the $3^{rd}$ generation AMPD MSt-242 had an activity lower than 20 µg/mL.

Stability of AMPDs in Human Serum

Peptide dendrimers were previously described as proteolytically very stable compounds compared to their linear analogues. Due to their branching points cleavage sites are less accessible for proteases. The number of amino acids between the branching units is also important for better stability.

The peptides were mixed with human serum (previously diluted with DMEM) to a final peptide concentration of 100 µM to determine the stability of AMPDs toward proteases and incubated at 37° C. for 0, 1, 6, or 24 hours. After precipitation of proteins with TCA, the solution was analyzed by analytical RP-UPLC. Over a period of 24 hours the signal of the AMPDs MSt-112 and MSt-181 remains constant, hence no or only a little proteolysis took place. Whereas the signal of the linear peptide RHe-9 (SEQ ID 1) completely disappeared, suggesting full proteolysis of this peptide over 24 hours. Interestingly, the all L-enantiomer MSt-112 has the same behavior than all D-enantiomer MSt-181 indicating that all L-enantiomer AMPDs are already stable enough and the possible toxicity of the all D-enantiomers can be avoided. AMPDs MSt-114, MSt-136, MSt-138, MSt-139, MSt-140 and MSt-176 were also checked for their stability. MSt-136, MSt-138 and MSt-139 were stable for 24 h, peptide dendrimers MSt-114 and MSt-139 however showed some but not complete degradation. The stability of peptide dendrimers with only natural L-amino acids in human serum represents a significant advantage in the development of therapeutic agents compared to peptides with unnatural building blocks.

Another experiment that demonstrates the stability of AMPDs is the incubation of the peptide with a bacterial suspension of *P. aeruginosa* PAO1. Bacteria were grown in LB overnight and diluted to $OD_{600}$=0.2. After addition of the peptides to a concentration of 100 μM the samples were incubated for 0, 1, 6, 9, 24 hours at 37° C. After heating the suspension to 95° C. for 5 min and centrifugation the solution was subjected to UPLC and the remaining peptide was analyzed by using Chromeleon software. The analysis shows that even after 24 h the bacterial suspension did not degrade the AMPDs MSt-112, MSt-114, MSt-136, MSt-138, MSt-139, MSt-140, MSt-176 and MSt-181 while RHe-9 (SEQ ID 1) was not detectable after 9 hours.

Interaction of AMPDs with Large Unilamellar Vesicles (LUVs) as Model Systems for Eukaryotic and Prokaryotic Cell Membranes Bacterial membranes contain relatively large amounts of exposed anionic lipids, while the outer leaflet of the membranes of plants and animals is composed mainly of lipids with no net charge. The charge composition of such membranes can be mimicked with phospholipid vesicles. Large unilamellar vesicles (LUVs) composed of the neutral phospholipid with PC (phosphatidyl choline) or with PG (phosphatidyl glycerol) with negative charges were prepared encapsulating 5(6)-carboxyfluorescein (CF). These LUVs were treated with AMPDs MSt-112, MSt-114, MSt-176 and MSt-181 and inactive peptide dendrimers MSt-138, MSt-139 at different peptide concentrations. Addition of active $3^{rd}$ generation AMPD MSt-112 at 50 s to a solution of LUVs from phosphatidylglycerol results in an increase of fluorescence. The higher the concentration of MSt-112 the higher is the CF leakage (FIG. 6A). Using the inactive MSt-113 on phosphatidylglycerol LUVs shows no immediate increase even at 100 μg/mL and only some negligible leakage with advanced time (FIG. 6B). All other active AMPDs (MSt-114, MSt-176 and MSt-181) and Polymyxin, a known membrane disruptor, display the same immediate leakage of CF upon addition of the peptide. MSt-138 and Tobramycin, an antibiotic that interferes with the biosynthesis of proteins in the bacteria, do not show release of CF as well as MSt-113, whereas MSt-139 releases CF but not as much as the active AMPDs at the same concentration. Overall the active AMPDs interact with the negatively charged membrane and release the CF. Hence membrane permeabilization and disrupting seems very likely, whereas inactive peptides do not or only partially interfere with the lipids of the LUVs.

If MSt-112 is subjected to a LUV solution from phosphatidylcholine no CF is released even at very high concentrations compared to MIC value (FIG. 7A). All other active AMPDs and Polymyxin behave in the same way whereas MSt-176, the very hydrophobic $2^{nd}$ generation peptide, that is much more haemolytic than the others (Table 11), induced CF release. MSt-113 (FIG. 7B), MSt-138 and MSt-139 and Tobramycin showed the same behavior with no CF release.

If a carbon side chain is incorporated to $2^{nd}$ (MSt-260, MSt-261, MSt-262, MSt-263) or $3^{rd}$ generation (MSt-264, MSt-265, MSt-266, MSt-267) AMPD, CF leaks immediately after addition of the peptide dendrimer to phosphatidylglycerol LUVs solution at 50 s at various concentrations in the same way as MSt-112 (shown in FIG. 8A for MSt-260). The only difference is in the intensities of $2^{nd}$ and $3^{rd}$ generation AMPDs at variable concentrations. With one additional generation the fluorescence increase at the same concentration is higher. Consequently all of those AMPDs interact with the negatively charged model membrane, disturbing membrane integrity to allow CF leakage. If phosphatidylcholine, a model membrane with no net charge, is used, CF release is only observed with high peptide dendrimer concentrations (FIG. 8B for MSt-260). With increasing number of carbon atoms in the hydrophobic side chain the intensity of the CF leakage is higher. This is in accordance with the lysis of hRBC, where a longer carbon chain induces haemolysis at lower concentrations.

Killing Kinetics

In order to determine the killing kinetics of AMPDs the amount of living bacteria was measured as a function of time after incubation with the AMPDs. An assay with WST-8 to detect living bacteria was used (Roehm, N. W. et al., 1991, J. Immunol. Methods, 142, 257-265; Chang, J.-Y. et al., 1991 Anal. Biochem, 197, 52-58). Thus *P. aeruginosa* was incubated with AMPDs or inactive peptide dendrimers at a concentration of 25 μg/mL for 0, 1, 3, 6, 8 and 24 hours before measuring the absorbance of formazan at 450 nm which is proportional to living bacteria. FIG. 9 shows the bacterial survival over 24 hours. All AMPDs (MSt-112, MSt-176, MSt-181) displayed the same behaviour directly after addition of the peptide dendrimers, where at least 60% of bacteria are still living. Most AMPDs require 3 hours for complete killing. Compared to the reference substances Polymyxin and Tobramycin that kill *P. aeruginosa* immediately, AMPDs seem to act more slowly. As expected the inactive peptide dendrimers MSt-138 and MSt-139 are not able to reduce the amount of bacteria after 24 hours. The performance of the AMPD MSt-114, which is quite potent, differs from the other AMPDs. Only after 24 hours almost all bacteria are killed.

Comparing the $2^{nd}$ and $3^{rd}$ generation AMPDs with the $C_8$ (MSt-261 and MSt-263) or $C_{12}$ (MSt-265 and MSt-267) carbon side chain in the core with MSt-112 reveals a different behaviour; immediately after addition 60% of bacteria are killed and after one hour the number is already reduced to zero. Therefore attaching a carbon side chain seems to change the kinetics of killing. This assay gives a first indication of killing kinetics for the AMPDs but more experiments are necessary to determine the time required for in vitro killing.

Resistance Assay

For an initial estimation of how fast resistances could arise with AMPDs the MIC was repeated for 15 days in a row and determined each day. After obtaining the MIC value in usual broth dilution assay the bacteria (*B. subtilis*) from the ½ MIC well were incubated for 2-5 hours and the dilution assay was repeated. This procedure was realized for 15 days and the MICs of each day compared. In case of an increase of the MIC, it is indicative for a resistance against the AMPDs. In this experiment the very potent MSt-112, MSt-176, MSt-181 did not have a significant change of their MIC values over 15 days whereas the less potent MSt-114, MSt-139, MSt-140 displayed a loss in activity already after 5 to 10 days.

AMPD Toxicity-Preliminary In-Vivo Experiments with Rats

The compounds MSt-112, a $3^{rd}$ generation AMPD with KL motive, MSt-181 its D-enantiomer analogue, MSt-242, a the $3^{rd}$ generation with RL motive, and MSt-114 with Tyr instead of Lys in the $3^{rd}$ generation were used for in vivo experiments with male wistar rats to assess their toxicity. These compounds were selected due to their high potencies and high MHCs values, which are at least 10 times higher than their activities. Each compound (concentration of 2 mg/kg) was applied to two rats by intravenous injection into the tail vein to observe if the AMPDs are well tolerated or may cause adverse effects. The concentration used was approx. 5-10 times higher than the MICs. No visible effect could be observed and the rats behaved normal after injection of AMPDs MSt-112 and MSt-242. Injection of AMPDs MSt-114 and MSt-181 resulted in slightly bluish extremities which subsided after approx. 5 min. The behaviour of the rats was normal. Monitoring the rats for 2 days showed no abnormalities in their behaviour and the survival rate was 100%. The control rats injected with either 500 μL of PBS or no injection also showed normal behaviour during two days and had a 100% survival rate. Therefore it seems that rats tolerate AMPDs very well, without visible site effects or even casualties.

CONCLUSIONS

After screening a peptide dendrimer library of 78 compounds against the pathogenic Gram-negative bacterium *P. aeruginosa*, several dendrimers with high activity and low haemolysis of red blood cells could be found. Some are $2^{nd}$ generation peptide dendrimers (MSt-138, MSt-139, MSt-176) others $3^{rd}$ generation ones MSt-112, MSt-181, MSt-242). Additional screening against the Gram-negative *E. coli* and the Gram-positive *B. subtilis* revealed a broader efficacy of MSt-176, MSt-112, MSt-181 and MSt-242. In further studies with clinical isolates of *P. aeruginosa*, that show resistance against common antibiotics, the $2^{nd}$ generation AMPD MSt-176 and the 3rd generation AMPDs MSt-112, MSt-181 and MSt-242 were effective, too. Against the Gram-negative *A. baumannii* they showed some activity.

Attaching alkyl chains to the core, ranging from $C_6$ to $C_{12}$, to second generation AMPDs produced antibacterials with broader spectrum. These sequences were also efficient against *A. baumannii* and hospital resistant strains. Activities of the best compounds are in the same range as the very potent Polymyxin, which is used as last resource in clinic. Advantages of AMPDs when compared to other peptidic compounds are their low toxicity to hRBC, slow degradation by proteases, and the presence of only natural amino acids. The evidence collected points as well to a mode of action where the cell membrane gets disrupted, cells lyse and the bacteria die. Experiments with *P. aeruginosa* mutants, LUVs and killing kinetics point towards cell membrane disruption where LPS structure does not hinder the peptide dendrimers. Therefore it is unlikely that treatment with AMPDs will lead to a fast development of resistance.

Our new class of antimicrobials, AMPDs with 2 or 3 amino acids between the branching units, are a non-toxic, stable system which is easily synthesized in good yields and is highly efficient against human pathogens in vitro. Active sequences can be third generation, second generation with or without alkyl chain. The peptide dendrimers can be prepared on solid support with only one purification step or can be assembled in solution from two dendrimers of lower generation (see ccs-20) providing the third generation dendrimer in very good yield. The structure plasticity is a unique feature of our peptide dendrimers not found in linear or cyclic counterparts and confer an advantage regarding further optimization to obtain compounds with the desired pharmacokinetics. The in vitro experiments described set now the framework for the in vivo experiments that will be the step to follow in the goal to develop therapeutic agents based on peptide dendrimers.

The antimicrobial activity in the presence of human serum (30% serum in MH medium) was investigated and G3KL was shown to retain the low MIC observed in MH medium. The proteolytic stability was measured and G3KL was shown to be quite stable in serum in contrast to linear sequences that are very active in MH medium but loose activity in serum due to proteolytic degradation.

A large panel of multidrug resistant pathogens were investigated with G3KL. The dendrimer was very active for almost all strains of *P. Aeruginosa* and *A. Baumanii* tested independent of the resistant mechanism. The MBC was also determined for G3KL which showed the dendrimer to be bactericidal with MBC value identical or very close to the MIC. The dendrimers were not toxic to the human cells after a prolonged exposition.

A second generation peptide dendrimers with a lipid side chain C10 ($CO(CH_2)_8CH_3$) in the core G2KLC10 and analogues were also found to be very active against *P. aeruginosa* (PA). In particular three new very active compounds against PA including clinical isolates could be identified. In addition one G2C10 AMPD showed good activity against MRSA. Although second generation dendrimers are smaller then third generation dendrimers (G2KL 17 amino acid residues and G3KL 37 amino acid residues), the G2 dendrimers with lipid chain are active in the presence of serum and show good stability in serum (see G2KLC10 and TNS-122)

---

The invention claimed is:

1. A method of antibacterial treatment, comprising administering to a subject in need thereof, a peptide dendrimer described by a general formula X—(B²-[Y²]$_s$-D¹)$_2$-B¹Z, wherein X is
(D²)$_4$, or
(D³)$_8$-(B³-[Y³]$_r$-D²)$_4$,
and wherein
each Y (Y² and Y³) independently from any other Y is a linkage moiety di- or tripeptide H-Cys or CH-Cys linked to the N-terminus of the C-terminally neighboring amino acid in D through a thioether moiety exemplified by the formula

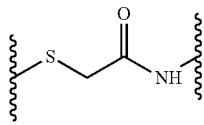

wherein the sulfur atom belongs to the cysteine and the amino group constitutes the N-terminus of the neighboring amino acid in D, wherein the C-terminus of cysteine is a carboxamide,
r and s is 0 or 1;
Z is a central moiety;
each B (B¹, B², and B³) independently from any other B denotes a diaminoalkylcarboxylic acid moiety described by the general formula: $C_nH_{2n-1}(NH_2)_2CO$— wherein n is a number between 2 and 10,
each D (D¹, D², and D³) independently from any other D is
i) a dipeptide CH, HC, CC or HH, or
ii) a tripeptide HCH, HHC, CHH, CCH, CHC, HCC, HHH or CCC wherein
H is any amino acid comprising a hydrophobic side chain, and
C is any amino acid comprising a cationic side chain, thereby providing antibacterial treatment to the subject.

2. The method according to claim 1, wherein
a) B¹, B², and B³ are independently selected from the group consisting of lysine, ornithine, 2,3-diaminopropionic acid and 2,3-diaminobutyric acid;
b) H is selected from the group consisting of leucine, phenylalanine, alanine, tyrosine or tryptophan, and/or
c) C is selected from the group consisting of lysine, arginine and 2,3-diaminobutyric acid.

3. The method 1 according to claim 1, characterized in that Z is linked to B via an amide bond between an amino function on Z to a carboxylic acid carbon on B¹, and each of D¹, D², and D³ is linked to its respective binding partner B¹, B², and B³ via an amide bond between an amino nitrogen on B¹, B², and B³ to a carboxylic acid carbon of D¹, D², and D³.

4. The method according to claim 1, wherein Z is a dipeptide CH, HC, CC, or HH, or a tripeptide HCH, HHC, CHH, CCH, CHC, HCC, HHH, or CCC, or Z is Lys, Leu, Lys-Leu, Arg-Leu, Dab-Trp, Dab-Leu, Leu-Lys, Lys-Trp, Lys-Phe, Lys-Lys, Leu-Leu, Dab-Ala, Lys-Lys-Leu, Lys-Leu-Leu, Leu-Lys-Leu, Lys-Leu-Lys, Orn-Leu, Orn-Phe, Arg-Phe, or Gly-Ser-Cys.

5. The method according to claim 1, wherein the peptide dendrimer is characterized by any of the formulae:
a) (KL)$_4$-(K—KL)$_2$-K—KL,
b) (KL)$_4$-(B—KL)$_2$-B—KL,
c) (RL)$_4$-(B-RL)$_2$-B-RL,
d) (KKL)$_4$-(K—KL)$_2$K—KL,
e) (DabW)$_4$-(K-DabW)$_2$-K-DabW,
f) (DabL)$_4$-(K-DabL)$_2$-K-DabL,
g) (KL)$_8$-(K—KL)$_4$-(K—KL)$_2$-K—KL,
h) (RL)$_8$-(K-RL)$_4$(K-RL)$_2$-K-RL,
i) (LK)$_8$-(K-LK)$_4$-(K-LK)$_2$-K-LK,
j) (KY)$_8$-(K—KL)$_4$-(K—KL)$_2$-K—KL,
k) (LA)$_8$-(K-LK)$_4$-(K-LA)$_2$-K—KL,
l) (KW)$_8$-(K-KW)$_4$-(K-KW)$_2$-K-KW,
m) (KF)$_8$-(K-KF)$_4$-(K-KF)$_2$-K-KF,
n) (KL)$_8$-(B—KL)$_4$-(B—KL)$_2$-B—KL,
o) (RL)$_8$-(B-RL)$_4$-(B-RL)$_2$-B-RL,
p) (LL)$_8$-(K-KK)$_4$-(K-LL)$_2$-K-KK,
q) (DabL)$_8$-(K-DabL)$_4$-(K-DabL)$_2$-K-DabL,
r) (DabL)$_8$-(K-DabW)$_4$-(K-DabL)$_2$-K-DabW,
s) (DabL)$_8$-(K-DabL)$_4$-(K-DabW)$_2$-K-DabW,
t) (DabL)$_8$-(K-DabW)$_4$-(K-DabW)$_2$-K-DabL,
u) (DabL)$_8$-(K-DabW)$_4$-(K-DabW)$_2$-K-DabA,
v) (DabL)$_8$-(K-DabW)$_4$-(K-DabA)$_2$-K-DabW,
w) (DabL)$_8$-(K-DabA)$_4$-(K-DabW)$_2$-K-DabW,
x) (KL)$_8$-(K—KLCKL)$_4$-(K—KL)$_2$-K—KL,
y) (KL)$_{16}$-(K—KL)$_8$-(K—KLCKL)$_4$-(K—KL)$_2$-K—KL,
z) (KL)$_{16}$-(K—KLCKL)$_8$-(K—KL)$_4$-(K—KL)$_2$-K—KL,
aa) (RL)$_8$-(K-RLCRL)$_4$-(K-RL)$_2$-K-RL,
bb) (KKL)$_4$-(K-KKL)$_2$-K-KKL,
cc) (KLL)$_4$-(K—KLL)$_2$-K—KLL,
dd) (LKL)$_4$-(K-LKL)$_2$-K-LKL,
ee) (KLL)$_8$-(K—KLL)$_4$-(K—KLL)$_2$-K—KLL,
ff) (LKL)$_8$-(K-LKL)$_4$-(K-LKL)$_2$-K-LKL,
gg) (KL)$_8$-(K—KL)$_4$-(K-LKL)$_2$-K-KKL,
hh) (KL)$_8$-(K—KL)$_4$-(K-LKL)$_2$-K—KLL,
ii) (KL)$_8$-(K—KL)$_4$-(K-LKL)$_2$-K—KLK,
jj) (KL)$_8$-(K—KL)$_4$-(K-LKL)$_2$-K-LKL,
kk) (KL)$_4$-(K—KL)$_2$-K—KLK—(CO(CH$_2$)$_4$CH$_3$,
ll) (KL)$_4$-(K—KL)$_2$-K—KLK—(CO(CH$_2$)$_6$CH$_3$,
mm) (KL)$_4$-(K—KL)$_2$-K—KLK—(CO(CH$_2$)$_8$CH$_3$,
nn) (KL)$_4$-(K—KL)$_2$-K—KLK—(CO(CH$_2$)$_{10}$CH$_3$, oo) (KL)$_8$-(K—KL)$_4$-(K—KL)$_2$-K—KLK—(CO(CH$_2$)$_4$CH$_3$,
pp) (KL)$_8$-(K—KL)$_4$-(K—KL)$_2$-K—KLK—(CO(CH$_2$)$_6$CH$_3$,
qq) (KL)$_8$-(K—KL)$_4$-(K—KL)$_2$-K—KLK—(CO(CH$_2$)$_8$CH$_3$,
rr) (KL)$_8$-(K—KL)$_4$-(K—KL)$_2$-K—KLK—(CO(CH$_2$)$_{10}$CH$_3$,
ss) (KL)$_8$-(K—KL)$_4$-(K—KL)$_2$-K—KLK—(CO(CH$_2$)$_{14}$CH$_3$,
tt) (KL)$_8$-(K—KL)$_4$-(K—KL)$_2$-K—KLK—(CO(CH$_2$)$_{16}$CH$_3$,
uu) (KL)$_8$-(K—KL)$_4$-(K—KL)$_2$-K—KLK—(CO(CH$_2$)$_{22}$CH$_3$,
vv) (KL)$_4$-(K—KL)$_2$-K—KLK—(CO(CH$_2$)$_{16}$CH$_3$,
ww) (CH$_3$(CH$_2$)$_4$CO-KL)$_8$-(K—KL)$_4$-(K—KL)$_2$-K—KL,
xx) (CH$_3$(CH$_2$)$_4$CO-KL)$_4$-(K—KL)$_2$-K—KL,
yy) (KK)$_8$-(K-KK)$_4$-(K-LL)$_2$-K-LL,
zz) (KK)$_8$-(K-LL)$_4$-(K-KK)$_2$-K-LL,
aaa) (KL)$_4$-(K—KL)$_2$-K—KLK—(CO(CH$_2$)$_{14}$CH$_3$,
bbb) (KL)$_4$-(K—KL)$_2$-K—KLK—(CO(CH$_2$)$_{22}$CH$_3$,
ccc) (KK)$_8$-(K-LL)$_4$-(K-LL)$_2$-K-GSC,
ddd) (KK)$_8$-(K-KK)$_4$-(K-LL)$_2$-K-GSC,
eee) (KK)$_8$-(K-KK)$_4$-(K-KK)$_2$-K-GSC,
fff) (KL)$_8$-(K-LL)$_4$-(K-LL)$_2$-K-GSC,
ggg) (KL)$_8$-(K—KL)$_4$-(K-LL)$_2$-K-GSC,
hhh) (KL)$_8$-(K—KL)$_4$-(K—KL)$_2$-K-GSC,
iii) (KA)$_8$-(K-KA)$_4$-(K-KA)$_2$-K-GSC,
jjj) (KH)$_8$-(K-KH)$_4$-(K-KH)$_2$-K-GSC,
kkk) (RL)$_8$-(K-LL)$_4$-(K-LL)$_2$-K-GSC,
lll) (RL)$_8$-(K-RL)$_4$-(K-LL)$_2$-K-GSC,
mmm) (RL)$_8$-(K-RL)$_4$-(K-RL)$_2$-K-GSC,
nnn) (OrnL)$_4$-(K-DabF)$_2$-K—KL,
ooo) (OrnF)$_4$-(K-DabL)$_2$-K—KL,
ppp) (RF)$_4$-(K-DabL)$_2$-K—KL,
qqq) (OrnF)$_4$-(K-DabL)$_2$-K—KLK—(CO(CH$_2$)$_8$CH$_3$,
rrr) (OrnL)$_4$-(K-DabF)$_2$-K—KLK—(CO(CH$_2$)$_8$CH$_3$, or
sss) (RF)$_4$-(K-DabL)$_2$-K—KLK—(CO(CH$_2$)$_8$CH$_3$.

6. The method according to claim 1, wherein Z and/or an N-terminal D of the dendrimer is coupled to an alkylcarboxylic acid moiety, described by a general formula CH$_3$(CH$_2$)$_n$CO—, and wherein n is a number between 4 and 22.

7. The method according to claim 1, wherein the antibacterial treatment is treatment of infection caused by a bacteria selected from the group consisting of *Pseudomonas aeruginosa, Acinetobacter baumannii, Escherichia coli, Staphylococcus aureus, Klebsiella* and methicillin-resistant *S. aureus* (MRSA strain).

8. The method according to claim 1, wherein H is a (D)- or (L)-amino acid comprising a hydrophobic side chain selected from the group consisting of glycine, alanine, valine, isoleucine, leucine, methionine, phenylalanine, tyrosine, and tryptophan, and
C is a (D)- or (L)-amino acid comprising a cationic side chain selected from the group consisting of lysine, arginine, ornithine, 2,3-diaminobutyric acid, 2,3-diaminopropionic acid, and histidine.

9. The method according to claim 1, wherein the antibacterial treatment is treatment of infection caused by a bacteria selected from the group consisting of *Bacillus subtilis, Citrobacter freundii, Citrobacter koseri, Enterobacter cloacae, Enterobacter aerogenes, Proteus mirabilis*, and *Salmonella Kentucky*.

\* \* \* \* \*